United States Patent
Ebata et al.

(10) Patent No.: US 10,234,388 B2
(45) Date of Patent: Mar. 19, 2019

(54) SYSTEM FOR DETERMINING ABNORMALITY IN A MONITORED AREA

(71) Applicant: HOCHIKI CORPORATION, Tokyo (JP)

(72) Inventors: Hiromichi Ebata, Tokyo (JP); Atsushi Mammoto, Tokyo (JP)

(73) Assignee: HOCHIKI CORPORATION, Tokyo (JP)

( * ) Notice: Subject to any disclaimer, the term of this patent is extended or adjusted under 35 U.S.C. 154(b) by 0 days.

(21) Appl. No.: 15/553,351

(22) PCT Filed: Feb. 5, 2016

(86) PCT No.: PCT/JP2016/053562
§ 371 (c)(1),
(2) Date: Aug. 24, 2017

(87) PCT Pub. No.: WO2016/136434
PCT Pub. Date: Sep. 1, 2016

(65) Prior Publication Data
US 2018/0073982 A1 Mar. 15, 2018

(30) Foreign Application Priority Data
Feb. 25, 2015 (JP) .................. 2015-035635

(51) Int. Cl.
*G01N 21/53* (2006.01)
*G01N 21/61* (2006.01)
(Continued)

(52) U.S. Cl.
CPC ............. *G01N 21/61* (2013.01); *G01N 21/53* (2013.01); *G01N 27/4162* (2013.01);
(Continued)

(58) Field of Classification Search
None
See application file for complete search history.

(56) References Cited

U.S. PATENT DOCUMENTS 6,788,197 B1  9/2004  Thuillard et al.
7,969,296 B1  6/2011  Stell
(Continued)

FOREIGN PATENT DOCUMENTS

DE  19934171 A1  1/2000
EP   1103937 A1  5/2001
(Continued)

OTHER PUBLICATIONS

International Search Report and Written Opinion (with English translation) of corresponding International Application No. PCT/US2016/053562; dated Apr. 5, 2016; 8 pages.
(Continued)

*Primary Examiner* — Shawn Decenzo
(74) *Attorney, Agent, or Firm* — Shumaker, Loop & Kendrick, LLP

(57) ABSTRACT

A system including a first information acquisition unit configured to acquire first information indicating a detection value of a first physical quantity in a monitored area, a second information acquisition unit configured to acquire second information indicating a detection value of a second physical quantity different from the first physical quantity, in the monitored area, and a determination unit configured to determine whether an abnormality has occurred in the monitored area, based on the detection value of the first physical quantity indicated by the first information, the detection value of the second physical quantity indicated by the second information, a first coefficient corresponding to the detection value of the first physical quantity and the detection value of the second physical quantity, and a first threshold.

3 Claims, 34 Drawing Sheets

(51) Int. Cl.
  *G08B 17/10*  (2006.01)
  *G08B 21/14*  (2006.01)
  *G08B 29/18*  (2006.01)
  *G01N 27/416*  (2006.01)
  *G08B 17/107*  (2006.01)
  *G08B 17/117*  (2006.01)

(52) U.S. Cl.
  CPC ............ *G08B 17/10* (2013.01); *G08B 17/117* (2013.01); *G08B 29/188* (2013.01); *G08B 17/107* (2013.01); *G08B 21/14* (2013.01)

(56) References Cited

U.S. PATENT DOCUMENTS

| | | | |
|---|---|---|---|
| 2008/0246623 A1* | 10/2008 | Nagashima | G01N 21/21 340/630 |
| 2013/0008787 A1* | 1/2013 | Mammoto | G08B 17/10 204/407 |
| 2014/0015678 A1 | 1/2014 | Zribi et al. | |

FOREIGN PATENT DOCUMENTS

| | | |
|---|---|---|
| EP | 2549453 A1 | 1/2013 |
| GB | 2339946 B | 10/2002 |
| JP | S6198498 A | 5/1986 |
| JP | 2000-57469 A | 2/2000 |
| JP | 200057469 A | 2/2000 |
| JP | 2000-516000 A | 11/2000 |
| JP | 3779325 A | 11/2000 |
| JP | 2003-162778 A | 6/2003 |
| JP | 2003162778 A | 6/2003 |
| JP | 2009-193315 A | 8/2009 |
| JP | 2009193315 A | 8/2009 |
| WO | 2011089879 A1 | 7/2011 |

OTHER PUBLICATIONS

English translation of the International Preliminary Report on Patentability and Written Opinion for PCT/JP2016/053562; dated Aug. 29, 2017; 5 pages.

Communication pursuant to Rule 164(1) EPC of corresponding EP Application No. 16755183.7; 12 pages; dated Aug. 18, 2018.

\* cited by examiner

Fig. 4

[CO-smoke conversion coefficient-specifying information]

| CO gas concentration (ppm) | CO-smoke conversion coefficient ((%/m)/ppm) |
|---|---|
| less than 30 (ppm) | 0.1 |
| 30 (ppm) or more to less than 60 (ppm) | 0.23 |
| 60 (ppm) or more | 0.3 |

Fig. 13

[CO-smoke conversion coefficient-specifying information]

| CO gas concentration (ppm) | CO-smoke conversion coefficient ((%/m)/ppm) | |
|---|---|---|
| | first CO-smoke conversion coefficient | second CO-smoke conversion coefficient |
| less than 30 (ppm) | 0.05 | 0.1 |
| 30 (ppm) or more to less than 60 (ppm) | 1.5 | 0.23 |
| 60 (ppm) or more | 2.0 | 0.3 |

Fig. 14

[second sensitivity coefficient information]

| second sensitivity coefficient | | temperature difference ΔT(°C) | | | |
|---|---|---|---|---|---|
| | | lower than 5.5°C | 5.5 °C or higher to lower than 13.0 °C | 13.0 °C or higher to lower than 20.5 °C | 20.5 °C or higher |
| external temperature To(°C) | lower than 40.0 °C | 1.0 | 1.0 | 1.0 | 1.0 |
| | 40.0 °C or higher to lower than 50.0 °C | 1.0 | 1.1 | 1.2 | 1.3 |
| | 50.0 °C or higher to lower than 60.0 °C | 1.0 | 1.2 | 1.3 | 1.4 |
| | 60.0 °C or higher to lower than 70.0 °C | 1.0 | 1.3 | 1.4 | 1.5 |
| | 70.0 °C or higher to lower than 80.0 °C | 1.0 | 1.0 | 1.4 | 1.5 |
| | 80.0 °C or higher | 1.0 | 1.0 | 1.5 | 1.6 |

Fig. 25

[device-specifying information]

| detector | type | related device |
|---|---|---|
| first detector ID | only smoke | second detector ID |
| second detector ID | smoke and CO | none |

Fig. 30

[device-specifying information]

| detector | type | related device |
|---|---|---|
| first detector ID | only smoke and temperature | second detector ID |
| second detector ID | smoke, temperature and CO | none |

SYSTEM FOR DETERMINING ABNORMALITY IN A MONITORED AREA

TECHNICAL FIELD

The present invention relates to a system.

BACKGROUND ART

Conventionally, there has been known a fire detector configured to detect fire occurrence in a monitored area. The fire detector is equipped with a fire sensor configured to detect the concentration or temperature of smoke in the monitored area and a determination unit configured to compare a detection value of the fire sensor with a predetermined threshold and determine that fire has occurred in the monitored area, when the detection value of the fire sensor exceeds the predetermined threshold.

In fumigation fire that often occurs in an initial stage of fire, however, if fire occurs in which a relatively small amount of smoke is generated, in a conventional smoke-type fire detector that detects smoke, it takes a relatively long time until a detection value of the fire sensor exceeds a predetermined threshold, which may delay detection of occurrence of the fire.

Hence, in order to promptly detect fire occurrence, there has been proposed a combined type fire detector configured to correct a detection value of a smoke sensor based on the concentration of carbon monoxide gas in the monitored area and then use the value after correction to detect fire occurrence in a monitored area (See Patent Document 1, for example). This combined type fire detector is equipped with a smoke sensor configured to detect the concentration of smoke in the monitored area, a gas sensor configured to detect the concentration of carbon monoxide gas in the monitored area, and a determination unit configured to determine that fire has occurred in the monitored area. Then, for example, when a detection value of the gas sensor is greater than or equal to a predetermined value, the determination unit corrects the detection value of the smoke sensor by multiplying the detection value of the smoke sensor by a constant to increase the detection value of the smoke sensor, and determines that fire has occurred in the monitored area when the detection value after correction exceeds a predetermined threshold.

PRIOR ART DOCUMENT

Patent Document

Patent Document 1: WO2011/089789

SUMMARY OF INVENTION

Technical Problem

However, in the fire detector in Patent Document 1, it takes a relatively long time until a detection value of the gas sensor becomes a predetermined value or higher when fire occurs in which a relatively small amount of carbon monoxide gas is generated. Therefore, it was difficult to promptly correct and increase a detection value of the smoke sensor.

In addition, in the fire detector in Patent Document 1, in the fumigation fire described above, when fire occurs in which an extremely small amount of smoke is generated although a relatively large quantity of carbon monoxide gas is generated for example, it takes a relatively short time until a detection value of the gas sensor becomes a predetermined time or higher. However, since a detection value of the smoke sensor which is a target of correction is extremely small, it was difficult to correct and substantially increase a detection value of the smoke sensor after being corrected.

Hence, as far as such a combined type fire detector is concerned, there is some room of improvement to promptly and reliably detect an abnormality such as fire in the monitored area.

It is an object of the present invention to solve the problems of the above mentioned prior art.

One aspect of the present invention provides a system including a first information acquisition means configured to acquire first information indicating a detection value of a first physical quantity in a monitored area, a second information acquisition means configured to acquire second information indicating a detection value of a second physical quantity different from the first physical quantity, in the monitored area, and a determination means configured to determine whether an abnormality has occurred in the monitored area, based on the detection value of the first physical quantity indicated by the first information, the detection value of the second physical quantity indicated by the second information, a first coefficient corresponding to the detection value of the first physical quantity and the detection value of the second physical quantity, and a first threshold.

BRIEF DESCRIPTION OF DRAWINGS

FIG. 1(a) is a perspective view showing the state of the detector mounted on a ceiling when viewed from the underside. FIG. 1(b) is a side view of the detector. FIG. 1(c) is a bottom view of the state of the detector when viewed from the underside.

FIG. 4 is a view showing CO-smoke conversion coefficient specifying information.

FIG. 10(a) is a perspective view showing the state of the detector mounted on a ceiling when viewed from the underside. FIG. 10(b) is a side view of the detector.

FIG. 10(c) is a bottom view of the state of the detector when viewed from the underside.

FIG. 13 is a view showing CO-smoke conversion coefficient-specifying information.

FIG. 14 is a view showing second sensitivity coefficient information.

FIG. 19(a) is a view showing the concentration of CO gas at each time. FIG. 19(b) is a view showing a multi-calculation value or the like at each time.

FIG. 25 is a view showing device-specifying information.

FIG. 30 is a view showing device-specifying information.

DESCRIPTION OF EMBODIMENTS

Respective embodiments of a system according to the present invention are described hereinafter with reference to the drawings. It should be noted that the present invention is not limited by the respective embodiments.

First, the basic concept of the respective embodiments is described. The embodiments schematically relate to a system configured to determine whether an abnormality has occurred in a monitored area, based on detection values of first physical quantity and second physical quantity, a first coefficient corresponding to a relation with the detection value of the first physical quantity and the detection value of the second physical quantity, and a predetermined threshold.

Here, a "monitored area" is an area monitored by the system, and is a concept including a room, a corridor, a staircase of a building or the like, for example. "Occurrence of an abnormality" is occurrence of the state which is different from normal states, and is a concept including fire occurrence, occurrence of toxic gas or the like, for example. In addition, "toxic gas" is gaseous matter that is toxic to living creatures, and is a concept including carbon monoxide or the like, for example. In addition, a "system" is configured to determine whether an abnormality has occurred in the monitored area, and is equipped with a detector or a receiver or the like, for example. In addition, a "detector" is a device configured to detect occurrence of an abnormality in the monitored area, and is a concept including a smoke detector, a gas detector, a heat detector, and a detector of combined type or the like, for example. In addition, a "receiver" is a device configured to receive various types of signals and announce occurrence of an abnormality in the monitored area.

Embodiment 1

First, an embodiment 1 is described. The embodiment 1 is an embodiment in a case in which it is determined whether an abnormality has occurred, based on a detection value of a smoke sensor, a detection value of a CO sensor, a first coefficient, and a determination threshold.

Configuration

Figure 1:
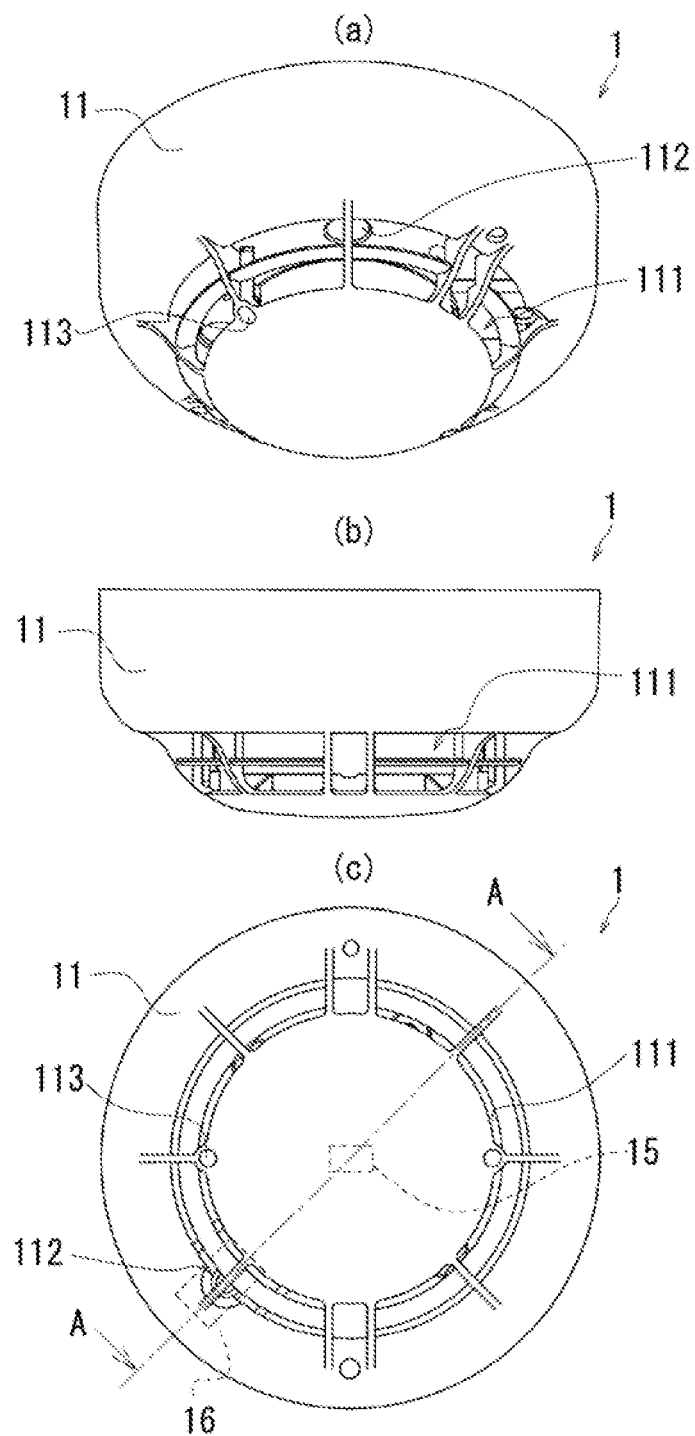
FIG. 1 is a diagram showing appearance of a detector according to an embodiment 1 of the present invention.
Figure 2:
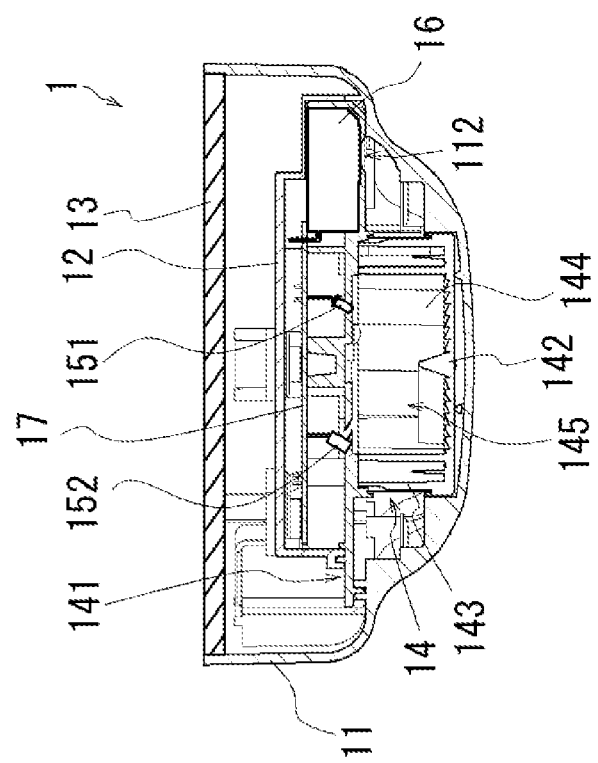
FIG. 2 is a cross sectional view along A-A in FIG. 1(c).

First, a configuration of a detector according to the embodiment 1 is described. FIG. 1 is a diagram showing appearance of the detector according to the embodiment 1. FIG. 1(a) is a perspective view showing the status of the detector mounted on a ceiling when viewed from the underside. FIG. 1(b) is a side view of the detector. FIG. 1(c) is a bottom view of the status of the detector when viewed from the underside. Note that although a smoke sensor 15 and a CO sensor 16 are not actually visible in FIG. 1(c), they are shown in a dashed line for convenience of the description (this also applies to FIG. 10(c) descried below). FIG. 2 is a cross sectional view along A-A in FIG. 1(c).

The detector 1 shown in FIG. 1 and FIG. 2 is an apparatus configured to detect fire occurrence in a monitored area. The detector 1 is an apparatus configured to detect fire occurrence, for example, as an abnormality and is connected to a receiver (not shown).

As shown in FIG. 1 and FIG. 2, the detector 1 is equipped with an outer cover 11, a lower cover 12, a mount base 13, a smoke sensing unit 14, a smoke sensor 15, a CO sensor 16, and a circuit board 17.

Configuration—Outer Cover

The outer cover 11 is a housing means configured to house the smoke sensing unit 14 and the circuit board 17, and includes a cylindrical part for housing the circuit board 17 and a dome-shaped part that is formed to protrude from the cylindrical part and houses the smoke sensing unit 14. The outer cover 11 is integrally formed by resin molding. In the outer cover 11 thus formed are provided a smoke inlet 111, an open hole 112, and an alarm activation indicator light 113.

The smoke inlet 111 is an opening to take smoke into the interior of a chamber 145 of the smoke sensing unit 14 described below. A plurality of the smoke inlets 111 are formed on, for example, a lateral face of the dome-shaped part of the outer cover 11 at regular intervals. The open hole 112 is an opening to take carbon monoxide gas (hereinafter referred to as "CO gas" as needed) into the interior of the outer cover 11. The open hole 112 is formed at position opposite to the CO sensor 16 in the outer cover 11 so that carbon monoxide gas flowing with smoke due to thermal air current associated with fire, for example is supplied to the CO sensor 16 described below. The alarm activation indicator light 113 is an announcement means configured to announce occurrence of an abnormality. The alarm activation indicator light 113 is configured as a LED provided on the outer cover 11 so that it can be visually recognized in the monitored area, and lights up or blinks when the detector 1 detects occurrence of an abnormality.

Configuration—Lower Cover

The lower cover 12 is a housing means that pairs with the above-described outer cover 11 to house the smoke sensing unit 14 and the circuit board 17. The lower cover 12 is, for example, a disk plate body almost corresponding to the inside diameter of the cylindrical part of the outer cover 11 and is formed by resin molding.

Configuration—Mount Base

The mount base 13 is a mounting means configured to mount the detector 1 in the monitored area. The mount base 13 is a disk plate body almost corresponding to the inside diameter of the cylindrical part of the outer cover 11 and is secured to the outer cover 11 by means of a predetermined structure such as screwing or fitting or the like. The mount base 13 which is thus secured to the outer cover 11 being fixed to a wall or ceiling in the monitored area by means of a screw or the like, the detector 1 can be installed in the monitored area.

Configuration—Smoke Sensing Unit

The smoke sensing unit 14 is a part configured to perform light scattering smoke detection, and includes a smoke sensing unit main body 141, a smoke sensing unit cover 142, and an insect screen 143. The smoke sensing unit main body 141 is formed in a disk shape as a whole, where a part of the smoke sensor 15 described below is arranged. The smoke sensing unit cover 142 is configured to cover the smoke sensing unit 14 and formed in a disk shape having a smaller diameter than the smoke sensing unit main body 141, and a labyrinth 144 is integrally formed on a face thereof on the side of the smoke sensing unit main body 141. The labyrinth 144 forms a chamber 145 as a smoke sensing space in the interior thereof, and blocks disturbance light that enters the chamber 145, thereby preventing it from entering a light receiving unit 152. The insect screen 143 is an insect proof means configured to prevent insect from entering the chamber 145 while allowing outside air to enter the chamber 145 through small openings, and is formed in an annular shape surrounding the outer periphery of the labyrinth 144 and has a multitude of small openings (not shown) sized to make it difficult for insects to enter. Then, smoke outside the detector 1 is sequentially taken into the interior of the chamber 145 through the smoke inlet 111 and the small openings of the insect screen 143.

Configuration—Smoke Sensor

The smoke sensor 15 is a detection means configured to detect the concentration of smoke as a detection target substance in the monitored area. The smoke sensor 15 is a light scattering smoke sensor, for example, provided in the interior of the detector 1. The smoke sensor 15 has a light emitting unit 151 and a light receiving unit 152, and a light emitting circuit 153 and a light receiving circuit 154 described below.

The light emitting unit 151 is a light emitting diode, for example, as a light emitting means configured to emit light. The light receiving unit 152 is a photodiode, for example, as a light receiving means configured to receive light. In order to prevent the light receiving unit 152 from being directly irradiated with light emitted from the light emitting unit 151, the light emitting unit 151 and the light receiving unit 152 are arranged so that an optical axis of the light emitting unit 151 and an optical axis of the light receiving unit 152 are not located on the same straight line. In addition, the light emitting unit 151 and the light receiving unit 152 are provided at a position where light emitted from the light emitting unit 151 is scattered by smoke particles and received by the light receiving unit 152, when smoke is present in the interior of the chamber 145.

Figure 3:
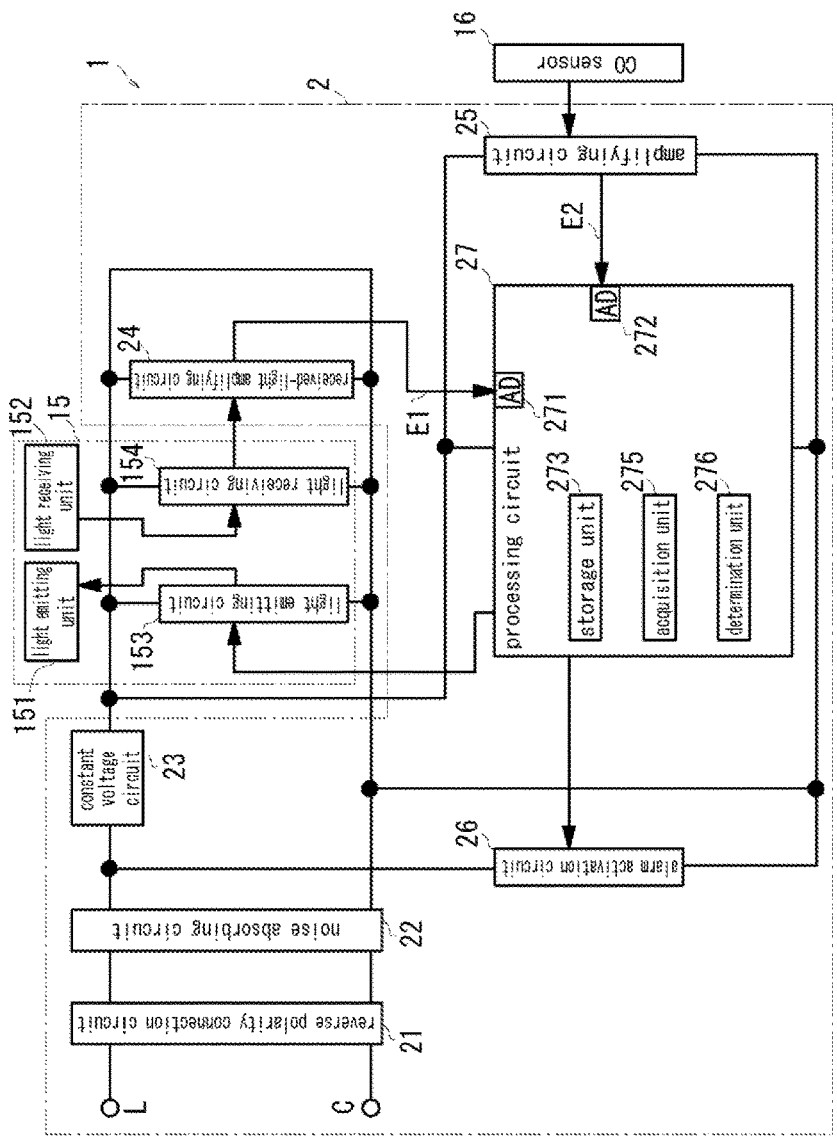
FIG. 3 is a block diagram of a detector circuit.

The light emitting circuit 153 is a light emission control means configured to control the light emitting unit 151. FIG. 3 is a block diagram of a detector circuit according to the embodiment. As shown in FIG. 3, the light emitting circuit 153 is connected with the light emitting unit 151 and drives the light emitting unit 151 so that light is emitted at predetermined timing.

The light receiving circuit 154 is a light reception control means configured to control the light receiving unit 152. The light receiving circuit 154 is connected with the light receiving unit 152 and outputs to a received-light amplifying circuit 24 described below a light reception amount signal that indicates an amount of light received at the light receiving unit 152.

The detection principle of smoke concentration by the smoke sensor 15, which is thus configured, is as per usual. That is, when no smoke is present in the interior of the chamber 145, light emitted by the light emitting unit 151 is not received by the light receiving unit 152. On the one hand, when smoke is present in the interior of the chamber 145, light emitted by the light emitting unit 151 is scattered by smoke particles and received by the light receiving unit 152. Furthermore, for example, when smoke is present in the interior of the chamber 145, an amount of light received by the light receiving unit 152 is defined based on the concentration of the smoke in the interior of the chamber 145. Therefore, if the smoke sensor 15 is used, the concentration of smoke can be detected based on the amount of light received by the light receiving unit 152.

Configuration—CO Sensor

In FIG. 1(c), FIG. 2, and FIG. 3, the CO sensor 16 is a detection means configured to detect the concentration of CO gas as a detection target substance in the monitored area. The CO sensor 16 is, for example, a carbon monoxide detection sensor of an electrochemical type provided in the interior of the detector 1, for example, and provided at a position opposite to the open hole 112 so that it can detect the concentration of CO gas taken into the interior of the detector 1 via the open hole 112. Note that a water-shedding filter (not shown) may be provided between the open hole 112 and the CO sensor 16, for example.

The detection principle of the concentration of CO gas by the CO sensor 16, which is thus configured, is as per usual. That is, if CO gas comes into contact with an electrolyte solution (not shown), with which the CO sensor 16 is filled, by way of a detection surface of the CO sensor 16, electric current is outputted from a predetermined electrode (not shown) of the CO sensor 16. Then, an amount of currents outputted from the predetermined electrode of the CO sensor 16 is defined based on the concentration of the CO gas that comes into contact with the electrolyte solution in the CO sensor 16. Therefore, if the CO sensor 16 is used, the concentration of CO gas can be detected based on an amount of currents outputted from the predetermined electrode.

Configuration—Circuit Board

The circuit board 17 is a mounting board on which a detector circuit 2 of the detector 1 as shown in FIG. 3 is mounted.

Configuration—Circuit Board—Detector Circuit

The detector circuit 2 is an electric circuit mounted on the circuit board 17 and connected to a detector line (not shown) drawn out of a receiver (not shown) by way of a terminal L and a terminal C which are provided in the detector 1. The detector circuit 2 has a reverse polarity connection circuit 21, a noise absorbing circuit 22, a constant voltage circuit 23, a received-light amplifying circuit 24, an amplifying circuit 25, an alarm activation circuit 26, and a processing circuit 27.

Configuration—Circuit Board—Detector Circuit—Reverse Polarity Connection Circuit The reverse polarity connection circuit 21 is a circuit configured to adjust polarity of voltage, and adjusts polarity of voltage so that voltage of predetermined polarity, which is predefined in advance, is supplied to the noise absorbing circuit 22, irrespective of polarity of the detector line connected to the terminal L and the terminal C. The reverse polarity connection circuit 21 has a diode bridge circuit, for example.

Configuration—Circuit Board—Detector Circuit—Noise Absorbing Circuit

The noise absorbing circuit 22 is a circuit configured to absorb or remove noise that is superimposed on voltage supplied from the detector circuit.

Configuration—Circuit Board—Detector Circuit—Constant Voltage Circuit

The constant voltage circuit 23 is a circuit configured to step down a source voltage supplied from the detector circuit and supply the source voltage after being stepped down to the light emitting circuit 153, the light receiving circuit 154, the light receiving amplifying circuit 24, the processing circuit 27, and the amplifying circuit 25.

Configuration—Circuit Board—Detector Circuit—Light Receiving Amplifying Circuit

The light receiving amplifying circuit 24 is a circuit configured to amplify amplitude of a light reception amount signal received from the light receiving circuit 154 and output the signal after being amplified as a smoke detection signal E1 to the processing circuit 27. The smoke detection signal E1 indicates an amount of light received at the light receiving unit 152 and corresponds to the smoke concentration detected by the smoke sensor 15.

Configuration—Circuit Board—Detector Circuit—Amplifying Circuit

The amplifying circuit 25 is a circuit configured to amplify amplitude of a current amount signal received from the CO sensor 16 and outputs the signal after being amplified as a CO detection signal E2 to the processing circuit 27. The CO detection signal E2 indicates an amount of currents outputted from the predetermined electrode in the CO sensor 16, and corresponds to the CO gas concentration detected by the CO sensor 16.

Configuration—Circuit Board—Detector Circuit—Alarm Activation Circuit

The alarm activation circuit 26 is a circuit configured to control alarm activation when occurrence of an abnormality is detected. The alarm activation circuit 26 is connected to the output side in the noise absorbing circuit 22 and controlled based on a signal received from the processing circuit 27. When the alarm activation circuit 26 receives a fire alarm activation signal from the processing circuit 27, for example, the alarm activation circuit 26 operates a switching element (not shown) provided on the alarm activation circuit 26 so that an alarm activation current is supplied in the detector line that is drawn from the receiver connected to the terminal L and the terminal C. Furthermore, when the alarm activation circuit 26 receives a fire alarm activation signal from the processing circuit 27, the alarm activation circuit 26 turns on the alarm activation indicator light 113 (FIG. 1(*a*)). That is, if the alarm activation circuit 26 receives a fire alarm activation signal from the processing circuit 27, the detector 1 transits from a normal monitoring state to an alarm activated state. Then, if a source voltage being supplied from the receiver to the detector line is blocked after this, the detector 1 recovers from the alarm activated state to the normal monitoring state. Note that blocking of the source voltage being supplied from the receiver to the detector line when the detector 1 is in the alarm activated state is referred to as a "recovery operation".

Configuration—Circuit Board—Detector Circuit—Processing Circuit

The processing circuit 27 is a processing means configured to perform various types of processing related to the detector 1. Specifically, it is a computer configured to comprise a CPU, various types of programs (including a basic control program such as an OS or an application program that is started on the OS to implement specific functions) interpreted and executed on the CPU, and an internal memory, such as a RAM, for storing the programs or various types of data. Particularly, a fire detection program according to the embodiment is installed in the detector 1 by way of any recording medium or a network so as to substantially configure each unit in the processing circuit 27 (which also similarly applies to processing circuits of each of instruments described below).

The processing circuit 27 has AD conversion units 271, 272, a storage unit 273, an acquisition unit 275, and a determination unit 276 in terms of a functional concept.

The AD conversion unit 271 is an analog-digital conversion circuit configured to convert the smoke detection signal E1 inputted to the processing circuit 27 into smoke data indicating the smoke concentration detected by the smoke sensor 15 and to output the smoke data after being converted. The AD conversion unit 272 is an analog-digital conversion circuit configured to convert the CO detection signal E2 inputted to the processing circuit 27 into CO data indicating the CO gas concentration detected by the CO sensor 16, and to output the CO data after being converted.

The storage unit 273 is a storage means in which programs and various types of data necessary for operation of the detector 1 are stored. In the storage unit 273 is stored CO-smoke conversion coefficient-specifying information (hereinafter also referred to simply as "conversion efficient-specifying information", as needed). FIG. 4 is a view showing CO-smoke conversion coefficient-specifying information according to the embodiment. The "CO-smoke conversion coefficient-specifying information" is information to specify a CO-smoke conversion coefficient (hereinafter also referred to simply as a "conversion coefficient", as needed). Here, the "CO-smoke conversion coefficient" is a coefficient for converting the CO data into data corresponding to the smoke data, and is a first coefficient used when a multi-calculation value described below is computed. As shown in FIG. 4, the "CO-smoke conversion coefficient-specifying information" is configured by correlating the item "CO gas concentration (ppm)" and the item "CO-smoke conversion coefficient ((%/m)/ppm)" to information corresponding to each item. Here, information corresponding to the item "CO gas concentration (ppm) is information to specify a range of the CO gas concentration ("less than 30 (ppm)", "30 (ppm) or more to less than 60 (ppm)", "60 (ppm) or more" in FIG. 4). In addition, information corresponding to the item "CO-smoke conversion coefficient ((%/m)/ppm)" is information to specify the CO-smoke conversion coefficient corresponding to the range of the CO gas concentration described above ("0.1", "0.23", "0.3" in FIG. 4). That is, the CO-smoke conversion coefficient-specifying information includes, for example, information indicating a range of CO gas concentration (corresponding to "less than 30 (ppm)", "30 (ppm) or more to less than 60 (ppm)", "60 (ppm) or more" in FIG. 4, for example) and information indicating the CO-smoke conversion coefficient corresponding to the range (corresponding to "0.1", "0.23", and "0.3" in FIG. 4, for example). The example of FIG. 4 shows that the CO-smoke conversion coefficient corresponding to each of "less than 30 (ppm)", "30 or more (ppm) to less than 60 (ppm)", "60 (ppm) or more" as the range of CO gas concentration is "0.1", "0.23", and "0.3". The CO-smoke conversion coefficient-specifying information is created based on, for example, relation information described below, and stored in the storage unit 273 by way of a predetermined input means (not shown) of the detector 1. Note that an example of a method of creating CO-smoke conversion coefficient-specifying information is described below.

Turning back to FIG. 3, the acquisition unit 275 is an acquisition means configured to acquire the CO-smoke conversion coefficient. The acquisition unit 275 acquires the CO-smoke conversion coefficient based on the CO data outputted from the AD conversion unit 272 and the CO-smoke conversion coefficient-specifying information (FIG. 4) stored in the storage unit 273. Note that specific processing by the acquisition unit 275 is described below.

The determination unit 276 is a determination means configured to determine whether fire has occurred in the monitored area. The determination unit 276 computes a multi-calculation value based on the smoke data outputted from the AD conversion unit 271 or the like, compares the computed multi-calculation value with a determination threshold described below, and determines whether fire has occurred in the monitored area based on a comparison result. Note that specific processing by the determination unit 276 is described below.

Processing

Figure 5:
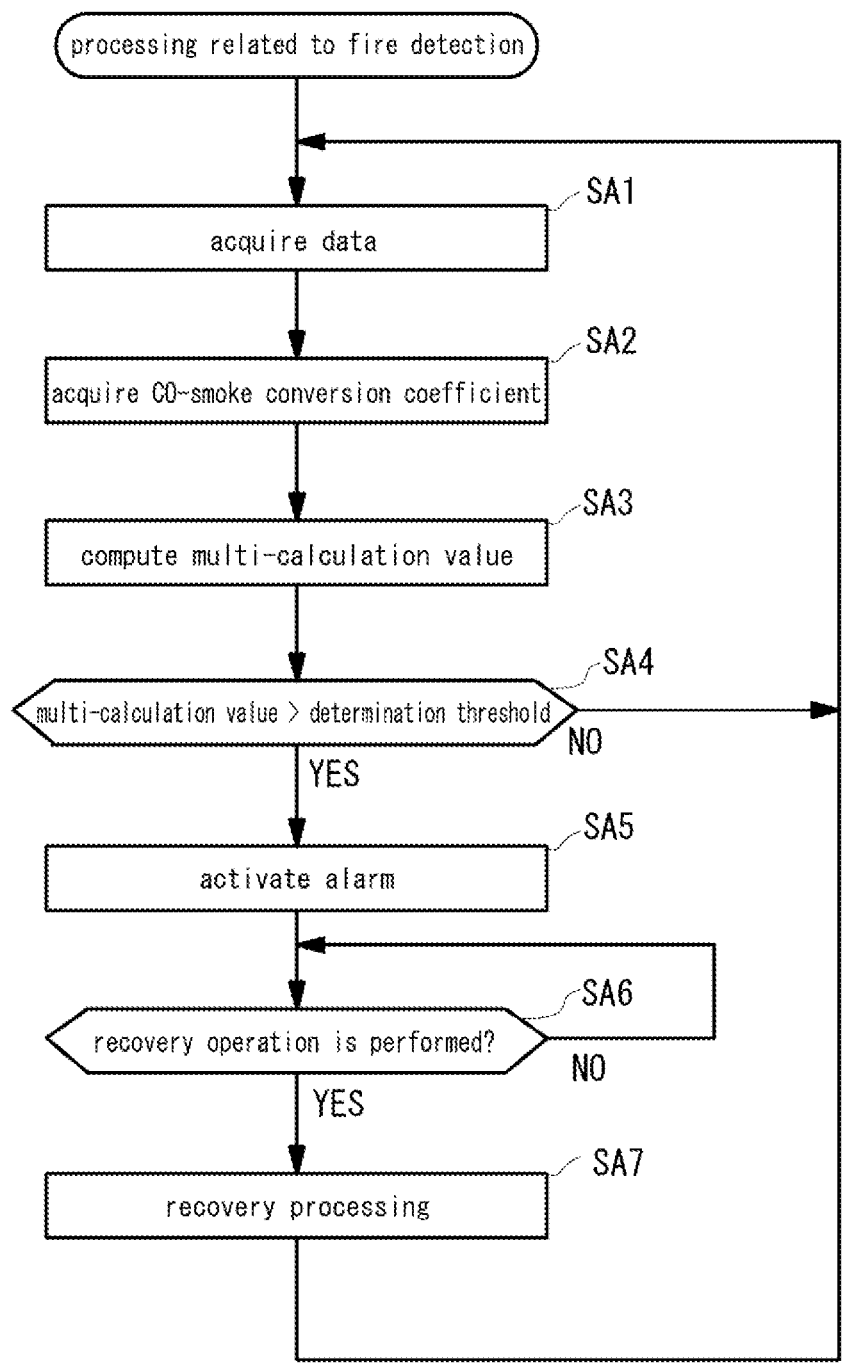
FIG. 5 is a flow chart of processing related to detection of fire.

Processing related to fire detection performed by the detector 1 which is thus configured is described hereinafter. FIG. 5 is a flow chart of processing related to fire detection according to the embodiment (a step is abbreviated to "S" in the following description of each processing). Note that an overall overview of the processing is described, and then details of each processing are described appropriately.

Processing—Overview

Processing related to fire detection is activated by, for example, installing the detector 1 in the monitored area, connecting the detector 1 through the detector line of the receiver to cause it to carry currents in order to bring the detector 1 into a monitoring state. The processing circuit 27 (FIG. 3) first receives a smoke detection signal E1 and a CO detection signal E2, and acquires the smoke data and the CO data corresponding to the received signals (SA1). Then, the acquisition unit 275 acquires a CO-smoke conversion coefficient based on the CO data acquired in SA1 and CO-smoke conversion coefficient-specifying information (FIG. 4) stored in the storage unit 273 (SA2). Then, the determination unit 276 computes a multi-calculation value (SA3) based on each piece of data or the like acquired in SA1 and the CO-smoke conversion coefficient acquired in SA2. Then, the determination unit 276 compares the multi-calculation value computed in SA3 with a determination threshold for determining whether fire has occurred in the monitored area (SA4), based on a comparison result. Note that the "determination threshold" is a threshold for determining whether fire has occurred, and is a first threshold used in the determination unit 276. In addition, the "determination threshold" may be preset based on a fire test (experiment) on a relation between the multi-calculation value and the presence or absence of fire occurrence. Then, based on a determination result in SA4, the processing circuit 27 performs processing of SA1 to SA3 again or each processing of SA5 to SA7 described below.

Specifically, in the determination in SA4, if the multi-calculation value falls below a determination threshold, for example, the determination unit 276 determines that no fire has occurred (NO in SA4). In this case, the processing circuit 27 makes a determination of SA4 again after performing the processing of SA1 to SA3 again. On the one hand, in the determination in SA4, if the multi-calculation value exceeds the determination threshold, the determination unit 276 determines that fire has occurred (YES in SA4). In this case, the processing circuit 27 transmits a fire alarm activation signal to the alarm activation circuit 26 (SA5). Then, the detector 1 transits from a normal monitoring state to an alarm activated state, operates so that an alarm activation current is supplied in the detector line, and further turns on the alarm activation light 113 (FIG. 1(a)). After this, if no recovery operation is performed (NO in SA6 in FIG. 5), the detector 1 maintains an alarm activated state. On the one hand, if the recovery operation is performed (YES in SA6), the detector 1 recovers from the alarm activated state to the normal monitoring state (SA7), and makes the determination in SA4 again after performing the processing of SA1 to SA3 again.

Processing—Details—Processing of SA2

Details of the processing of SA2 in FIG. 5 are described hereinafter. In this SA2, the acquisition unit 275 specifies a range of the CO gas concentration corresponding to the CO gas concentration indicated by the CO data acquired in SA1 in the CO-smoke conversion coefficient-specifying information, and acquires a CO-smoke conversion coefficient corresponding to the specified range of the CO gas concentration from the CO-smoke conversion coefficient-specifying information.

In FIG. 4, for example, if the CO gas concentration is 5 (ppm), for example, the acquisition unit 275 specifies "less than 30 (ppm)" as the range of the CO gas concentration corresponding to 5 (ppm), and acquires "0.1" as the CO-smoke conversion coefficient corresponding to the specified range. In addition, if the CO gas concentration is 40 (ppm), for example, the acquisition unit 275 specifies "30 (ppm) or more to less than 60 (ppm)" as the range of the CO gas concentration corresponding to 40 (ppm), and acquires "0.23" as the CO-smoke conversion coefficient corresponding to the specified range. In addition, if the CO gas concentration is 65 (ppm), for example, the acquisition unit 275 specifies "60 (ppm) or more" as the range of the CO gas concentration corresponding to 65 (ppm), and acquires "0.3" as the CO-smoke conversion coefficient corresponding to the specified range.

Processing—Details—Processing of SA3

Figure 6:
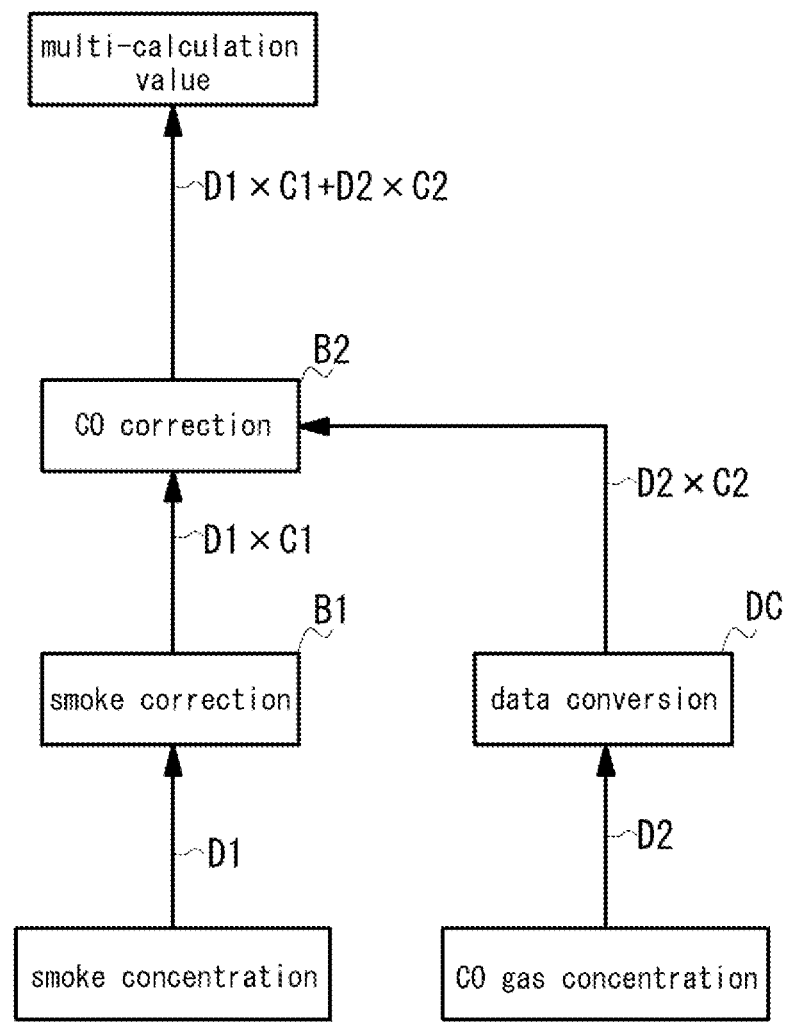
FIG. 6 is a view showing arithmetic processing performed in a determination unit.

Details of the processing of SA3 in FIG. 5 are described hereinafter. In this SA3, specifically, the determination unit 276 performs a smoke correction B1 and a CO correction B2 based on a conversion result of data conversion DC on the smoke concentration indicated by the smoke data outputted from the AD conversion unit 271, as described below, to compute a multi-calculation value. FIG. 6 is a view showing arithmetic processing performed in the determination unit according to the embodiment.

The smoke correction B1 is a correction for the smoke concentration indicated by the smoke data and is performed to reduce the detection sensitivity of fire occurrence to the smoke concentration. Specifically, the determination unit 276 performs the smoke correction B1 by multiplying the smoke concentration indicated by the smoke data by a first sensitivity coefficient. Here, a "first sensitivity coefficient" is a coefficient for adjusting the detection sensitivity of fire occurrence in the detector 1 and is a coefficient used when the determination unit 276 computes a multi-calculation value. The "first sensitivity coefficient" is set to a number equal to or smaller than 1 so that a value after the smoke correction B1 is performed becomes a value equal to or smaller than a value before the smoke correction B1 is performed. Then, if the smoke correction B1 is performed using a value less than 1 as the first sensitivity coefficient, it becomes possible to reduce occurrence frequency of non-fire alarms in the detector 1 because the fire detection sensitivity based on smoke can be reduced. Here, the "non-fire alarm" is a sort of false fire detection by a detector and means that even though fire has not occurred, the detector activates an alarm (false alarm) due to any reason other than fire, such as steam generated from a cooking apparatus, for example, or the like.

The data conversion DC refers to a conversion of the CO data into the data corresponding to the smoke data and is performed to create the data used in the CO correction B2 described below. Specifically, the determination unit 276 performs data conversion DC by multiplying the CO gas concentration indicated by the CO data by the CO-smoke conversion coefficient acquired in SA2 in FIG. 5.

Turning back to FIG. 6, the CO correction B2 is a correction for the smoke concentration indicated by the smoke data and performed to improve the sensitivity of detecting fire occurrence of the detector 1 itself. Specifically, the determination unit 276 performs the CO correction B2 by adding the value after being converted in the data conversion DC to the value after being corrected in the smoke correction B1. As described below, since the multi-calculation value can be promptly increased if fire occurs by performing the CO correction B2, fire occurrence can be detected promptly and reliably.

An example of computing the multi-calculation value is described with reference to FIG. 6. Here, a description is given, on the assumption that the smoke concentration indicated by the smoke data acquired in SA1 in FIG. 5 is "D1", the CO gas concentration indicated by the CO data acquired in SA1 in FIG. 5 is "D2", the CO-smoke conversion coefficient acquired by the acquisition unit 275 in SA2 in FIG. 5 is "C2", and the first sensitivity coefficient is "C1". In this FIG. 6, the determination unit 276 performs the smoke correction B1 by multiplying "D1" by "C1" and computes "D1×C1" as a correction result of the smoke correction B1. Then, the determination unit 276 performs the data conversion DC by multiplying "D2" by "C2" and computes "D2×C2" as a conversion result of the data conversion DC. Then, the determination unit 276 performs the CO correction B2 by adding "D2×C2" to "D1×C1" and computes "D1×C1+D2×C2" as a correction result of the CO correction B2, that is to say, the multi-calculation value.

Processing—Details—Processing of SA4

Details of the processing of SA4 in FIG. 5 are described hereinafter. In this SA4, as described above, the determination unit 276 determines whether fire has occurred in the monitored area. In the determination of fire, since the multi-calculation value is used, it becomes possible to perform detection of fire occurrence promptly and reliably, as described below, by reflecting the CO gas concentration as a fire-related element in the determination, in addition to the smoke concentration as the fire-related element.

Here, a reason why the detector 1 can detect fire occurrence promptly and reliably is described based on a relation with the fire-related element. First, when fire occurs, CO gas is generated, as a fire-related element, together with smoke. Then, flow velocities of the smoke and the CO gas are defined based on a type of fire (how a fire source burns). Flow velocities of smoke and CO gas when fumigation fire occurs, for example, are slower than flow velocities of smoke and CO gas when flaming fire occurs.

Figure 7:
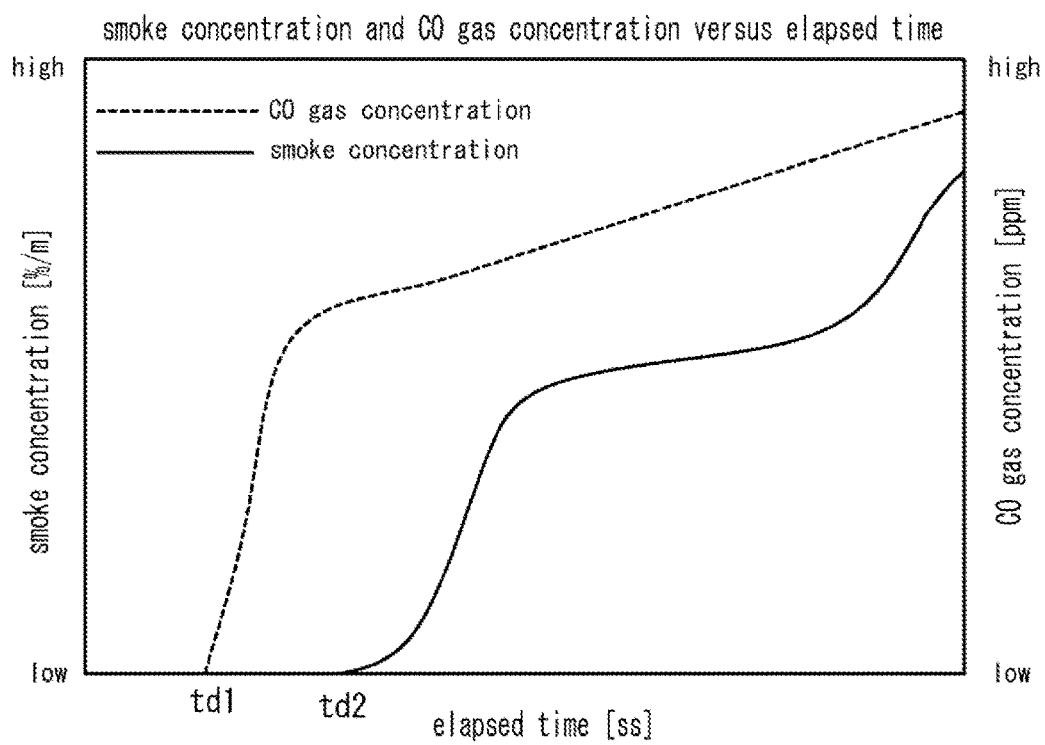
FIG. 7 is a view showing an experiment result regarding the smoke concentration and the CO gas concentration versus elapsed time.

Then, when flow velocities become relatively slow, there is a relatively large difference between detection start time of the smoke detector 15 of the detector 1 and detection start time of the CO sensor 16, as demonstrated by an experiment result described below. FIG. 7 is a view showing an experiment result regarding the smoke concentration and the CO gas concentration versus elapsed time, according to the embodiment. The horizontal axis of FIG. 7 represents time elapsed from when fire (here, fumigation fire) has occurred, i.e., when combustion of a combusted material has started. The vertical axis of FIG. 7 represents the smoke concentration corresponding to a detection value of the smoke sensor 15 and the CO gas concentration corresponding to a detection value of the CO sensor 16. Note that the detection start time td1 on the horizontal axis of FIG. 7 represents the time when the detection value by the CO sensor 16 exceeds the detection start concentration. The "detection start concentration" is concentration used as a criterion to determine that the CO sensor 16 starts to detect generation of CO gas and set to the relatively low concentration. In addition, the detection start time td2 on the horizontal axis of FIG. 7 represents the time when the detection value by the smoke sensor 15 exceeds the "detection start concentration related to smoke" of a similar configuration to the detection start concentration.

According to this FIG. 7, a relatively large difference is produced between the detection start time td1 of the CO sensor 16 and the detection start time td2 of the smoke sensor 15 of the detector 1, and the detection start time td1 is time earlier than the detection start time td2.

As the experiment result of this FIG. 7 shows, if flow velocities are slow (that is, when corresponding to the case in which fumigation fire has occurred), the CO sensor 16 detects the detection start concentration earlier than the smoke sensor 15 detects the detection start concentration related to smoke, and the detection value of the CO sensor 16 starts to rise earlier than the detection value of the smoke sensor 15 does. That is, this experiment result shows that uptake of smoke into the chamber 145 (FIG. 2) is delayed with respect to supply of CO gas to the CO sensor 16. Then, the delay is generated based on structure in the detector 1, such as a difference in a supply route to each sensor, wherein the insect screen 143 and the labyrinth 144 become a barrier when smoke is taken into the chamber 145, while CO gas is directly supplied to the CO sensor 16 without passing through the insect screen 143.

Then, as described above, in the case of the detector 1, it is possible to reflect the smoke concentration as a fire-related element along with the CO gas concentration as the element in the multi-calculation value by performing the CO correction B2. In addition, in the detector 1, since both the above described smoke correction B1 and this CO correction B2 are performed, it becomes possible to promptly and reliably detect fire occurrence, while reducing occurrence frequency of non-fire alarms.

Figure 8:
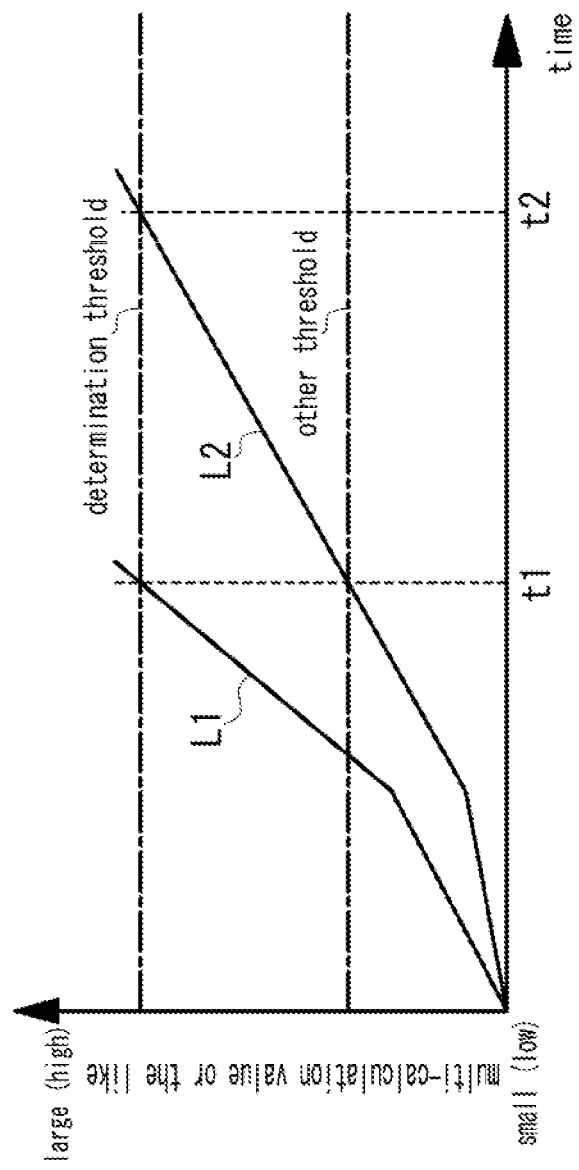
FIG. 8 is a view showing a multi-calculation value or the like at each time.

For example, FIG. 8 is a view showing the multi-calculation value or the like at each time. A line segment L1 represents the multi-calculation value (that is, a value corresponding to "D1×C1+D2×C2" in FIG. 6) used by the detector 1. Specifically, it represents the multi-calculation value when both of the smoke concentration indicated by the smoke data and the CO gas concentration indicated by the CO data continues to rise. On the one hand, a line segment L2 represents the smoke concentration (that is, a value corresponding to "D1" in FIG. 6) indicated by the smoke data that is used by a comparison target detector as a comparison target.

Then, the determination unit 276 computes a value corresponding to "D1×C1+D2×C2" in FIG. 6 as the multi-calculation value, and determines that no fire has occurred at time earlier than time t1 in FIG. 8, and determines that fire has occurred at time t1 that is earlier than time t2 which is detection time of the comparison target detector described below. As a result, in the comparison target detector represented by the line segment L2, since the smoke correction B1 and the CO correction B2 in FIG. 6 are not performed, a value of the line segment L2 is smaller than a value of the line segment L1 at each time. Thus, the comparison target detector detects fire occurrence at the time t2 which is later than the time t1. On the one hand, if the level of the determination threshold of FIG. 8 is lowered to the level of other threshold in the comparison target detector in order to accelerate detection of fire occurrence, the occurrence frequency of "non-fire alarms" as described above may increase. However, the detector 1 according to the embodiment can detect fire occurrence at the time t1 which is earlier than the time 2, and thus can detect fire occurrence more promptly and reliably than the comparison target detector. Furthermore, as shown in FIG. 8, the detector 1 can reduce the occurrence frequency of "non-fire alarms", because it can set the level of the determination threshold to a higher level than the level of the other threshold.

Conversion Coefficient-Specifying Information

Details of the CO-smoke conversion coefficient-specifying information (FIG. 4) are described hereinafter. The CO-smoke conversion coefficient-specifying information is created from relation information described below using an example of a predetermined creation method. The created CO-smoke conversion coefficient-specifying information is inputted to a predetermined input means (not shown) of the detector 1 and stored in the storage unit 273. The creation and input of the CO-smoke conversion coefficient-specifying information should be performed by a manufacturer or a user of the detector 1 or the like, for example, before the processing related to fire detection described above is activated.

Conversion Coefficient-Specifying Information—Relation Information

Figure 9:
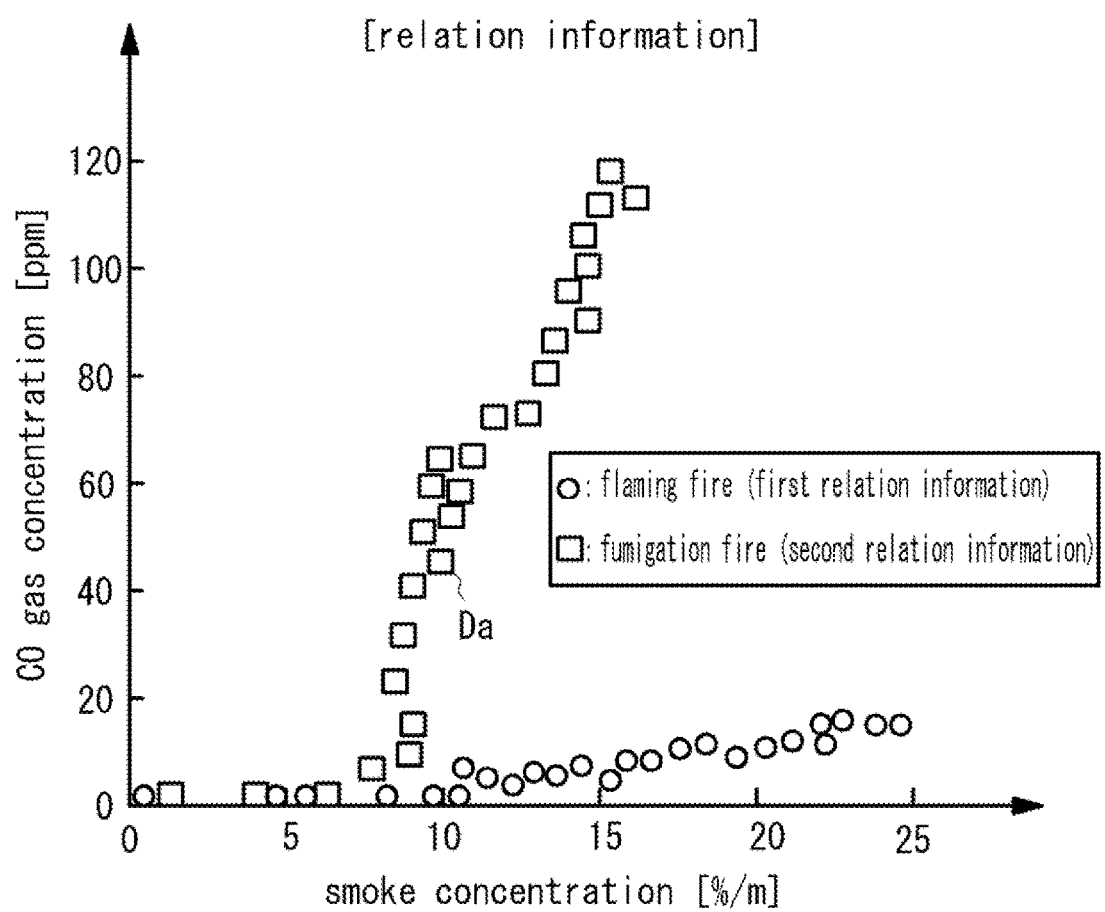
FIG. 9 is a view showing relation information.

FIG. 9 is a view showing relation information according to the embodiment. The "relation information" is information showing a relation between the smoke concentration and the CO gas concentration and used in creating CO-smoke conversion efficient-specifying information, for example. Specifically, the relation information is information to specify the smoke concentration and the CO gas concentration corresponding to the smoke concentration in the case in which a combusted material in an area corresponding to the monitored area is burned. The relation information is information corresponding to a test result of a fire test that burns the combusted material. In the relation information, the smoke concentration corresponds to a detection result of other smoke detecting apparatus described below, and the CO gas concentration corresponds to a detection result of the CO sensor 16 of the detector 1 or a CO sensor having a similar configuration to the CO sensor 16. The relation information includes a test result of a fire test corresponding to flaming fire and a test result of a fire test corresponding to fumigation fire (non-flame fire) which is different from the flaming fire, for a plurality of types of combusted materials. That is, the relation information includes first relation information (information represented by a circle mark in FIG. 9) that specifies the smoke concentration and the CO gas concentration related to occurrence of flaming fire, and second relation information (information represented by a rectangular mark in FIG. 9) that specifies the smoke concentration and the CO gas concentration related to occurrence of fumigation fire.

Conversion Coefficient-Specifying Information—Relation Information—Other Smoke Detecting Apparatus Other detecting apparatus is a smoke detection means that is different from the smoke sensor 15 of the detector 1. In the other smoke detecting apparatus, anything like the insect screen 143 of the detector 1 (FIG. 2), for example, is not provided, and it is such configured that smoke is supplied directly (that is, without going through anything like the insect screen 143 of the detector 1) to its own smoke detection area from the outside. Thus, in other smoke detecting apparatus, response speed relating to smoke detection is faster than the smoke sensor 15 of the detector 1. If a fire test similar to the fire test related to FIG. 7 is carried out, for example, detection start time of the other smoke detecting apparatus is similar time to the detection start time td1, and a detection value of the other smoke detecting apparatus has similar characteristics to the CO gas concentration. Note that "a detection value of the other smoke detecting device has similar characteristics to the CO gas concentration" means that a coefficient of fluctuation of a detection value of the other smoke detecting apparatus is similar to a coefficient of fluctuation of a detection value of the CO sensor 16 in the detector 1.

Then, since a detection result of the other smoke detecting apparatus is reflected in the relation information, it becomes possible to remove any influence of delay resulting from the fact that the insect screen 143 and the labyrinth 144 are provided, the delay being of the detection start time td2 (FIG. 7) with respect to the detection start time td1. Thus, fire occurrence can be detected more promptly and reliably.

Conversion Coefficient-Specifying Information—Creation

When CO-smoke conversion coefficient-specifying information is created, predetermined information is extracted from relation information (first relation information and second relation information), and the CO-smoke conversion coefficient-specifying information is created based on the extracted information. That is, although the CO-smoke conversion coefficient-specifying information is created based on the first relation information or the second relation information, in the embodiment, a case is described in which the CO-smoke conversion coefficient-specifying information is created based on the second relation information, for convenience of description. However, CO-smoke conversion coefficient-specifying information may be created based on the first relation information or the CO-smoke conversion coefficient-specifying information may be created based on both of the first and second relation information. As a method of creating CO-smoke conversion coefficient-specifying information, any of the creation methods of a first creation method to a fourth creation method described below, for example, a combination of the creation methods, or a combination of some of the creation methods may be used.

Conversion Coefficient-Specifying Information—Creation—First Creation Method

In the first creation method, each piece of data in the second relation information is divided into groups, a CO-smoke conversion coefficient is acquired for each of the divided groups, and CO-smoke conversion coefficient-specifying information in which the acquired CO-smoke conversion coefficient is reflected is created.

Specifically, first, each piece of data in the second relation information (corresponding to each plot with the rectangular marks in FIG. 9) is divided for each group based on a predetermined segment threshold described below. In the embodiment, for example, a case is described in which "30 (ppm)" and "60 (ppm)" as the concentration related to CO gas are considered as a predetermined segment threshold. In this case, each piece of data is divided into data with the CO gas concentration being less than 30 (ppm) (hereinafter also referred to as "first group data"), data with the CO gas concentration being 30 (ppm) or more to less than 60 (ppm) (hereinafter also referred to as "second group data"), and data with the CO gas concentration being 60 (ppm) or more (hereinafter also referred to as "third group data".

Then, a CO-smoke conversion coefficient is acquired for each group divided using a predetermined threshold. Specifically, for example, a linear approximation equation corresponding to data in each group may be determined and the slope of the linear approximation equation may be acquired as a CO-smoke conversion coefficient corresponding to each group. Alternatively, an n-order approximation equation (note that "n" is an integer of 2 or higher) including a quadratic approximation equation or a third-order approximation equation corresponding to data in each group or the like may be determined and a CO-smoke conversion coefficient may be acquired based on the determined approximation expression.

Then, CO-smoke conversion coefficient-specifying information including information indicating a range of groups divided by a predetermined segment threshold (range of the CO gas concentration, for example) and information indicating the acquired CO-smoke conversion coefficient is created. Here, a "predetermined segment threshold" is a threshold used to divide each piece of data of the relation information into groups.

As the predetermined segment threshold, for example, a value related to the CO gas concentration or a value related to the smoke concentration may be used. If the value related to the CO gas concentration is used as a predetermined segment threshold, as shown in FIG. 4, CO-smoke conversion coefficient-specifying information that associates the range of CO gas concentration with the CO-smoke conversion coefficient is created. On the one hand, if the value related to the smoke concentration is used as a predetermined segment threshold, CO-smoke conversion coefficient-specifying information (not shown) that associates the range of the smoke concentration and the CO-smoke conversion coefficient is created.

In addition, a value related to the criterion for determining fire may be used as a predetermined segment threshold. For example, "30 (ppm)" and "60 (ppm)" used as a predetermined segment threshold in the embodiment correspond to a value used as a criterion in the case in which fire occurrence in the monitored area is determined using only the CO gas concentration (which may be hereinafter referred to also as "the case of fire determination with the CO gas concentration). Specifically, according to this criterion, if the CO gas concentration is less than 30 (ppm), for example, it should not be determined that fire has occurred, if the CO gas concentration is 60 (ppm) or more, it should be determined that fire has occurred, and if the CO gas concentration is 30 (ppm) or more to less than 60 (ppm), it may be determined that fire has not occurred or that fire has occurred, depending on the CO gas concentration.

Conversion Coefficient-Specifying Information—Creation—Second Creation Method

In the second creation method, first, each piece of data in the second relation information is divided into groups, similar to the first creation method. Then, one representative piece of data is acquired for each divided group, and a CO-smoke conversion coefficient is acquired based on the acquired representative data. Note that, "representative data" may be data (corresponding to "data Da" in FIG. 9, for example) corresponding to the predefined CO gas concentration or smoke concentration, or randomly defined data. Specifically, a ratio of the smoke concentration in the representative data with respect to the CO gas concentration in the representative data is computed, and the computed ratio is acquired as a CO-smoke conversion coefficient. In this embodiment, in the case in which a detection value of the smoke sensor 15 (smoke concentration) indicated by the data Da (FIG. 9) of data in the second group is "10 (%/m)" and a detection value of the CO sensor 16 (CO gas concentration) indicated by the data Da is "45 (ppm)", if the data Da is acquired as representative data, division of "10 (%/m)/ 45 (ppm)" is performed and "0.23 ((%/m)/(ppm)) resulting from the division is acquired as a CO-smoke conversion coefficient of the second group.

In addition, a plurality of pieces of data is acquired for each divided group, the above-mentioned ratio is determined for each acquired piece of data, a statistical value for each group of the plurality of determined ratios is determined, and the determined statistical value may be acquired as a CO-smoke conversion coefficient of each group. Note that "a plurality of pieces of data" acquired may be some data in each group or entire data. Then, CO-smoke conversion coefficient-specifying information is created, similar to the first creation method.

Creation of Conversion Coefficient-Specifying Information, Etc.—Creation—Third Creation Method In the third creation method, first, each piece of data in the second relation information is divided into groups, similar to the first creation method. Then, a CO-smoke conversion coefficient may be determined only for some groups of the divided groups similar to the first creation method or the second creation method described above, while a predefined value may be used as a CO-smoke conversion coefficient for some other groups. For example, in the case related to FIG. 4, a CO-smoke conversion coefficient may be acquired for the second group (for which the CO gas concentration is 30 (ppm) or more to less than 60 (ppm)) similar to the first creation method or the second creation method described above, an extremely small value may be acquired as a CO-smoke conversion coefficient for the first group (for which the CO gas concentration is less than 30 (ppm)), and an extremely large value may be acquired as a CO-smoke conversion coefficient for the third group (for which the CO gas concentration is 60 (ppm) or more). Note that the "extremely small value" is a value to the extent that the multi-calculation value computed using a CO-smoke conversion coefficient does not exceed a determination threshold (FIG. 8), and may be a value of about one-tenth of "0.23 ((%/m)/(ppm))" determined with the second creation method. In addition, the "extremely large value" is a value to the extent that the multi-calculation value computed using the CO-smoke conversion coefficient certainly exceeds the determination threshold (FIG. 8), and may be a value of about one-hundredfold of "0.23 ((%/m)/(ppm)" determined with the second creation method. Then, CO-smoke conversion coefficient-specifying information is created similar to the first creation method.

Creation of Conversion Coefficient-Specifying Information, Etc., —Creation—Fourth Creation Method In the fourth creation method, only one CO-smoke conversion coefficient is determined from the entire second relation information without grouping in the first creation method. In the fourth creation method, only one CO-smoke conversion coefficient may be acquired, similar to the first to third creation methods. Then, CO-smoke conversion coefficient-specifying information is created, similar to the first creation method.

Effect of the Embodiment 1

As such, according to the embodiment, since the CO-smoke conversion coefficient according to the CO gas concentration and the smoke concentration as shown in FIG. 9 can be reflected in a determination of whether an abnormality has occurred, irrespective of magnitude of the detection value of the smoke sensor 15 and the detection value of the CO sensor 16, occurrence of the abnormality can be detected promptly and reliably in the monitored area. Therefore, even when fire occurs in which a relatively small amount of CO gas is generated, the CO-smoke conversion coefficient can be reflected in the determination of whether fire has occurred, irrespective of the CO gas concentration. Thus, occurrence of the fire can be detected promptly and reliably. Alternatively, as with fumigation fire, even when fire occurs in which a relatively large amount of carbon monoxide gas is generated but an extremely small amount of smoke is generated, for example, the CO-smoke conversion coefficient can be reflected in the determination of whether fire has occurred, irrespective of the smoke concentration. Thus, occurrence of the fire can be detected promptly and reliably.

In addition, since the CO-smoke conversion coefficient can be acquired based on the detection value of the CO sensor 16 and the acquired CO-smoke conversion coefficient can be reflected in the determination of whether an abnormality has occurred, a CO-smoke conversion coefficient suitable for the environment in the monitored area can be reflected in the determination, and thus occurrence of the abnormality can be detected promptly and reliably.

In addition, a CO-smoke conversion coefficient that is defined in a step-by-step manner, depending on a range of the CO gas concentration in CO-smoke conversion coefficient-specifying information (FIG. 4), and the acquired CO-smoke conversion coefficient can be reflected in the determination of whether fire has occurred. Thus, by absorbing a detection error at the CO sensor 16, for example, it is possible to reflect a CO-smoke conversion coefficient suitable for the environment of the monitored area in the determination of whether fire has occurred, and occurrence of the fire can be detected promptly and reliably. Note that "absorbing a detection error at the CO sensor 16" corresponds to the fact that in the case of FIG. 4, for example, even if the detection value of the CO sensor 16 changes from "40 (ppm)" to "41 (ppm)" due to a detection error, "0.23" can be acquired as a CO-smoke conversion coefficient irrespective of the detection error.

In addition, in the relation information (FIG. 9), since a ratio of the smoke concentration with respect to the CO gas concentration, which are correlated, corresponds to a CO-smoke conversion coefficient, the detection value of the CO sensor 16 can be converted into a value corresponding to the detection value of the smoke sensor 15, by multiplying the CO-smoke conversion coefficient by the detection value of the CO sensor 16. Accordingly, the determination of whether fire has occurred can be made based on the criterion related to the smoke sensor 15, and fire occurrence can be detected promptly and reliably.

In addition, if CO-smoke conversion coefficient-specifying information is created based on only one predefined piece of data (data Da in FIG. 9, for example) in the relation information (FIG. 9), appropriate selection of data suitable for the determination of whether fire has occurred in the monitored area, based on an experiment or the like, for example, can prevent acquisition of a coefficient unsuitable as a CO-smoke conversion coefficient. Thus, occurrence of an abnormality in the monitored area can be detected promptly and reliably.

In addition, since it is possible to determine whether fire has occurred in the monitored area by using the multi-calculation value obtained by reflecting the CO-smoke conversion coefficient and the CO gas concentration indicated by the CO data to the smoke concentration indicated by the smoke data, fire occurrence in the monitored area can be detected promptly and reliably.

Embodiment 2

An embodiment 2 is described hereinafter. The embodiment 2 is an embodiment in a case in which a determination of whether an abnormality has occurred is made based on a detection value of a smoke sensor, a detection value of a CO sensor, a first coefficient, a second coefficient, and a determination threshold. Note that a configuration of the embodiment 2 is substantially identical to the configuration of the embodiment 1 unless otherwise specified. Any configuration which is substantially identical to that of the embodiment 1 is assigned with same symbols as those used in the embodiment 1 if needed, and a description thereof is omitted.

Configuration

Figure 10:
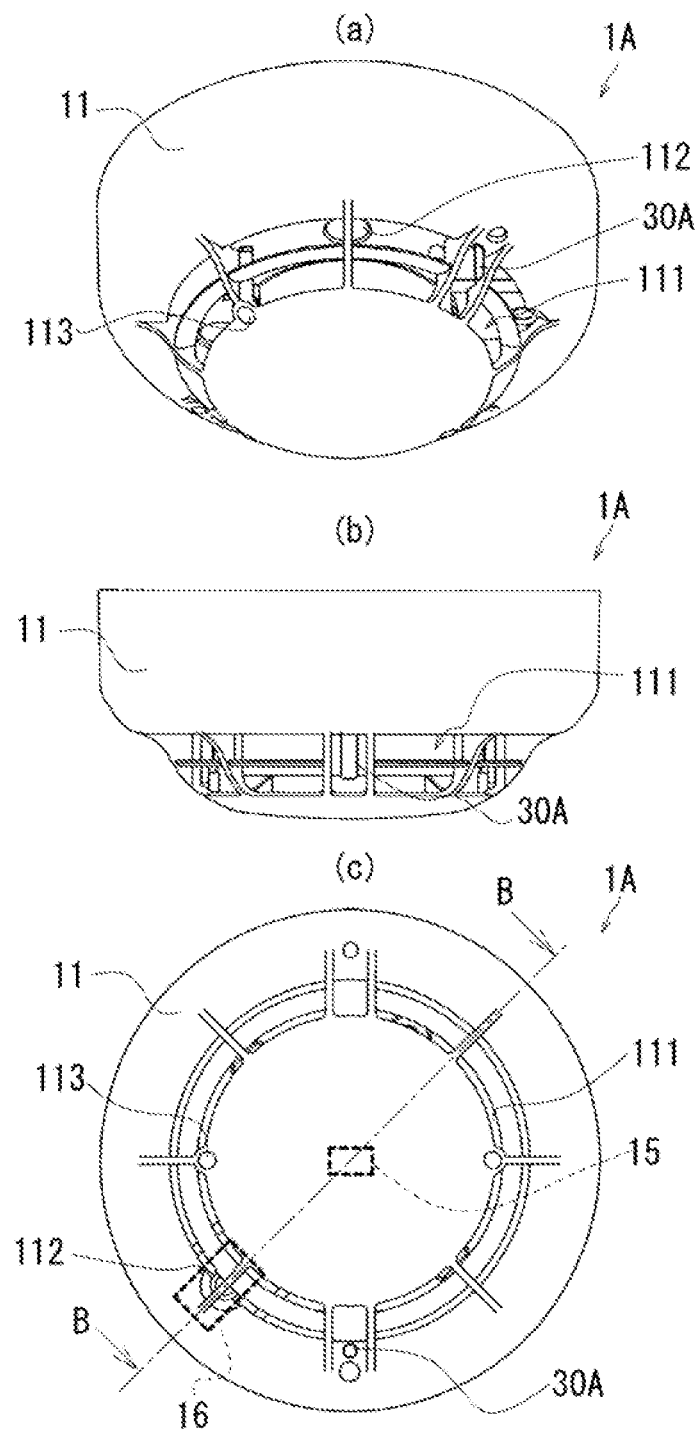
FIG. 10 is a view showing appearance of a detector according to an embodiment 2.
Figure 11:
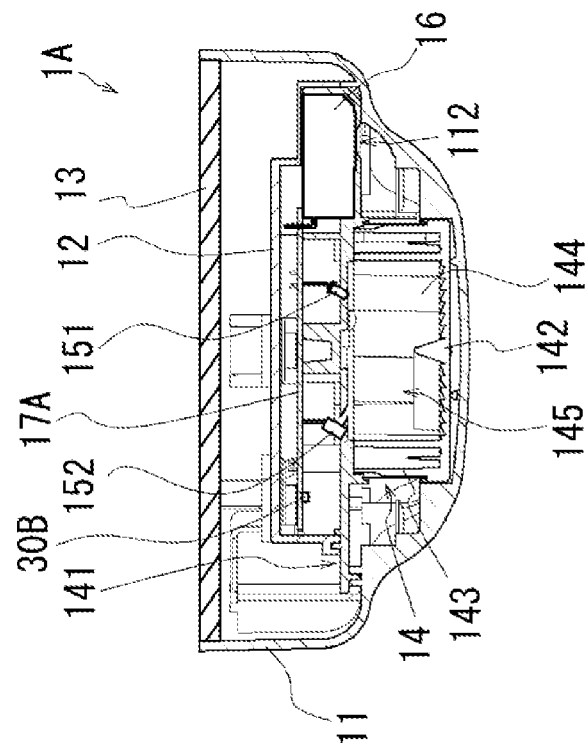
FIG. 11 is a cross sectional view along B-B in FIG. 10(c).

First, a configuration of a detector according to the embodiment 2 is described. FIG. 10 is a view showing appearance of the detector according to the embodiment. FIG. 10(a) is a perspective view showing the state of the detector mounted on a ceiling when viewed from the underside. FIG. 10(b) is a side view of the detector. FIG. 10(c) is a bottom view of the state of the detector when viewed from the underside. FIG. 11 is a cross sectional along B-B in FIG. 10(c).

As shown in FIG. 10 and FIG. 11, the detector 1A is equipped with an outer cover 11, a lower cover 12, a mount base 13, a smoke sensing unit 14, a smoke sensor 15, a CO sensor 16, an external temperature sensor 30A, an internal temperature sensor 30B, and a circuit board 17A. Note that for convenience of description, the external temperature sensor 30A and the internal temperature sensor 30B are also referred to collectively and simply as a "temperature sensor 30".

Configuration—External Temperature Sensor

The external temperature sensor 30A is a detection means configured to detect the temperature outside the detector 1A. The external temperature sensor 30A is arranged outside the outer cover 11 of the detector 1A, and is a temperature sensor including an external thermistor, for example. The detection principle of the temperature by the external temperature sensor 30A which is thus configured is as per usual. That is, the external temperature sensor 30A detects the temperature outside the detector 1A based on electric resistance of the external thermistor, a value of which is defined depending on the temperature, and outputs an external temperature signal indicating a detection result to an amplifying circuit 301, described below.

Configuration—Internal Temperature Sensor

The internal temperature sensor 30B is a detection means configured to detect the internal temperature of the detector 1A. The internal temperature sensor 30B is arranged on the circuit board 17A of the detector 1A and is a temperature sensor including an internal thermistor, for example. The detection principle of the temperature by the internal temperature sensor 30B which is thus configured is similar to the detection principle of the temperature by the external temperature sensor 30A as described above. That is, the internal temperature sensor 30B detects the internal temperature of the detector 1A based on electrical resistance of the internal thermistor, a value of which is defined depending on the temperature, and outputs an internal temperature signal indicating a detection result to the amplifying circuit 301.

Configuration—Circuit Board

Figure 12:
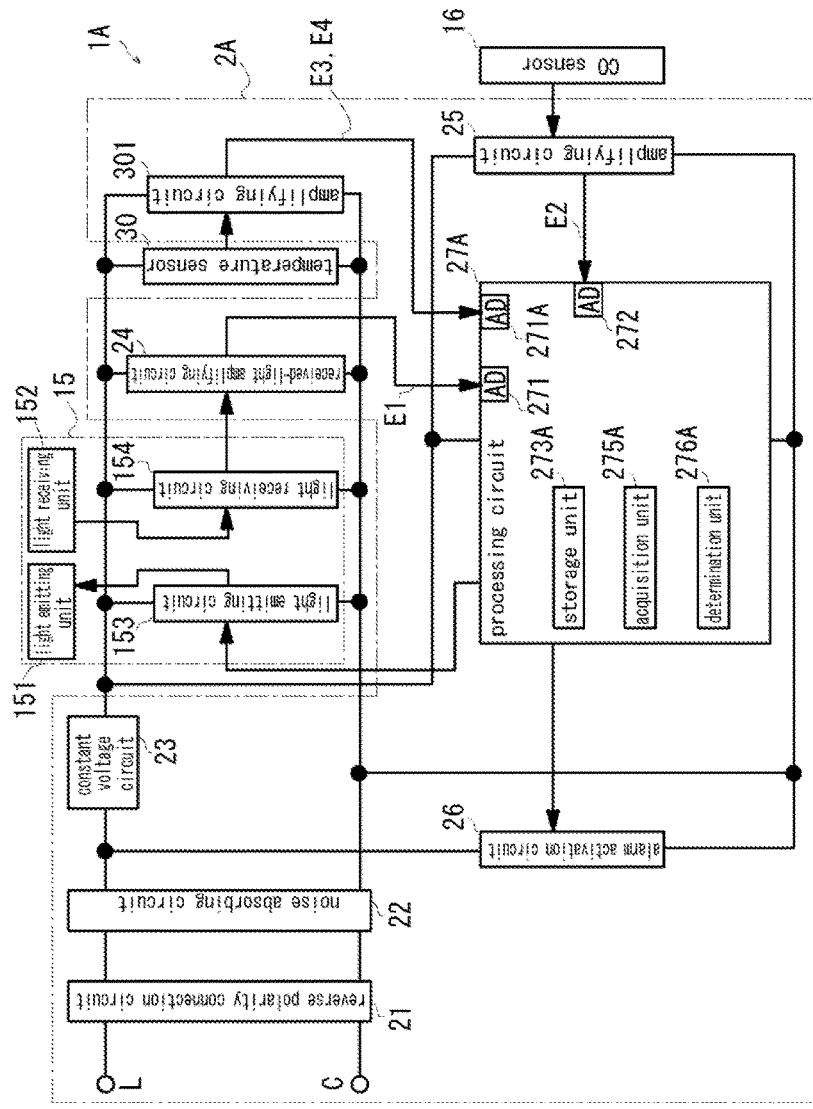
FIG. 12 is a block diagram of a detector circuit.

FIG. 12 is a block diagram of a detector circuit according to the embodiment. In FIG. 11 and FIG. 12, the circuit board 17A is a mounting board on which a detector circuit 2A of the detector 1A is mounted.

Configuration—Circuit Board—Detector Circuit

The detector circuit 2A has a reverse polarity connection circuit 21, a noise absorbing circuit 22, a constant voltage circuit 23, a received-light amplifying circuit 24, an amplifying circuit 25, an alarm activation circuit 26, an amplifying circuit 301, and a processing circuit 27A.

The amplifying circuit 301 amplifies amplitude of an external temperature signal received from the external temperature sensor 30A of the temperature sensor 30 and outputs the signal after being amplified as an external temperature detection signal E3 to the processing circuit 27A. In addition, the amplifying circuit 301 amplifies amplitude of an internal temperature signal received from the internal temperature sensor 30B of the temperature sensor 30 and outputs the signal after being amplified as an internal temperature detection signal E4 to the processing circuit 27A.

The processing circuit 27A has AD conversion units 271, 271A, 272, a storage unit 273A, an acquisition unit 275A, and a determination unit 276A in terms of a functional concept.

The AD conversion unit 271A is an analog-digital conversion circuit configured to convert the external temperature detection signal E3 and the internal temperature detection signal E4 inputted to the processing circuit 27A respectively into external temperature data indicating the external temperature and internal temperature data indicating the internal temperature detected by the temperature sensor 30 and to output the external temperature data and the internal temperature data after being converted.

The storage unit 273A is a storage means in which programs and various types of data necessary for operation of the detector 1A are stored. In the storage unit 273A, CO-smoke conversion coefficient-specifying information and second sensitivity coefficient information are stored.

Configuration—CO-Smoke Conversion Coefficient-Specifying Information

FIG. 13 is a view showing CO-smoke conversion coefficient-specifying information according to the embodiment. The "CO-smoke conversion coefficient-specifying information" is information to specify a CO-smoke conversion coefficient. Here, the "CO-smoke conversion coefficient" is a coefficient for converting CO data into data corresponding to smoke data, and is a first coefficient used when a multi-calculation value described below is computed. As shown in FIG. 13, the "CO-smoke conversion coefficient-specifying information" is configured to correlate the item "CO gas concentration (ppm)" and the item "CO-smoke conversion coefficient ((%/m)/ppm)" to information corresponding to each item, for example. Here, information corresponding to the item "CO gas concentration (ppm)" is information similar to information corresponding to the item "CO gas concentration (ppm)" in FIG. 4. In addition, in the item "CO-smoke conversion coefficient ((%/m)/ppm)" in FIG. 13, the item "first CO-smoke conversion coefficient" and the item "second CO-smoke conversion coefficient" are provided. Information corresponding to the item "first CO-smoke conversion coefficient" is information ("0.05", "1.5", "2.0" in FIG. 13) that specifies a candidate for the CO-smoke conversion coefficient corresponding to a range of the CO gas concentration, and specifically is the CO-smoke conversion coefficient corresponding to flaming fire. Information corresponding to the item "second CO-smoke conversion coefficient" is information ("0.1", "0.23", "0.3" in FIG. 13) that specifies a candidate for the CO-smoke conversion coefficient corresponding to a range of the CO gas concentration, and specifically is the CO-smoke conversion coefficient corresponding to fumigation fire. That is, the CO-smoke conversion coefficient-specifying information includes, for example, information indicating a range of the CO gas concentration (corresponding to "less than 30 (ppm)", "30 (ppm) or more to less than 60 (ppm)", and "60 (ppm) or more" in FIG. 13, for example), as well as information indicating the first CO-smoke conversion coefficient corresponding to the range (corresponding to "0.05", "1.5", "2.0" in FIG. 13, for example), and information indicating the second CO-smoke conversion coefficient (corresponding to "0.1", "0.23", "0.3" in FIG. 13, for example). Note that the "first CO-smoke conversion coefficient" and the "second CO-smoke conversion coefficient" are coefficient s that become a candidates for the "CO-smoke conversion coefficient" used to correct smoke data, and the smoke data is corrected using any one of them. The example of FIG. 13 shows that the first CO-smoke conversion coefficient and the second CO-smoke conversion coefficient corresponding to "less than 30 (ppm)" as a range of the CO gas concentration is "0.05", and "0.1", respectively, that the first CO-smoke conversion coefficient and the second CO-smoke conversion coefficient corresponding to "30 (ppm) or more to less than 60 (ppm)" is "1.5", and "0.23", respectively, and that the first CO-smoke conversion coefficient and the second CO-smoke conversion coefficient corresponding to "60 (ppm) or more" is "2.0", and "0.3", respectively.

The CO-smoke conversion coefficient-specifying information is created by applying the method of creating CO-smoke conversion coefficient-specifying information in the embodiment 1 to the first relation information and the second relation information shown in FIG. 9. Specifically, the first CO-smoke conversion coefficient is acquired by applying the creation method of the embodiment 1 to the first relation information in FIG. 9, and the second CO-smoke conversion coefficient is acquired by applying the creation method of the embodiment 1 to the second relation information in FIG. 9. Then, CO-smoke conversion coefficient-specifying information including the acquired first CO-smoke conversion coefficient and second CO-smoke conversion coefficient is created and stored in the storage unit 273A by way of a predetermined input means (not shown) of the detector 1A.

Configuration—Second Sensitivity Coefficient Information

FIG. 14 is a view showing second sensitivity coefficient information according to the embodiment. The second sensitivity coefficient information is information to specify a second sensitivity coefficient. Here, a "second sensitivity coefficient" is a coefficient for adjusting the detection sensitivity of fire occurrence in the detector 1A, and is a second coefficient used in computing a multi-calculation value described below. In the second sensitivity coefficient information, the second sensitivity coefficient ("1.0", "1,2", or the like in FIG. 14) is associated with a temperature difference ΔT between the external temperature and the internal temperature of the detector 1A and the external temperature of the detector 1A To. In the case of FIG. 14, "1.6" on the lower right of the page, for example, indicates that the second sensitivity coefficient is "1.6" when the external temperature to of the detector 1A is "80.0 (° C.) or higher" and the temperature difference ΔT is "20.5 (° C.) or higher". Then, the second sensitivity coefficient being "1.0" in each value of the second sensitivity coefficient substantially corresponds to the fact that a temperature correction B3 described below is not performed, and the second sensitivity coefficient being greater than "1.0" substantially corresponds to the fact that the temperature correction B3 is performed. Note that "second sensitivity coefficient information" is created based on a predetermine experiment related to a relation between the temperature outside and inside the detector 1A and fire occurrence, and is stored in the storage unit 273A by way of a predetermined input means (not shown) of the detector 1A.

Turning back to FIG. 12, the acquisition unit 275A is an acquisition means configured to acquire the CO-smoke conversion coefficient and the second sensitivity coefficient. The acquisition unit 275A acquires the CO-smoke conversion coefficient and the second sensitivity coefficient based on CO data outputted from the AD conversion unit 272, each of the temperature data outputted from the AD conversion unit 271A, and the CO-smoke conversion coefficient-specifying information and the second sensitivity coefficient information stored in the storage unit 273A. Note that specific processing by the acquisition unit 275A is described below.

The determination unit 276A is a determination means configured to determine whether fire has occurred in the monitored area. The determination unit 276A computes a multi-calculation value based on the smoke data outputted from the AD conversion unit 271 or the like, compares the computed multi-calculation value with a determination threshold, and determines based on a comparison result the whether fire has occurred in the monitored area, similar to the determination unit 276 in the embodiment 1. Note that specific processing by the determination unit 276A is described below.

Processing

Figure 15:
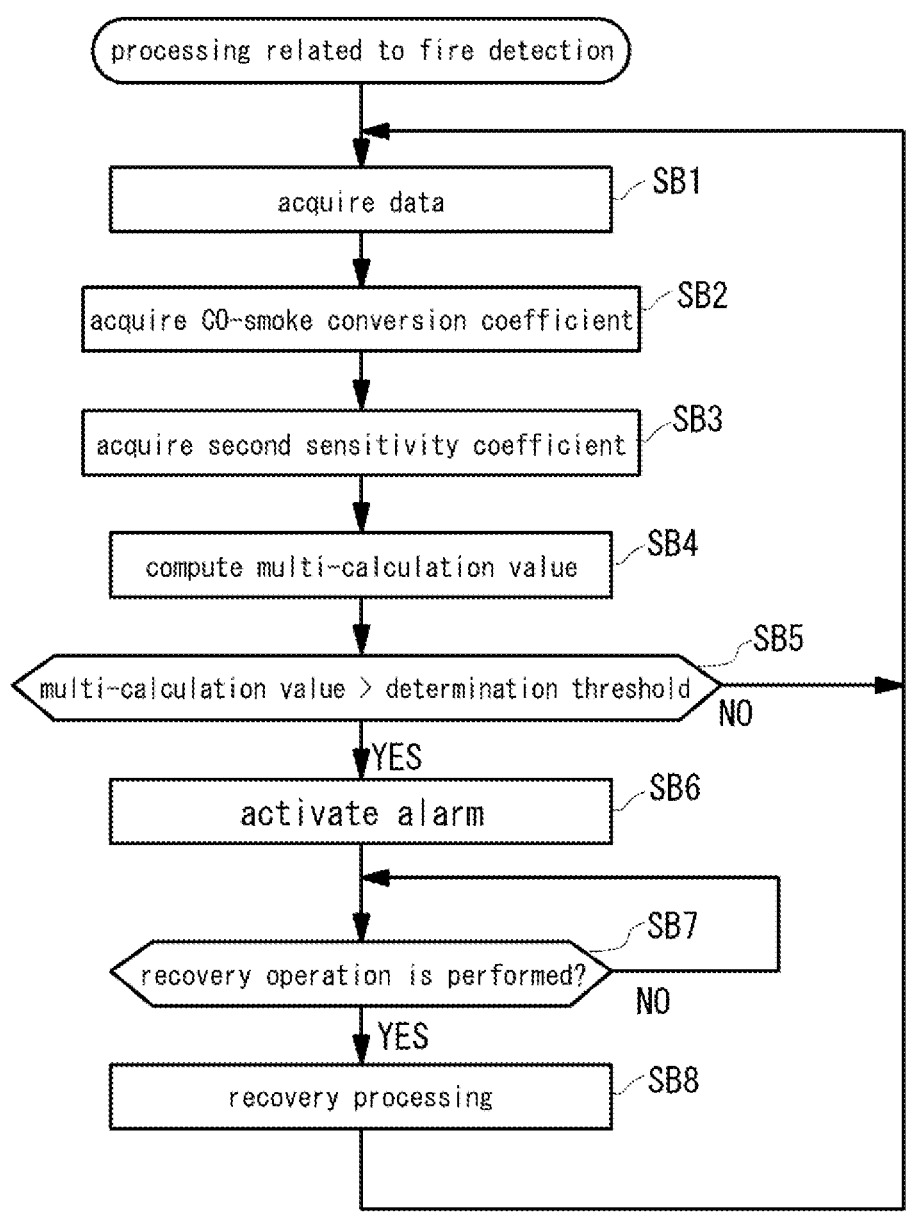
FIG. 15 is a flow chart of processing related to detection of fire.

Processing related to the fire detection performed by the detector 1A which is thus configured is described hereinafter. FIG. 15 is a flow chart of the processing related to detection of fire according to the embodiment. Note that an overall overview of the processing is first described, and then details of each processing are described appropriately.

Processing—Overview

Processing related to fire detection is started by, for example, installing the detector 1A in the monitored area, connecting the detector 1A through a detector line of a receiver to cause it to carry currents in order to bring the detector 1A into a monitoring state. The processing circuit 27A (FIG. 12) first receives a smoke detection signal E1, a CO detection signal E2, an external temperature detection signal E3, and an internal temperature detection signal E4, and acquires smoke data, CO data, and external temperature data, and internal temperature data corresponding to the received signals (SB1). Then, the acquisition unit 275A acquires a CO-smoke conversion coefficient based on the CO data and the external temperature data acquired in SB1, and CO-smoke conversion coefficient-specifying information stored in the storage unit 273A (SB2). Then, the acquisition unit 275A acquires a second sensitivity coefficient based on the external temperature data and the internal temperature data acquired in SB1, and second sensitivity coefficient information stored in the storage unit 173A (SB3). Then, the determination unit 276A computes a multi-calculation value based on each piece of data or the like acquired in SB1, the CO-smoke conversion coefficient acquired in SB2, and the second sensitivity coefficient acquired in SB3 (SB4). Then, the processing circuit 27A performs SB5 to SB8 in FIG. 15, similar to the processing with the same name of SA4 to SA7 in FIG. 5.

Processing—Details—Processing of SB2

In SB2, specifically, the acquisition unit 275A first specifies a range of the CO gas concentration corresponding to the CO gas concentration indicated by the CO data acquired in SB1 in the CO-smoke conversion coefficient-specifying information, and selects a first CO-smoke conversion coefficient and a second CO-smoke conversion coefficient corresponding to the specified range of CO gas concentration as a candidate for the CO-smoke conversion coefficient. Then, the acquisition unit 275A specifies external temperature from the external temperature data acquired in SB1, compares the specified external temperature with a predetermined temperature threshold described below, and acquires one coefficient of the first conversion coefficient and the second conversion coefficient that are selected as the above-mentioned candidate for the CO-smoke conversion coefficient as a CO-smoke conversion coefficient. As for the acquisition of the one coefficient, more specifically, if the above-mentioned specified external temperature is higher than the predetermined temperature threshold, for example, the acquisition unit 275A determines that the fire that has occurred is flaming fire, and acquires the first CO-smoke conversion coefficient as a CO-smoke conversion coefficient. On the one hand, if the above-mentioned specified external temperature is lower than the predetermined temperature threshold, for example, the acquisition unit 275A determines that the fire that has occurred is fumigation fire, and acquires the second CO-smoke conversion coefficient as a CO-smoke conversion coefficient.

The "predetermined temperature threshold" is a threshold for determining a type of fire that has occurred, and is a second threshold used as a criterion for determining whether fire that has occurred is flaming fire or fumigation fire, for example. The predetermined temperature threshold may be defined experimentally based on a fire test or the like, for example, or may be defined based on a simulation conducted according to predetermined rules.

In FIG. 13, a description is provided on the assumption that a predetermined temperature threshold is set to 70 (° C.), for example. First, similar to the acquisition unit 275 in the embodiment 1, the acquisition unit 275A specifies a range of the CO gas concentration corresponding to the CO gas concentration, and after this, selects the first CO-smoke conversion coefficient (for example, "1.5") and the second CO-smoke conversion coefficient (for example, "0.23") corresponding to the specified range of CO gas concentration as a candidate for a CO-smoke conversion coefficient. Then, for example, if the external temperature data acquired in SB1 is higher than 70(° C.), which is the predetermined temperature threshold, the acquisition unit 275A determines that the fire that has occurred is flaming fire, and acquires "1.5" as a CO-smoke conversion coefficient. On the one hand, for example, if the external temperature data acquired in SB1 is lower than 70(° C.), which is the predetermined temperature threshold, the acquisition unit 275A determines that the fire that has occurred is fumigation fire, and acquires "0.23" as a CO-smoke conversion coefficient.

Processing—Details—Processing of SB3

In SB3 in FIG. 15, specifically, the acquisition unit 275A first specifies the internal temperature of the detector 1A and the external temperature of the detector 1A from each piece of temperature data acquired in SB1. Then, the acquisition unit 275A computes a temperature difference between the specified temperatures and acquires a second sensitivity coefficient corresponding to the computed temperature difference and the above-mentioned specified external temperature from the second sensitivity coefficient information (FIG. 14) stored in the storage unit 273A.

For example, in FIG. 14, if the external temperature specified based on the data acquired in SB1 is "55(° C.)" and the internal temperature is "30(° C.)", the acquisition unit 275A computes a temperature difference "25(° C.)", and acquires "1.4" in the rightmost column on the page of FIG. 14 that corresponds to the computed temperature difference "25(° C.)" and the above-mentioned specified external temperature "55(° C.)" as a second sensitivity coefficient.

Processing—Details—Processing of SB4

Figure 16:
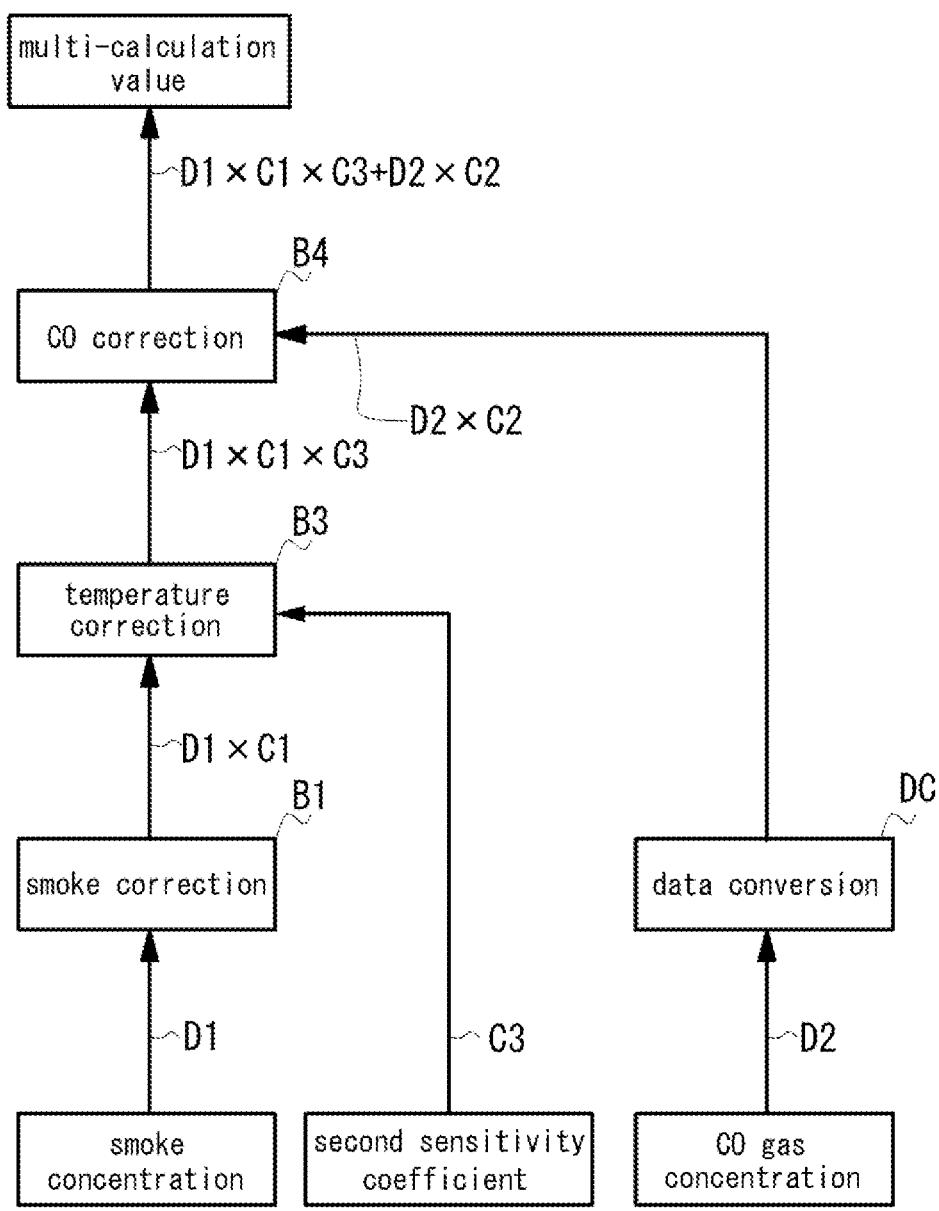
FIG. 16 is a view showing arithmetic processing performed in a determination unit.

In SB4 in FIG. 15, specifically, the determination unit 276A computes a multi-calculation value by performing the smoke correction B1 in the embodiment 1, the temperature correction B3 described below, and a CO correction B4 based on a conversion result of data conversion DC described below on the smoke concentration indicated by the smoke data outputted from the AD conversion unit 271. FIG. 16 is a view showing arithmetic processing performed in a determination unit according to the embodiment.

The temperature correction B3 is a correction for the smoke concentration indicated by the smoke data and is performed to improve the detection sensitivity of fire occurrence of the detector 1A itself. Specifically, the determination unit 276A performs the temperature correction B3 by multiplying a value after being corrected in the smoke correction B1 by the second sensitivity coefficient acquired by the acquisition unit 275A. Since a value of 1 or higher is set, as shown in FIG. 14, as the second sensitivity coefficient used in the temperature correction B3, a multi-calculation value can be increased promptly if fire occurs, and thus occurrence of the fire can be detected promptly and reliably.

The CO correction B4 is a correction for the smoke concentration indicated by the smoke data, and is performed to improve the detection sensitivity of fire occurrence of the detector 1A itself. Specifically, the determination unit 276A performs the CO correction B4 by adding the value after being converted in the data conversion DC as described in the embodiment 1 to a value after being corrected in the temperature correction B3. Since a multi-calculation value can be promptly increased if fire occurs by performing the CO correction B4, fire occurrence can be detected promptly and reliably.

A case in which the second sensitivity coefficient acquired by the acquisition unit 275A in SB3 in FIG. 15 is "C3" is described with reference to FIG. 16. Note that "D1", "D2", "C1", and "C2" in FIG. 16 are similar to those in FIG. 6. The determination unit 276A performs the temperature correction B3 by multiplying "D1×C1" as a correction result of the smoke correction B1 by "C3" and computes "D1×C1×C3" as a correction result of the temperature correction B3. Then, the determination unit 276A performs the CO correction B4 by adding "D2×C2" which is a conversion result of the DC conversion to "D1×C1×C3" which is the correction result of the temperature correction B3, and computes "D1×C1×C3+ D2×C2" as a correction result of the CO correction B4, that is, as a multi-calculation value.

Effect of the Embodiment 2

As such, according to the embodiment, since the CO-smoke conversion coefficient corresponding to the type of fire can be acquired based on a detection result of the temperature sensor 30, the CO-smoke conversion coefficient that is suitable for fire occurring in the monitored area can be reflected in a determination of whether fire has occurred. Thus, occurrence of an abnormality in the monitored area can be detected promptly and reliably.

In addition, since the CO-smoke conversion coefficient corresponding to flaming fire or fumigation fire that is occurring in the monitored area can be acquired, a CO-smoke conversion coefficient suitable for flaming fire or fumigation fire that is occurring in the monitored area can be reflected in the determination of whether fire has occurred. Thus, occurrence of an abnormality in the monitored area can be detected promptly and reliably.

In addition, since a second sensitivity coefficient is acquired based on second sensitivity coefficient information, a multi-calculation value is acquired based on the acquired second sensitivity coefficient and CO-smoke conversion coefficient, and the determination of whether an abnormality has occurred can be made based on the acquired multi-calculation value, occurrence of an abnormality in the monitored area can be detected promptly and reliably.

In addition, since it is possible to determine whether fire has occurred in the monitored area by using the multi-calculation value obtained by reflecting the CO-smoke conversion coefficient, the CO gas concentration indicated by the CO data, and the second sensitivity coefficient to the smoke concentration indicated by the smoke data, fire occurrence in the monitored area can be detected promptly and reliably.

Embodiment 3

An embodiment 3 is described hereinafter. The embodiment 3 is an embodiment in a case in which a determination of whether an abnormality has occurred is made based on a detection value of a smoke sensor, a detection value of a CO sensor, a first coefficient, and a determination threshold, and in a predetermined case, the determination is made by considering a hold value as a detection value of the CO sensor. Note that a configuration of the embodiment 3 is substantially identical to that of the embodiment 1, unless otherwise specified. Any configuration which is substantially identical to that of the embodiment 1 is assigned with same symbols as those used in the embodiment 1 if needed, and a description thereof is omitted.

Configuration

Figure 17:
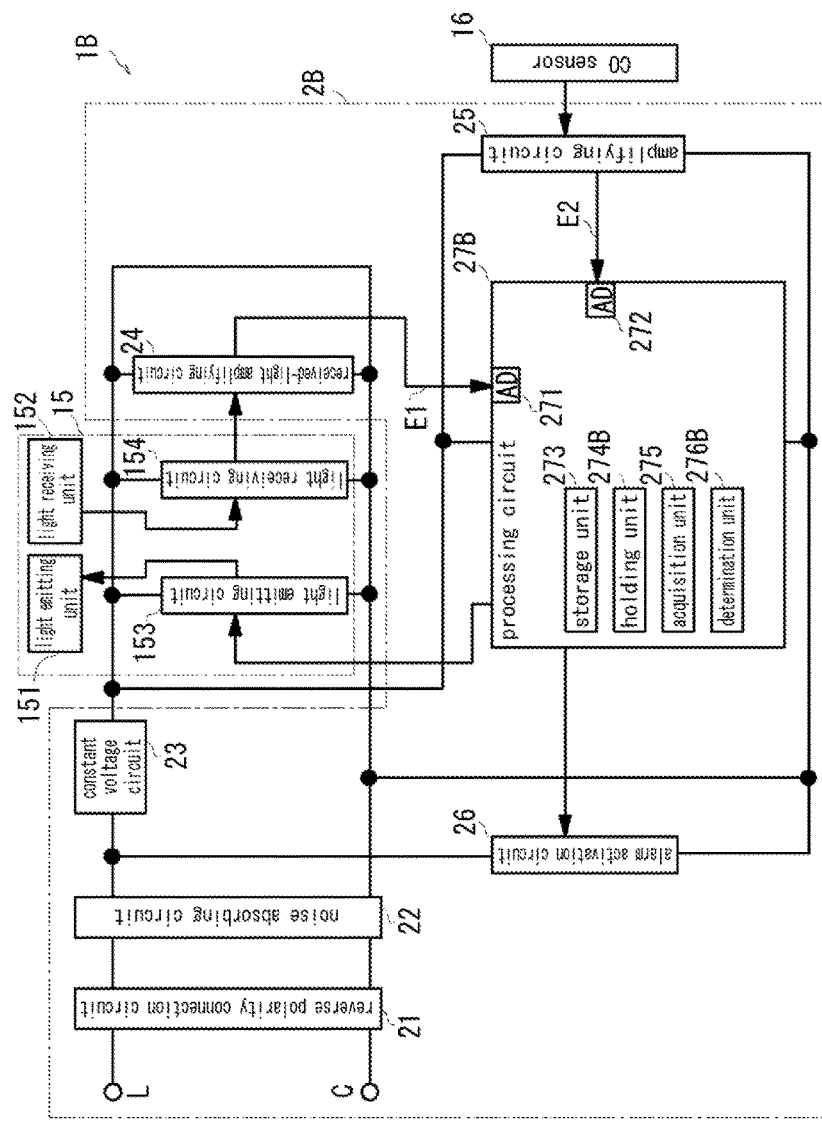
FIG. 17 is a block diagram of a detector circuit according to an embodiment 3.

First, since a detector according to the embodiment has same appearance as the detector in the embodiment 1, only an electric configuration of the detector is described. FIG. 17 is a block diagram of a detector circuit according to the embodiment.

As shown in FIG. 17, a detector 1B is equipped with a smoke sensor 15, a CO sensor 16, and a detector circuit 2B.

Configuration—Detector Circuit

The detector circuit 2B is an electric circuit mounted on a circuit board of the detector 1B and connected to a detector line (not shown) drawn out of a receiver (not shown) by way of a terminal L and a terminal C which are provided in the detector 1B. The detector circuit 2B has a reverse polarity connection circuit 21, a noise absorbing circuit 22, a constant voltage circuit 23, a received-light amplifying circuit 24, an amplifying circuit 25, an alarm activation circuit 26, and a processing circuit 27B.

Configuration—Detector Circuit—Processing Circuit

The processing circuit 27B has AD conversion units 271, 272, a storage unit 273, a holding unit 274B, an acquisition unit 275, and a determination unit 276B in terms of a functional concept.

The holding unit 274B is a holding means configured to hold a hold value. The holding unit 274B appropriately holds the hold value based on CO data outputted from the AD conversion unit 272. Note that specific processing by the holding unit 274B is described below.

The determination unit 276B is a determination means configured to determine whether fire has occurred in the monitored area. The determination unit 276B computes a multi-calculation value based on the smoke data outputted from the AD conversion unit 271 or the like, compares the computed multi-calculation value with a determination threshold, and determines whether fire has occurred in the monitored area based on a comparison result. Note that specific processing by the determination unit 276B is described below.

Processing

Figure 18:
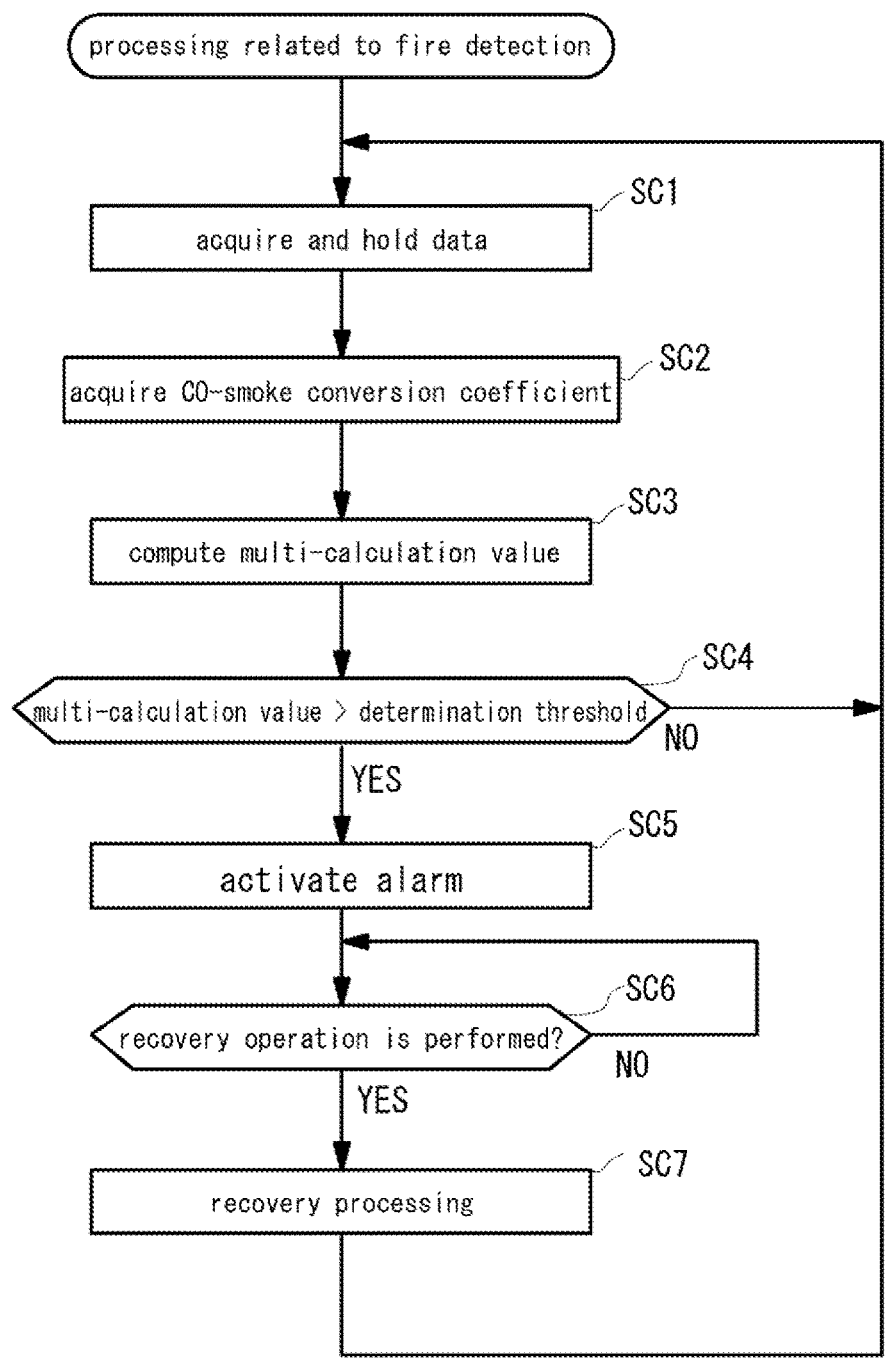
FIG. 18 is a flow chart related to detection of fire.

Processing related to the fire detection performed by the detector 1B which is thus configured is described hereinafter. FIG. 18 is a flow chart of processing related to detection of fire according to the embodiment. Note that an overall overview of the processing is described, and then details of each processing are described appropriately.

Processing—Overview

Processing related to fire detection is started by, for example, installing the detector 1B in the monitored area, connecting the detector 1B through a detector line of a receiver to cause it to carry currents in order to bring the detector 1B into a monitoring state. The processing circuit 27B (FIG. 17) first receives a smoke detection signal E1 and a CO detection signal E2, and acquires smoke data and CO data corresponding to the received signals (SC1). In this case, the holding unit 274B appropriately holds a hold value based on the acquired CO data. Then, similar to SA2 in FIG. 5, the acquisition unit 275 acquires a CO-smoke conversion coefficient based on the CO data acquired in SC1 in FIG. 18 and the CO-smoke conversion coefficient-specifying information (FIG. 4) stored in the storage unit 273 (SC2). Then, the determination unit 276B computes a multi-calculation value (SC3) based on each piece of data or the like acquired in SC1 and the CO-smoke conversion coefficient acquired in SC2. Then, similar to SA4 in FIG. 5, the determination unit 276B compares the multi-calculation value computed in SC3 with a determination threshold for determining whether fire has occurred in the monitored area (SC4) based on a comparison result. Then, based on a determination result in SC4, the processing circuit 27B performs processing of SC1 to SC3 in FIG. 18 again, similar to the processing of SA4 onwards in FIG. 5 with same names or each processing of SC5 to SC7 in FIG. 18 described below.

Processing—Details—Processing of SC1

In SC1, specifically, the holding unit 274B repeatedly performs a comparison of the CO gas concentration indicated by the CO gas outputted from the AD conversion unit 272 (hereinafter also referred to as "CO gas concentration indicated by the CO data") with predetermined threshold concentration described below in a relatively short time interval. Then, if the CO gas concentration indicated by the CO data falls below the predetermined threshold concentration after the CO gas concentration indicated by the CO data exceeds the predetermined threshold concentration, the holding unit 274B determines that the case is a "predetermined case". Then, if the holding unit 274B determines to be in the "predetermined case", it holds a predetermined value as a hold value during hold time, described below. On the one hand, if the holding unit 274B does not determine to be in a "predetermined case", it does not hold a hold value.

The "predetermined case" refers to a case in which a monitored area enters the predefined state. It corresponds to a case, for example, in which the CO gas concentration around the detector 1B temporarily drops when the CO gas concentration around the detector 1B has risen due to fire in the monitored area, or the like. In addition, the "predetermined threshold concentration" is predetermined concentration of predefined carbon monoxide, and is, for example, the concentration that is higher than the carbon monoxide concentration in the natural world in the case in which no fire has occurred. In addition, the "predetermined threshold concentration" is set by a manufacturer or a user or the like of the detector 1B. The predetermined threshold concentration may be set to approximately 30 (ppm), for example.

The "predetermined value" is a predefined value and stored in the storage unit 273, for example. In addition, the "predetermined value" is a value corresponding to the predetermined threshold concentration described above (that is, for example, a value that matches the "predetermined threshold concentration" or the like), and is set in advance as a fixed value by the manufacturer or user of the detector 1B. In addition, the configuration for the predetermined value makes it possible to predefine the hold value held by the holding unit 274B. Thus, fire can be promptly detected and frequency of occurrence of non-fire alarms can be reduced even in the predetermined case by predefining the operation of the detector 1B in the predetermined case.

"Holding time" is a period of time during which the holding unit 274B holds a hold value. For example, the "holding time" corresponds to a period of time from when the CO gas concentration indicated by the CO data falls below the predetermined threshold concentration after the CO gas concentration indicated by the CO data exceeds the predetermined threshold concentration until when the CO gas concentration indicated by the CO data exceeds the predetermined threshold concentration again.

Figure 19:
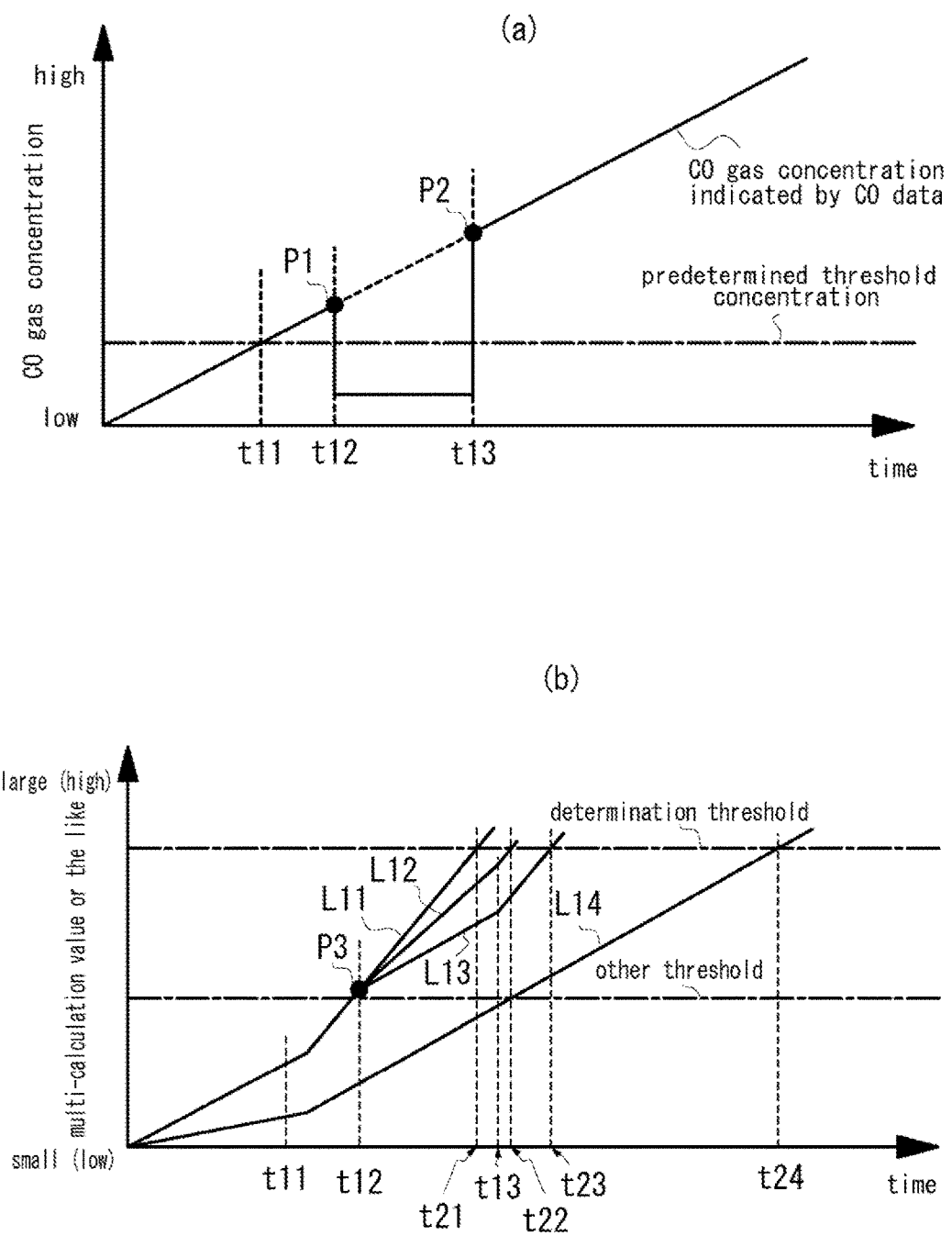
FIG. 19 is a view showing various types of data.

FIG. 19(a) is a view showing an example of the CO data according to the embodiment and a view showing the CO gas concentration indicated by the CO data at each time. In FIG. 19(a), the CO gas concentration indicated by the CO data falls below the predetermined threshold concentration at time t12 after exceeding the predetermined threshold concentration at t11, and then exceeds the predetermined threshold concentration again at time t13. In the case of FIG. 19(a), the holding unit 274B determines to be in the "predetermined case" at time t12. Then, since the holding unit 274B determines to be in the "predetermined case" at time t12, the holding unit 274B holds a predetermined value stored in the storage unit 273 as a hold value. Then, the holding unit 274B continues to hold the predetermined value as a hold value until the CO gas concentration indicated by the CO data exceeds the predetermined threshold concentration again at time t13. That is, in the case of FIG. 19(a), the holding unit 274B does not hold the hold value in a period of time earlier than time t12, holds the predetermined value as a hold value in a period of time from time t12 to time t13, and does not hold the hold value in a period of time later than time t13.

Processing—Details—Processing of SC3

Figure 20:
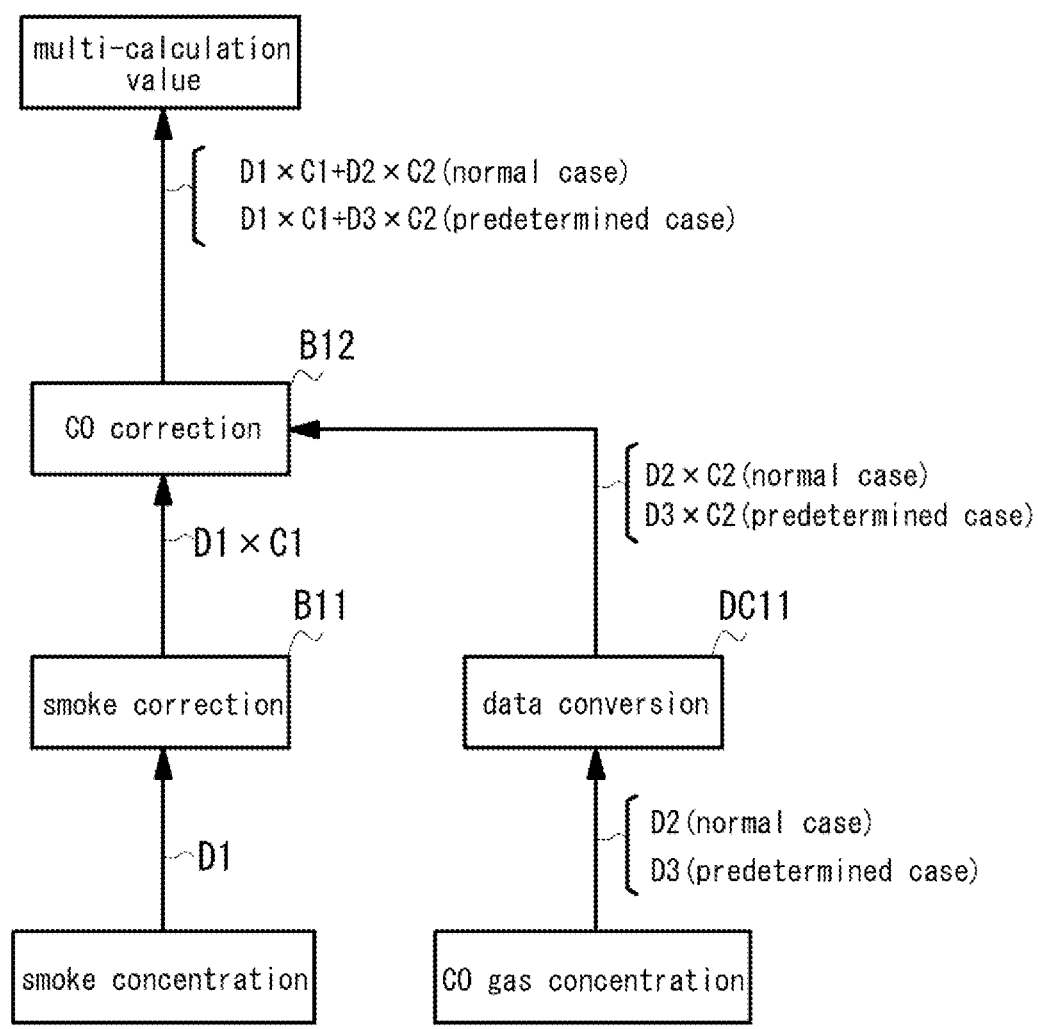
FIG. 20 is a view showing arithmetic processing performed in a determination unit.

In SC3 in FIG. 18, specifically, the determination unit 276B computes a multi-calculation value by performing a smoke correction B11 described below and a CO correction B12 based on a conversion result of data conversion DC on the smoke concentration indicated by the smoke data outputted from the AD conversion unit 271 (hereinafter also referred to as "smoke concentration indicated by the smoke data"). FIG. 20 is a view showing arithmetic processing performed in the determination unit according to the embodiment.

The smoke correction B11 is a correction for the smoke concentration indicated by the smoke data, and performed to reduce the detection sensitivity of fire occurrence to the smoke concentration in the detector 1B. Specifically, the determination unit 276B performs the smoke correction B11 by multiplying the smoke concentration indicated by the smoke data by a first sensitivity coefficient. Here, the "first sensitivity coefficient" is a coefficient for adjusting the detection sensitivity of fire occurrence in the detector 1B and is a coefficient used when the determination unit 276B computes the multi-calculation value. The "first sensitivity coefficient" is set to a number equal to or smaller than 1 so that a value after the smoke correction B11 is performed is a value equal to or smaller than a value before the smoke correction B11 is performed. Then, if the smoke correction B11 is performed using a value less than 1 as the first sensitivity coefficient, it becomes possible to reduce occurrence frequency of non-fire alarms in the detector 1B because the fire detection sensitivity based on smoke can be reduced.

The data conversion DC11 refers to a conversion of the CO data into the data corresponding to the smoke data and is performed to create the data used in CO correction B12 described below. Specifically, the determination unit 276B performs the data conversion DC11 on the hold value held by the holding unit 274B or the CO gas concentration indicated by the CO data, based on whether or not the holding unit 274 holds the hold value. For example, if the holding unit 274B holds the hold value, the determination unit 276B considers the hold value held by the holding unit 274B as the CO gas concentration indicated by the CO data, and performs the data conversion DC11 by multiplying the hold value by the CO-smoke conversion coefficient acquired in SC2 in FIG. 18. On the one hand, for example, if the holding unit 274B does not hold a hold value, the determination unit 276B performs the data conversion DC11 by multiplying the CO gas concentration indicated by the CO data by the CO-smoke conversion coefficient acquired in SC2 in FIG. 18. Note that, since flag information indicating whether or not the holding unit 274B holds the hold value is stored in the storage unit 273, it can be determined whether or not the holding unit 274B holds the hold value by referring to the flag information.

Turning back to FIG. 20, the CO correction B12 is a correction for the smoke concentration indicated by the smoke data, and is performed to improve the detection sensitivity of fire occurrence of the detector 1B itself. Specifically, the determination unit 276B performs the CO correction B12 by adding a value after conversion of the data conversion DC11 to a value after correction of the smoke correction B11. As described below, since the multi-calculation value can be promptly increased if fire occurs by performing the CO correction B12, fire occurrence can be detected promptly and reliably.

An example of computing the multi-calculation value is described with reference to FIG. 20. Here, on the assumption that the smoke concentration indicated by the smoke data acquired in SC1 in FIG. 18 is "D1", the CO gas concentration indicated by the CO data acquired in SC1 in FIG. 18 is "D2", a hold value held by the holding unit 274B if it determined to be in a "predetermined case" in SC1 in FIG. 18 is "D3", the CO-smoke conversion coefficient acquired by the acquisition unit 275 in SC2 in FIG. 18 is "C2", and a first sensitivity coefficient is "C1", a case in which the holding unit 274B does not hold the hold value (corresponding to the "normal case" in FIG. 20) and a case in which the holding unit 274B holds the hold value (corresponding to the "predetermined case" in FIG. 20) are described.

In FIG. 20, if the holding unit 274B does not hold the hold value, the determination unit 276B performs the smoke correction B11 by multiplying "D1" by "C1" and computes "D1×C1" as a correction result of the smoke correction B11. Then, the determination unit 276B performs the data conversion DC11 by multiplying "D2" by "C2" and computes "D2×C2" as a conversion result of the data conversion DC11. Then, the determination unit 276B performs the CO correction B12 by adding "D2×C2" to "D1×C1" and computes "D1×C1+D2×C2" as a correction result of the CO correction B12, that is to say, the multi-calculation value.

In FIG. 20, if the holding unit 274B holds the hold value, similar to a normal case, the determination unit 276B computes "D1×C1" as a correction result of the smoke correction B11. Then, the determination unit 276B performs the data conversion DC11 by multiplying "D3" by "C2" and computes "D3×C2" as a conversion result of the data conversion DC11. Then, the determination unit 276B performs the CO correction B12 by adding "D3×C2" to "D1×C1" and computes "D1×C1+D3×C2" as a correction result of the CO correction B12, that is, the multi-calculation value.

Processing—Details—Processing of SC4

In SC4 in FIG. 18, the determination unit 276B determines whether fire has occurred in the monitored area, similar to SA4 in FIG. 5. In the determination of fire, because the multi-calculation value is used, it becomes possible to perform detection of fire occurrence promptly and reliably, as described below, by reflecting the CO gas concentration as a fire-related element in the determination, in addition to the smoke concentration as the fire-related element.

Here, a reason why the detector 1B can detect fire occurrence promptly and reliably is described based on a relation with the fire-related element.

In the case of the detector 1B, as described above, it is possible to reflect the smoke concentration as a fire-related element along with the CO gas concentration as the element in the multi-calculation value, by performing the CO correction B12 in FIG. 20. In addition, as described above, in the case of the detector 1B, the hold value of the holding unit 274B can be appropriately used when computing the multi-calculation value. Therefore, detection of fire occurrence can be promptly and reliably performed by reliably reflecting the CO gas concentration in the multi-calculation value. Furthermore, in the detector 1B, since both of the smoke correction B11 and the CO correction B12 are performed, it becomes possible to promptly and reliably detect fire occurrence while reducing the occurrence frequency of non-fire alarm. In the following, these are described more specifically.

For example, FIG. 19(b) is a view showing the multi-calculation value or the like at each time. Note that the horizontal axis of FIG. 19(b) corresponds to the horizontal axis of FIG. 19(a).

A line segment L11 represents the multi-calculation value of the detector 1B when the case is not the "predetermined case". Specifically, the line segment L11 represents the multi-calculation value when the smoke concentration indicated by the smoke data continues to rise, and as shown by a straight upward line on the page which includes a dashed line between a point P1 and a point P2 in FIG. 19(a), when the CO gas concentration indicated by the CO data exceeds a predetermined threshold and then never falls below the predetermined threshold (also referred to as "when the CO gas concentration continuously increases). That is, the line segment L11 represents the multi-calculation value when both of the smoke concentration indicated by the smoke data and the CO gas concentration indicated by the CO data continue to rise.

In addition, a line segment L12 in FIG. 19(b) represents the multi-calculation value of the detector 1B when the case is the "predetermined case" for some time. Specifically, the line L12 represents the multi-calculation value when the smoke concentration indicated by the smoke data continues to rise, and as shown by a polygonal line shown in a solid line in FIG. 19(a), when the CO gas concentration indicated by the CO data falls below the predetermined threshold concentration for some time (from time t12 to time t13) (also referred to as "when the CO gas concentration temporarily decreases"). That is, the line segment L12 represents the multi-calculation value when the CO gas concentration indicated by the CO data decreases for some time although the smoke concentration indicated by the smoke data continues to rise. Note that a line segment L13 and a line segment L14 are described below.

When the CO gas concentration continuously increases (that is, when it corresponds to the line L11), the holding unit 274B does not hold a hold value for an entire period of time. Therefore, the determination unit 276B computes a value corresponding to "D1×C1+D2×C2" in FIG. 20 as the multi-calculation value for the entire period of time. Then, the determination unit 276B determines that no fire has occurred in a period of time earlier than time t21 and that fire has occurred at time t21.

When the CO gas concentration temporarily decreases (that is, when it corresponds to the line segment L12), the holding unit 274B does not hold a hold value in a period of time earlier than time t12, holds the predetermined value as a hold value for a period of time from time t12 to time t13, and does not hold a hold value in a period of time later than time t13. Therefore, the determination unit 276B computes a value corresponding to "D1×C1+D2×C2" in FIG. 20 as the multi-calculation value in a period of time earlier than t12 and later than time t13, and computes a value corresponding to "D1×C1+D3×C2" in FIG. 20 as the multi-calculation value in a period of time from time t12 to time t13. Then, the determination unit 276B determines that fire has not occurred in a period of time earlier than time t22 in FIG. 19(b) and that fire has occurred at time t22.

Here, with reference to FIG. 19(b), detection of fire occurrence by first and second comparison target detectors described below and detection of fire occurrence by the detector 1B are described. Note that the line segments L11 to L13 to the left of a point P3 on the page are a common line segment. In addition, "other threshold" in FIG. 19(b) is shown for convenience of description and has nothing to do with the operation of the detector 1B.

The line L13 represents other multi-calculation value in the "predetermined case" for some time similar to the line L12. "Other multi-calculation value" is a calculated value shown for convenience of description, and is a calculated value when computing is performed by using the CO concentration indicated by the CO data without using a hold value in spite of being in the "predetermined case". It is similar to the multi-calculation value in the embodiment, excluding any matter specially remarked in the "other multi-calculation value". In addition, the line segment L14 represents the smoke concentration indicated by the smoke data (corresponding to "D1" in FIG. 20).

In addition, the first comparison target detector and the second comparison target detector are detectors different from the detector 1B and described for convenience of description. Specifically, the first comparison target detector is configured to detect fire occurrence using the multi-calculation value corresponding to the line segment L13, and the second comparison target detector is configured to detect fire occurrence using the smoke concentration indicated by the smoke data corresponding to the line segment L14.

As for other multi-calculation value (line segment L13), for a period of time from t12 to t13, since the hold value is not reflected although the CO gas concentration indicated by the CO data is a value lower than the predetermined threshold concentration, the slope of the line segment L13 in FIG. 19(b) is smaller than the slope of the line segment L12. Thus, the first comparison target detector detects fire occurrence at time t23 which is later than time t22. That is, the first comparison target detector may get behind the detector B1 in detection of fire occurrence.

For the smoke concentration indicated by the smoke data (for the line segment L14), because the smoke correction B11 and the CO correction B12 in FIG. 20 are not performed, a value of the line segment L14 is smaller than that of the line segment L12 at each time. Thus, the second comparison target detector detects fire occurrence at time t24 which is later than time t22 and time t23. That is, the second comparison target detector gets behind the detector 1B in detection of fire occurrence. In addition, for example, if the level of the determination threshold of FIG. 19(b) is lowered to the level of other threshold in the second comparison target detector lowers the level of determination threshold of FIG. 19(b) so that fire occurrence is detected at t22 as with the detector 1B, the occurrence frequency of "non-fire alarms" as described above may increase.

In contrast to these, the detector 1B can detect fire occurrence at time t21 or time t22 which is earlier than time t23 and time t24. Therefore, the detector 1B can detect fire occurrence earlier than the first and second comparison target detectors. In addition, since the CO-smoke conversion coefficient-specifying information (FIG. 4) that is appropriately created with a creation method example described below is reflected in detection of fire occurrence at the detector 1B, it can detect fire occurrence more promptly and reliably than the first and second comparison target detectors. Furthermore, as shown in FIG. 19(b), since the detector 1B can set the level of the determination threshold at a higher level than that of other threshold, the occurrence frequency of "non-fire alarms" can be made lower than that at the first and second comparison target detectors.

Effect of the Embodiment 3

As such, according to this embodiment, a CO-smoke conversion coefficient corresponding to the CO gas concentration and the smoke concentration can be reflected in a determination of whether an abnormality has occurred, irrespective of magnitude of a detection value of the smoke sensor 15 and that of the CO sensor 16. Furthermore, if the holding unit 274B determines that the case is the "predetermined case", it is possible to determine whether an abnormality has occurred, considering that the hold value held by the holding unit 274B is the CO gas concentration indicated by the CO data. Thus, occurrence of an abnormality in the monitored area can be detected promptly and reliably. Therefore, for example, even if fire has occurred in which an amount of CO gas generated is relatively small, a CO-smoke conversion coefficient can be reflected in the determination of whether fire has occurred, irrespective of the CO gas concentration. Thus, occurrence of the fire can be detected promptly and reliably. Alternatively, as in the case of fumigation fire, even when fire has occurred in which an amount of carbon monoxide gas generated is relatively large but an amount of smoke generated is extremely small, for example, a CO-smoke conversion coefficient can be reflected in the determination of whether fire has occurred, irrespective of the smoke concentration. Thus, occurrence of the fire can be detected promptly and reliably. Furthermore, in the predetermined case such as a case in which the concentration of carbon monoxide gas based on fire decreases due to an external factor such as a change in a combustion state of combustibles or wind or the like, a determination of whether fire has occurred can be made using a hold value instead of a detection value that decreases due to the external factor. Thus, any influence on the determination due to the external factor can be eliminated and occurrence of the fire can be detected promptly and reliably.

In addition, since the CO-smoke conversion coefficient can be acquired based on the detection value of the CO sensor 16 and the acquired CO-smoke conversion coefficient can be reflected in the determination of whether an abnormality has occurred, a CO-smoke conversion coefficient suitable for the environment of the monitored area can be reflected in the determination, and occurrence of the abnormality can be detected promptly and reliably.

In addition, if the holding unit 274B determines to be in the "predetermined case", the determination of whether an abnormality has occurred can be made by using the hold value instead of the CO gas concentration indicated by the CO data a value of which easily fluctuates due to an external factor such as wind or the like. Thus, any influence on the determination of fluctuations of the CO data based on the external factor such as wind or the like can be eliminated, and occurrence of an abnormality in the monitored area can be detected promptly and reliably.

In addition, if the holding unit 274B determines to be in the "predetermined case", the determination of whether an abnormality has occurred can be made based on a comparison result of the multi-calculation value as a sum of a value based on the hold value in place of the CO gas concentration indicated by the CO data and the CO-smoke conversion coefficient and a value based on the smoke concentration indicated by the smoke data with the determination threshold. Thus, any influence due to the external factor such as wind or the like can be eliminated from the multi-calculation value and occurrence of an abnormality in the monitored area can be detected promptly and reliably.

In addition, the holding unit 274B can hold a hold value based on the "predetermined threshold concentration" as a determination criterion on whether being in the "predetermined case". Thus, if the holding unit 274B determines to be in the "predetermined case", any influence on a determination at the determination unit 276B due to the external factor such as wind or the like can be reliably eliminated, and occurrence of an abnormality in the monitored area can be detected promptly and reliably.

In addition, owing to the fact that the holding unit 274B continuing to hold the hold value in a period of time from when the CO gas concentration indicated by the CO data falls below a predetermined threshold concentration after the CO gas concentration indicated by the CO data exceeds the predetermined threshold concentration until when the CO gas concentration indicated by the CO data exceeds the predetermined threshold concentration again, the determination of whether an abnormality has occurred can be made by using the hold value in place of the CO gas concentration indicated by the CO data during the period in which the CO data is influenced relatively substantially due to the external factor such as wind or the like. Thus, any influence due to the external factor can be reliably eliminated and occurrence of an abnormality in the monitored area can be detected promptly and reliably.

Embodiment 4

An embodiment 4 is described hereinafter. The embodiment 4 is an embodiment in a case in which a determination of whether an abnormality has occurred is made based on a detection value of a smoke sensor, a detection value of a CO sensor, a first coefficient, a second coefficient, and a determination threshold, and in a predetermined case, the determination is made by considering a hold value as a detection value of the CO sensor. Note that a configuration of the embodiment 4 is substantially identical to the configurations of the embodiments 1 to 3 unless otherwise specified. Any configuration which is substantially identical to the configurations of the embodiments 1 to 3 is assigned with same symbols as those used in the embodiments 1 to 3 if needed, and a description thereof is omitted.

Configuration

Figure 21:
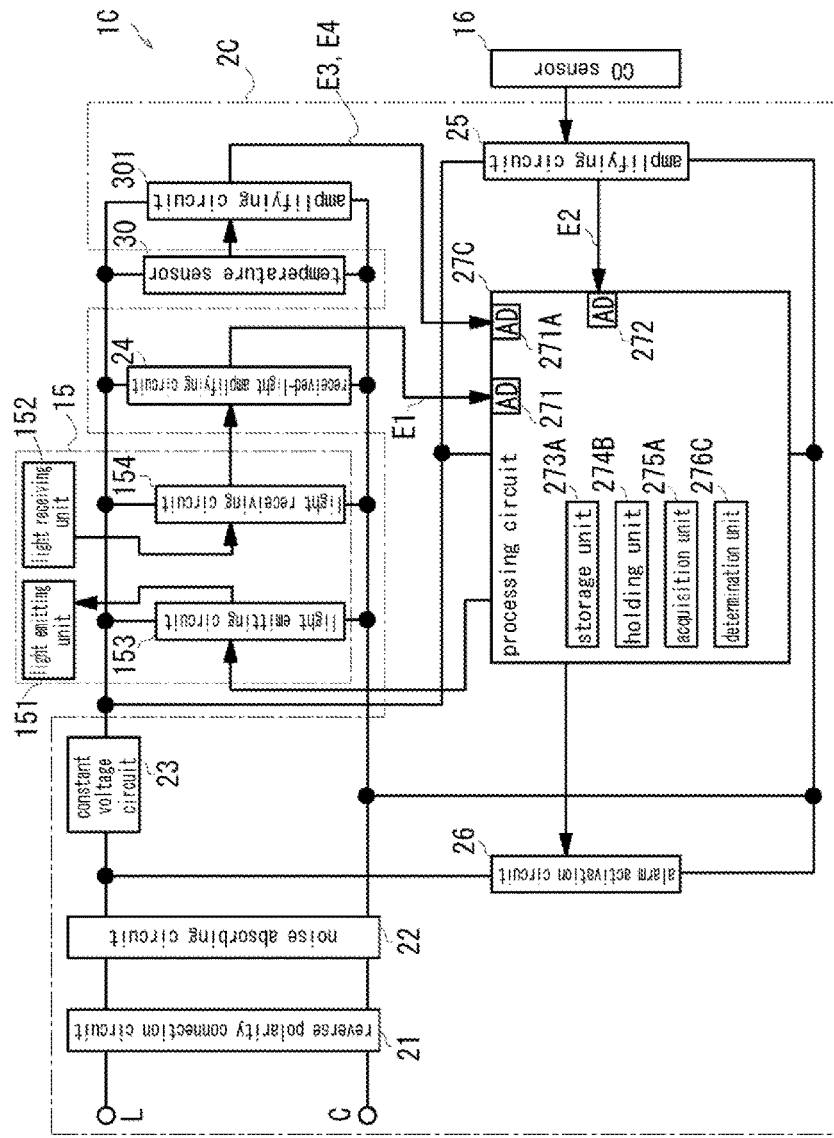
FIG. 21 is a block diagram of a detector circuit according to an embodiment 4.

First, since a detector according to the embodiment has appearance identical to that of the detector of the embodiment 2, only an electrical configuration of the detector is described. FIG. 21 is a block diagram of a detector circuit according to the embodiment.

As shown in FIG. 21, a detector 1C is equipped with a smoke sensor 15, a CO sensor 16, a temperature sensor 30, and a detector circuit 2C.

Configuration—Detector Circuit

The detector circuit 2C has a reverse polarity connection circuit 21, a noise absorbing circuit 22, a constant voltage circuit 23, a received-light amplifying circuit 24, an amplifying circuit 25, an alarm activation circuit 26, an amplifying circuit 301, and a processing circuit 27C.

Configuration—Detector Circuit—Processing Circuit

The processing circuit 27C has AD conversion units 271, 271A, 272, a storage unit 273A, a holding unit 274B, an acquisition unit 275A, and a determination unit 276C in terms of a functional concept.

The determination unit 276C is a determination means configured to determine whether fire has occurred in the monitored area. The determination unit 276C computes a multi-calculation value based on smoke data outputted from the AD conversion unit 271 or the like, compares the computed multi-calculation value with a determination threshold, and determines whether fire has occurred in the monitored area, as with the determination unit 276B in the embodiment 3. Note that specific processing by the determination unit 276C is described below.

Processing

Figure 22:
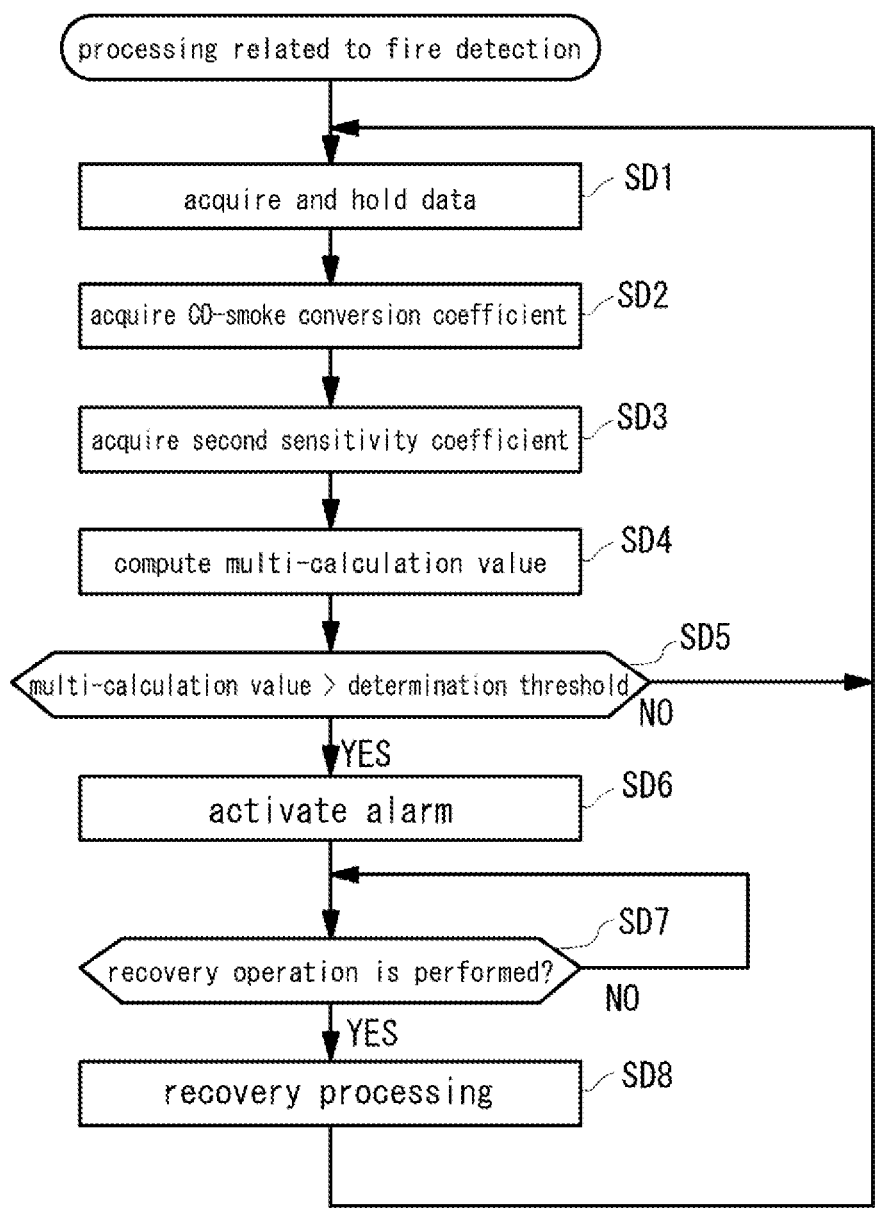
FIG. 22 is a flow chart of processing related to detection of fire.

Processing related to the fire detection performed by the detector 1C which is thus configured is described hereinafter. FIG. 22 is a flow chart of processing related to detection of fire according to the embodiment. Note that an overall overview of the processing is described, and then details of each processing are described appropriately.

Processing—Overview

Processing related to fire detection is started by, for example, installing the detector 1C in the monitored area, connecting the detector 1C through a detector line of a receiver to cause it to carry currents in order to bring the detector 1C into a monitoring state. The processing circuit 27C (FIG. 21) first receives a smoke detection signal E1, a CO detection signal E2, an external temperature detection signal E3, and an internal temperature detection signal E4, and acquires smoke data, CO data, external temperature data, and internal temperature data corresponding to the received signals (SD1). In this case, the holding unit 274B appropriately holds a hold value based on the acquired CO data. Then, similar to SB2 in FIG. 15, the acquisition unit 275A acquires a CO-smoke conversion coefficient based on the CO data acquired in SD1 in FIG. 22, the external temperature data, and the CO-smoke conversion coefficient-specifying information stored in the storage unit 273A (SD2). Then, similar to SB3 in FIG. 15, the acquisition unit 275A acquires a second sensitivity coefficient based on the external temperature data and the internal temperature data acquired in SD1 in FIG. 22 and second sensitivity coefficient information stored in the storage unit 273A (SD3). Then, the determination unit 276C computes a multi-calculation value (SD4) based on each piece of data or the like acquired in SD1, the CO-smoke conversion coefficient acquired in SD2, and the second sensitivity coefficient acquired in SD3. Then, the processing circuit 27C performs processing of SD5 to SD8 in FIG. 22, similar to the processing of SB5 to SB8 in FIG. 15 with the same names.

Processing—Details—Processing of SD4

Figure 23:
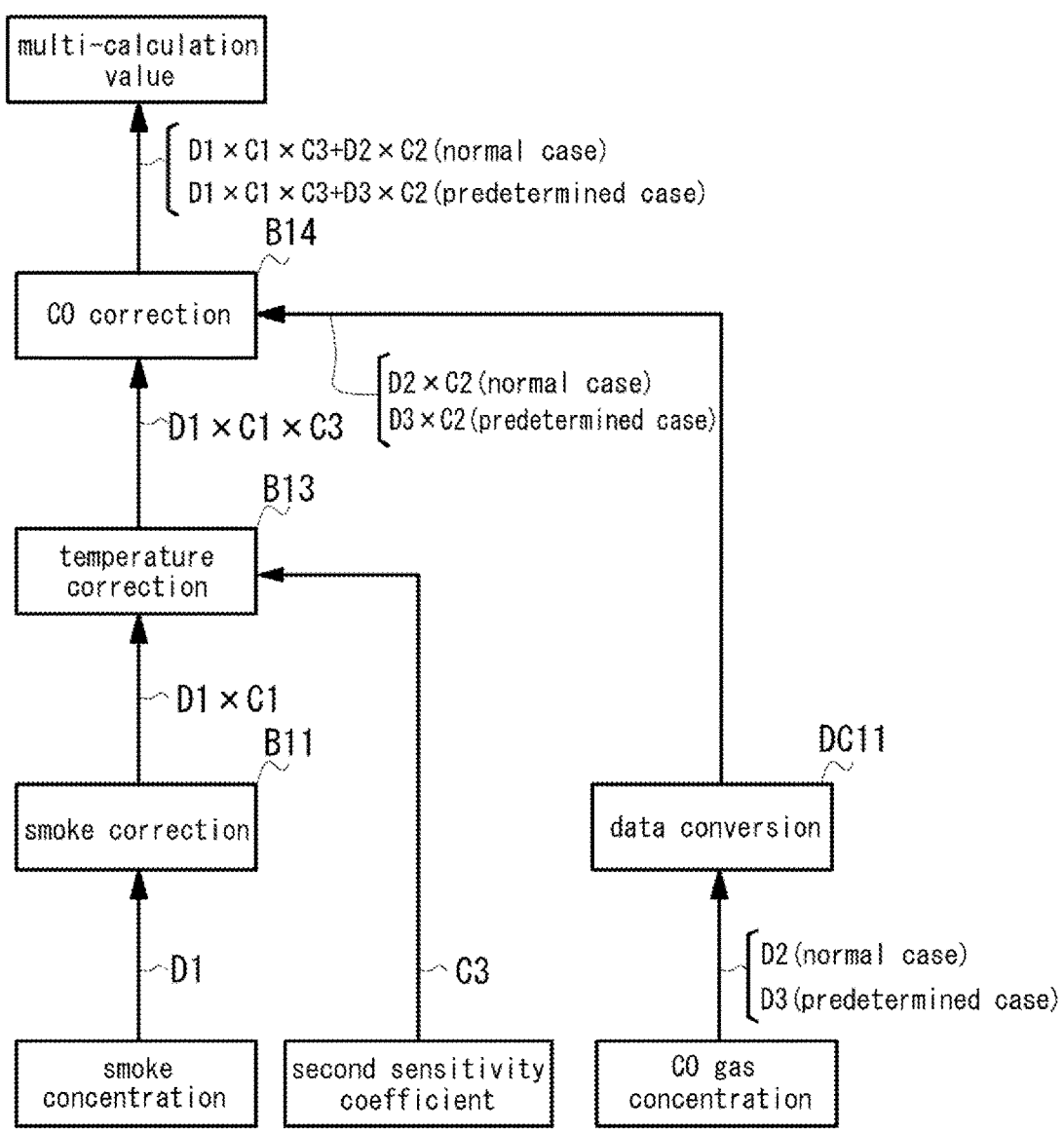
FIG. 23 is a view showing arithmetic processing performed in the determination unit.

In SD4 in FIG. 22, specifically, the determination unit 276C performs the smoke correction B11 of the embodiment 3, a temperature correction B13 described below, and CO correction B14 described below based on a conversion result of data conversion DC11 on the smoke concentration indicated by the smoke data outputted from the AD conversion unit 271 to compute the multi-calculation value. FIG. 23 is a view showing arithmetic processing performed in the determination unit according to the embodiment.

The temperature correction B13 is a correction for the smoke concentration indicated by the smoke data and is performed to improve the detection sensitivity of fire occurrence of the detector 1C itself. Specifically, the determination unit 276C performs the temperature correction B13 by multiplying a value after being corrected in the smoke correction B11 by the second sensitivity coefficient acquired by the acquisition unit 275A. Since a value of 1 or higher is set, as shown in FIG. 14, as a second sensitivity coefficient used in the temperature correction B13, the multi-calculation value can be increased promptly if fire occurs, and thus occurrence of the fire can be detected promptly and reliably.

The CO correction 14 is a correction for the smoke concentration indicated by the smoke data and is performed to improve the detection sensitivity of fire occurrence of the detector 1C itself. Specifically, the determination unit 276C performs the CO correction B14 by adding a value after being converted in the data conversion DC11 to the value after being corrected in the temperature correction B13. Since the multi-calculation value can be increased promptly by performing the CO correction B14, fire occurrence can be detected promptly and reliably.

A case in which the second sensitivity coefficient acquired by the acquisition unit 275A in SD3 in FIG. 22 is "C3" is described with reference to FIG. 23. Note that "D1", "D2", "D3", "C1", "C2", and a "predetermined case", and a "normal case" are same as those in FIG. 20. Irrespective of whether or not the holding unit 274B holds a hold value, the determination unit 276C performs the temperature correction B13 by multiplying "D1" which is the correction result of the smoke correction B11, by "C3", and computes "D1×C1×C3" as a correction result of the temperature correction B13. Then, if the holding unit 274B does not hold a hold value ("normal case" in FIG. 23), the determination unit 276C computes "D1×C1×C3+D2×C2" as the multi-calculation value. In addition, if the holding unit 274C holds a hold value ("predetermined case in FIG. 23), the determination unit 276C computes "D1×C1×C3+D3×C2" as the multi-calculation value.

Effect of the Embodiment 4

As such, according to this embodiment, a determination of whether an abnormality has occurred can be made on the basis of a CO-smoke conversion coefficient based on a fire type determined using a detection result of the temperature sensor 30 (FIG. 21) and a second sensitivity coefficient based on the detection result of the temperature sensor 30. Furthermore, if the holding unit 274B determines to be in the "predetermined case", the determination of whether an abnormality has occurred can be made by considering a hold value held by the holding unit 274B as the CO gas concentration indicated by the CO data. Thus, any influence on the determination of an external factor such as wind or the like can be eliminated and occurrence of an abnormality in a monitored are can be detected promptly and reliably.

Embodiment 5

An embodiment 5 is described hereinafter. The embodiment 5 is an embodiment in a case in which a first detector having a smoke detection unit and a second detector having a smoke detection unit and a CO detection unit respectively determine whether an abnormality has occurred with a known approach, and a receiver makes a determination using a first coefficient based on data acquired from the first detector or the second detector.

Configuration

Figure 24:
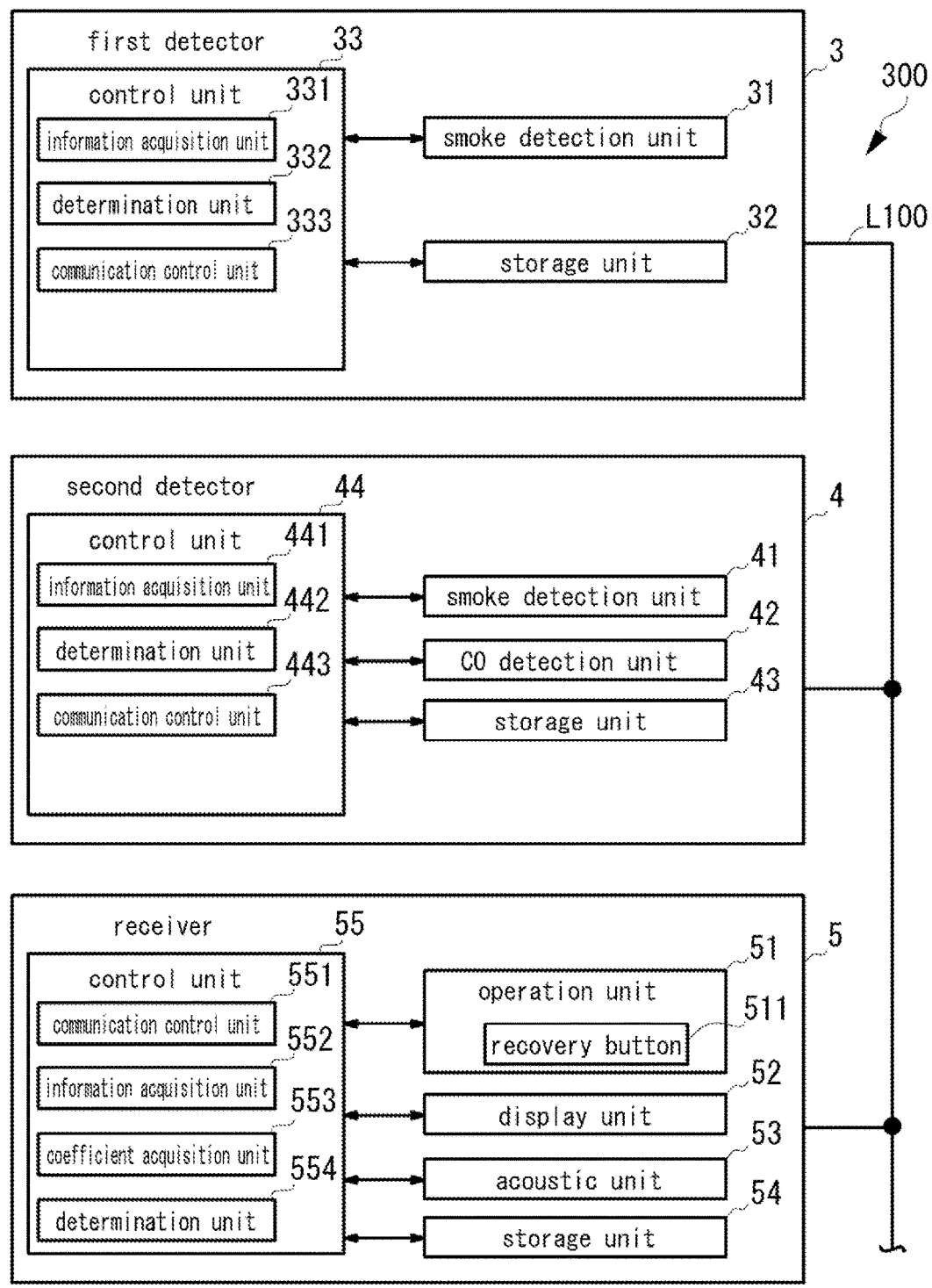
FIG. 24 is a block diagram showing a disaster prevention system according to an embodiment 5.

First, a configuration of a disaster prevention system according to the embodiment 5 is described. FIG. 24 is a block diagram showing a disaster prevention system according to the embodiment.

The disaster prevention system 300 is a system configured to prevent disaster, equipped with a first detector 3, a second detector 4, and a receiver 5, and the first detector 3, the second detector 4, and the receiver 5 are connected to communicate with each other via a communication line L100. In addition, the disaster prevention system 300 equipped with first detectors other than the first detector 3, second detectors other than the second detector 4, and receivers other than the receiver 5 depending on size of a monitored area, while the first detector 3, the second detector 4, and the receiver 5 are described hereinafter (which also applies to embodiments 6 and 7).

Configuration—First Detector

The first detector 3 is a disaster prevention means configured to detect occurrence of an abnormality in the monitored area. Specifically, it is an apparatus to detect fire as an abnormality which is installed on a ceiling or a wall in the monitored area. The first detector 3 is equipped with a smoke detection unit 31, a storage unit 32, and a control unit 33.

Configuration—First Detector—Smoke Detection Unit

The smoke detection unit 31 is a first detection means configured to detect the smoke concentration as a first physical quantity and output smoke data (first information) indicating the detected smoke concentration. While any sensor may be used as the smoke detection unit 31, a description herein is given assuming that a known light-scattering smoke sensor is used.

Configuration—First Detector—Storage Unit

The storage unit 32 is a storage means in which programs and various types of data necessary for operation of the first detector 3 are stored. Specifically, it stores identification information for uniquely identifying itself (that is, the first detector 3) (hereinafter referred to as a "first detector ID").

Configuration—First Detector—Control Unit

The control unit 33 is a control means configured to perform various types of control on the first detector 3. Specifically, it is a computer configured to comprise a CPU, various types of programs (including a basic control program such as an OS or an application program that is activated on the OS to implement specific functions) interpreted and executed on the CPU, and an internal memory, such as a RAM, for storing the programs or various types of data. Particularly, a fire detection program according to the embodiment is installed in the first detector 3 by way of any recording medium or a network so as to substantially configure each unit in the control unit 33 (which also similarly applies to control units of each of instruments described below).

The control unit 33 is equipped with an information acquisition unit 331, a determination unit 332, and a communication control unit 333 in terms of a functional concept. The information acquisition unit 331 is an information acquisition means configured to acquire information. The determination unit 332 is a determination means configured to determine whether fire has occurred in the monitored area. The communication control unit 333 is a communication control means configured to control communications. Note that processing performed by each unit in the control unit 33 is described below.

Configuration—Second Detector

The second detector 4 is also a disaster prevention detection means configured to detect occurrence of an abnormality in the monitored area. Specifically, it is an apparatus to detect fire occurrence as an abnormality which is installed on a ceiling or a wall in the monitored area. The second detector 4 is equipped with a smoke detection unit 41, a carbon monoxide detection unit (hereinafter CO detection unit) 42, a storage unit 43, and a control unit 44.

Configuration—Second Detector—Smoke Detection Unit

The smoke detection unit 41 is a first detection means configured to detect the smoke concentration as a first physical quantity and output smoke data indicating the detected smoke concentration. Its specific configuration is similar to that of the smoke detection unit 31.

Configuration—Second Detector—CO Detection Unit

The CO detection unit 42 is a second detection means configured to detect the concentration of a carbon monoxide gas (hereinafter CO gas) as a second physical quantity and output CO data (second information) indicating the detected CO gas concentration. While any sensor may be used as the smoke detection unit 42, a description herein is given assuming that a known electrochemical CO sensor is used.

Configuration—Second Detector—Storage Unit

The storage unit 43 is a storage means in which programs and various types of data necessary for operation of the second detector 4 are stored. Specifically, it stores identification information for uniquely identifying itself (that is, the second detector 4) (hereinafter referred to as a "second detector ID").

Configuration—Second Detector—Control Unit

The control unit 44 is equipped with an information acquisition unit 441, a determination unit 442, and a communication control unit 443 in terms of a functional concept. Note that a configuration of each unit in the control unit 44 is similar to that of each unit in the control unit 33 and that processing performed by each unit in the control unit 44 is described below.

Configuration—Receiver

In addition, the receiver 5 is a disaster prevention means configured to receive various types of signals and announce occurrence of an abnormality. Specifically, the receiver 5 is an apparatus configured to detect and announce fire occurrence as an abnormality which is equipped with an operation unit 51, a display unit 52, an acoustic unit 53, a storage unit 54, and a control unit 55.

Configuration—Receiver—Operation Unit

The operation unit 51 is an operation means configured to perform various operations on the receiver 5 and is specifically configured to comprise a recovery button 511. Here, the "recovery button" 511 is a button to start processing to recover the detectors from an abnormality detection state to a normal state. The "abnormality detection state" refers to a state of the detector when it has detected an abnormality, while a "normal state" refers to a state of the detector when it has not detected an abnormality.

Configuration—Receiver—Display Unit

The display unit 52 is a display means configured to display, to an operator, various types of information related to disaster prevention management in the monitored area. Specifically, it is configured to comprise an indicator light, a display or the like for displaying the various types of information.

Configuration—Receiver—Acoustic Unit

The acoustic unit 53 is an acoustic means configured to output various types of alarm sounds related to disaster prevention management in the monitored area. Specifically, it is configured to comprise a speaker or the like for outputting the various types of alarm sounds.

Configuration—Receiver—Storage Unit

The storage unit 54 is a storage means in which programs and various types of data necessary for operation of the receiver 5 are stored. Specifically, it stores identification information for uniquely identifying itself (that is, the receiver 5) (hereinafter referred to as a "receiver ID"), device-specifying information described below, and CO-smoke conversion coefficient-specifying information of FIG. 4 that is created with the creation method example described in the embodiment 1.

FIG. 25 is a view showing device-specifying information. The "device-specifying information" is information to specify a device, and specifically is information to specify the detectors included in the disaster prevention system 300. As shown in FIG. 25, this device-specifying information is configured so that the item "Detector", the item "Type", and the item "Related device" are correlated with information corresponding to each item. Here, the information corresponding to the item "Detector" is information to specify the detectors included in the disaster prevention system 300 (in FIG. 25, it is identification information, and thus it is "First detector ID" or "Second detector ID"). In addition, the information corresponding to the item "Type" is information to specify a type of the detector ("Only smoke", "Smoke and CO" in FIG. 25). Here, the "Type of detector" is a type classified on the basis of a type of a detection unit (smoke detection unit, CO detection unit or the like, for example) provided in the detector. Then, "Only smoke" in FIG. 25 specifies that the detector is provided with only the smoke detection unit from among the smoke detection unit and the CO detection unit. In addition, "Smoke and CO" specifies that the detector is provided with both the smoke detection unit and the CO detection unit. In addition, not shown in FIG. 25, "Only CO" specifies that the detector is provided with only the CO detection unit from among the smoke detection unit and the CO detection unit. In addition, the information corresponding to the item "Related device" is information to specify a related device of the detector specified by the item "Detector" (in FIG. 25, it is identification information or the like in FIG. 25, and thus it is "Second detector ID" or "None"). Here, the "related detector of a detector specified by the item "Detector"" is a related device in a case in which the multi-calculation value as described in the embodiment 1 is computed. Specifically, it is the below-mentioned other detector in a case in which in order to compute the multi-calculation value as described in the embodiment 1 based on data (here, smoke data) acquired from the detector specified by the item "Detector", the CO data needs to be acquired from the other detector than that detector. Then, the "Second Detector ID" in FIG. 25 specifies that the related device is the second detector 4, and "None" specifies that there is no device (that is, there is no need to acquire CO data from the other detector since the CO data can be acquired from the detector specified by the item "Detector").

Then, such device-specifying information is inputted by way of the operation unit 51 of the receiver 5 and stored. In particular, the information corresponding to the item "Related device" in FIG. 25 can be arbitrarily inputted and stored so that the multi-calculation value as described in the embodiment can be computed, while it may be inputted and stored as described below. If the item "Type" of the detector specified by the item "Detector" is "Only smoke", for example, any detector can be inputted and stored from among the detector of the item "Type"="CO and Smoke" or the detector of the item "Type"="Only CO" (that is, the detector provided with the CO detection unit). Specifically, for the detector to be stored, a detector with the closest distance from the detector specified by the item "Detector" may be stored from the standpoint that the multi-calculation value is computed using the smoke data and the CO data of the devices located at a mutually close position, or a detector which is provided in the same room as that where the detector specified by the item "Detector" is located may be stored from the standpoint that the multi-calculation value is computed using smoke data and CO data of devices in the same room. On the one hand, if the item "Type" of a detector specified by the item "Detector" is "Smoke and CO", for example, "None" can be inputted and stored since the multi-calculation value can be computed using the smoke data and the CO data from that detector.

Configuration—Receiver—Control Unit

Turning back to FIG. 24, the control unit 55 is equipped with a communication control unit 551, an information acquisition unit 552, a coefficient acquisition unit 553, and a determination unit 554 in terms of a functional concept. The communication control unit 551 is a communication control means configured to control communications. The information acquisition unit 552 is an information acquisition means configured to acquire information. The coefficient acquisition unit 553 is a coefficient acquisition means configured to acquire a CO-smoke conversion coefficient. The determination unit 554 is a determination means configured to determine whether fire has occurred in the monitored area. Note that processing performed by each unit in the control unit 55 is described below.

Processing

Fire detection processing performed by the disaster prevention system 300 configured as above is described hereinafter. The fire detection processing is processing to detect fire as an abnormality in the monitored area and is activated when a power switch (not shown) of each apparatus included in the disaster prevention system 300.

Processing—Fire Detection Processing by the First Detector

Figure 26:
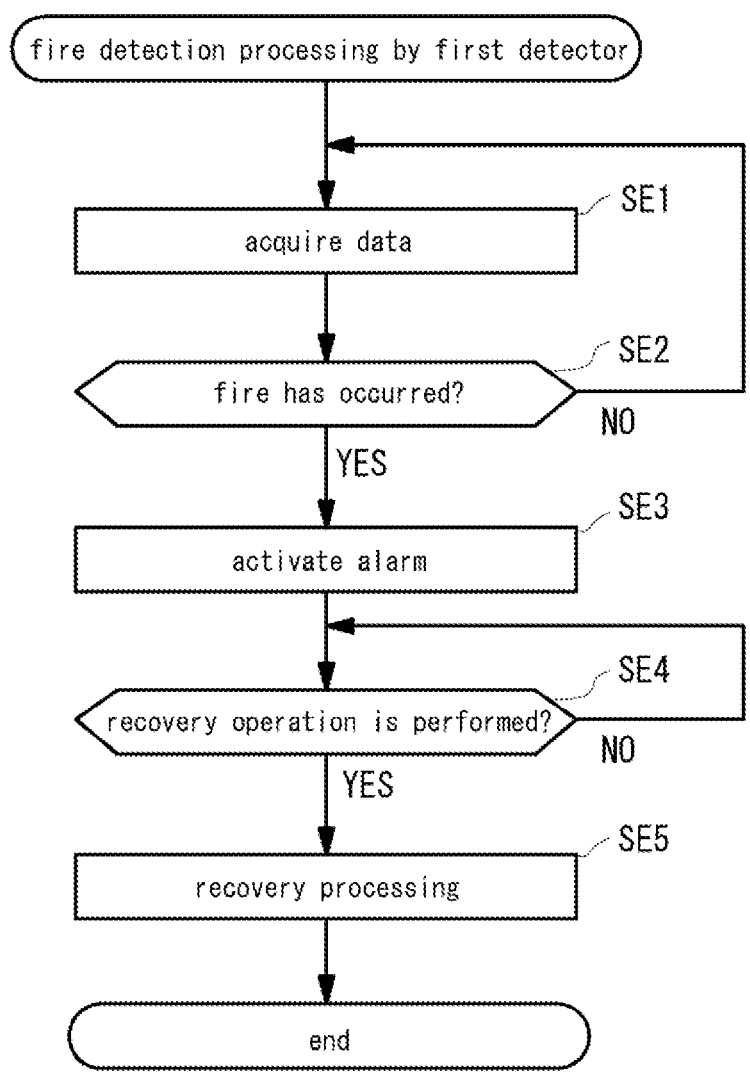
FIG. 26 is a flow chart of fire detection processing by a first detector.

First, fire detection processing by the first detector 3 is described. FIG. 26 is a flow chart of fire detection processing by the first detector.

As shown in FIG. 26, the information acquisition unit 331 of the first detector 3 acquires data in SE1. Specifically, it acquires the smoke data outputted from the smoke detection unit 31.

Then, in SE2, the determination unit 332 of the first detector 3 determines whether fire has occurred in the monitored area. Specifically, it makes a determination based on the smoke data acquired in SE1 and a threshold for the first detector described below. Here, a "threshold for the first detector" is a threshold for determining whether fire has occurred, and a preset threshold based on a predetermined fire test, for example. Then, if the smoke concentration indicated by the smoke data exceeds a threshold for the first detector, it is determined that fire has occurred (YES in SE2) and the processing proceeds to SE3. In addition, if the smoke concentration indicated by the smoke data falls below the threshold for the first detector, it is determined that fire has not occurred (NO in SE2) and the processing proceeds to SE1.

Next, in SE3, the control unit 33 performs control so that the first detector 3 transits from the normal state to the abnormality detection state. Specifically, the control unit 33 activates an alarm by the communication control unit 333 sending a first fire detection signal described below to the receiver 5 and the control unit 33 turning on an alarm activation indicator light (not shown) of the first detector 3. Here, the "first fire detection signal" is a signal indicating that fire is detected in the monitored area, and specifically a signal that includes the first detector ID stored in the storage unit 32 of the first detector 3 in FIG. 24.

Turning back to FIG. 26, in SE4, the control unit 33 of the first detector 3 monitors whether or not the recovery operation has been done. Specifically, it monitors whether or not a recovery signal described below has been received. Here, the "recovery signal" is a signal to perform recovery, and specifically, a signal outputted from the receiver 5 by pressing the recovery button 511 of the operation unit 51 in the receiver 5 in FIG. 24. Then, when the first detector 3 receives the recovery signal, it is considered that the recovery operation has been done (YES in SE4), and the processing proceeds to SE5. In addition, if the first detector 3 does not receive the recovery signal within a predetermined period of time (10 minutes or the like, for example), it is considered that the recovery operation has not been done (NO in SE4) and the processing proceeds to SE4.

In SE5, the control unit 33 of the first detector 3 performs control so that the first detector 3 transits from the abnormality detection state to the normal state. Specifically, the control unit 33 turns off the alarm activation indicator light (not shown) of the first detector 3.

Processing—Fire Detection Processing by the Second Detector

Figure 27:
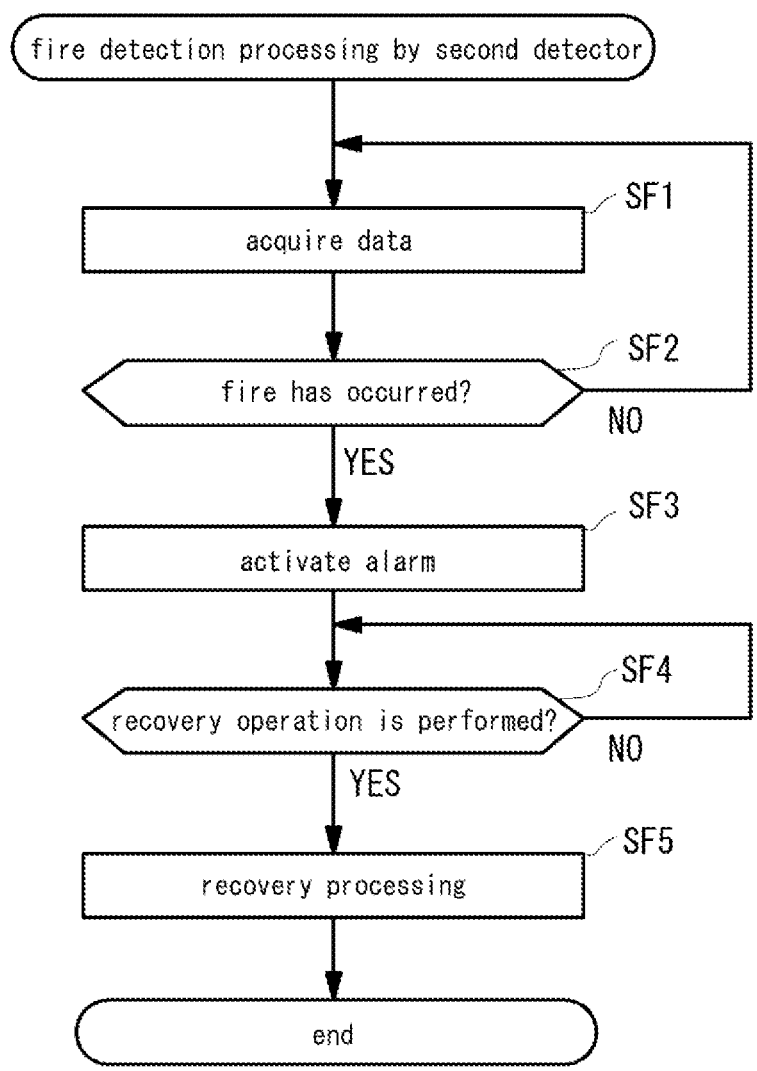
FIG. 27 is a flow chart of fire detection processing by a second detector.

Fire detection processing by the second detector 4 is described hereinafter. FIG. 27 is a flow chart of fire detection processing by the second detector.

First, as shown in FIG. 27, in SF1, the information acquisition unit 441 of the second detector 4 acquires data. Specifically, it acquires the smoke data outputted from the smoke detection unit 41 and the CO data outputted from the CO detection unit 42.

Then, in SF2, the determination unit 442 of the second detector 4 determines whether fire has occurred in the monitored area. Specifically, it makes the determination based on the smoke data and the CO data acquired in SF1. Any approach including a known approach can be used for a determination approach of the determination, while a known approach described below can be used. In this approach, specifically, a multiplication value is calculated by multiplying the smoke data by a constant defined depending on a value of CO data, and a determination is made based on the multiplication value and a threshold for the second detector described below. Here, the "threshold for the second detector" is a threshold for determining whether fire has occurred, and a preset threshold based on a predetermined fire test, for example. Then, if a multiplication value exceeds a threshold for the second detector, it is determined that fire has occurred (YES in SF2) and the processing proceeds to SF3. In addition, if the multiplication value falls below the threshold for the second detector, it is determined that fire has not occurred (NO in SF2) and the processing proceeds to SF1.

Then, in SF3, the control unit 44 of the second detector 4 performs control so that the second detector 4 transits from a normal state to an abnormality detection state. Specifically, the control unit 44 activates an alarm by the communication control unit 443 sending a second fire detection signal described below to the receiver 5 and the control unit turning on the alarm activation indicator light (not shown) of the second detector 4. Here, the "second fire detection signal" is a signal indicating that fire has been detected in the monitored area and specifically a signal that includes the second detector ID stored in the storage unit 43 in the second detector 4 in FIG. 24. Then, in SF4 and SF5 in FIG. 27, processing similar to that in SE4 and SE5 in FIG. 26 is performed.

Processing—Fire Detection Processing by the Receiver

Figure 28:
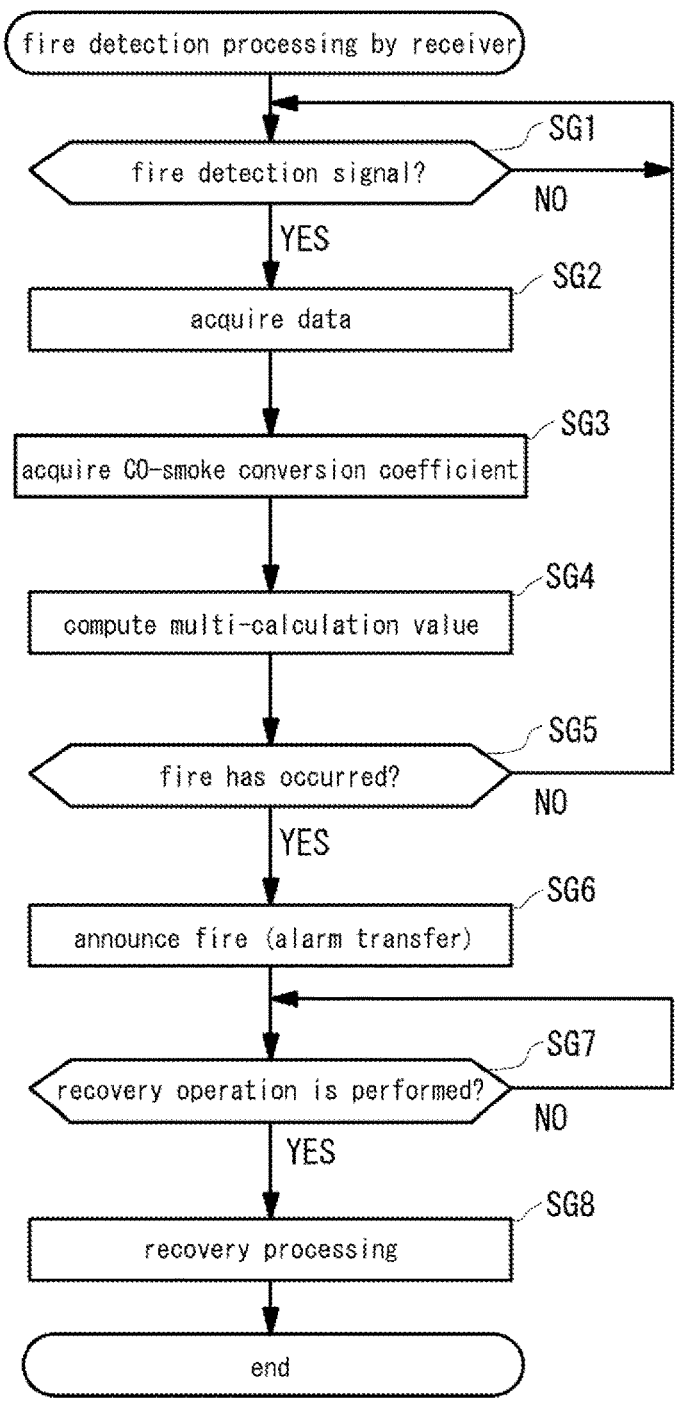
FIG. 28 is a flow chart of fire detection processing of a receiver.

Fire detection processing by the receiver 5 is described hereinafter. FIG. 28 is a flow chart of fire detection processing by the receiver.

First, as shown in FIG. 28, in SG1, the communication control unit 551 of the receiver 5 monitors whether or not a fire detection signal is received. Specifically, it monitors whether or not the first fire detection signal or the second fire detection signal as described above has been received. Then, if the first fire detection signal or the second fire detection signal has been received (YES in SG1), a fire occurrence message is displayed in the display unit 52 of the receiver 5 in FIG. 24 or the message is outputted from the acoustic unit 53 before the processing proceeds to SG2 in FIG. 28. In addition, if the first fire detection signal or the second detection signal has not been received within a predetermined period of time (10 minutes or the like, for example) (that is, neither the first fire detection signal nor the second detection signal is received) (NO in SG1), the processing proceeds to SG1.

Then, in SG2, the information acquisition unit 552 of the receiver 5 acquires data. Specifically, it specifies a device at an acquisition destination and acquired data based on identification information included in the fire detection signal received in SG1 and the device-specifying information in FIG. 25, and acquires data based on a result of that specification. Here, the "device at an acquisition destination" is a device targeted for acquisition of acquired data described below, and specifically the first detector 3 or the second detector 4. The "acquired data" is data that the receiver 5 acquires from the device at the acquisition destination, and specifically the smoke data or the CO data.

Specifically, for specification of the device at the acquisition destination and acquired data, first, a detector corresponding to identification information included in the fire detection signal is specified as the "device at an acquisition destination" of "acquired data"="smoke data". Then, in the device-specifying information in FIG. 25, identification information corresponding to the detector specified as the device at the acquisition destination of smoke data is specified by the item "Detector", and information on the item "Type" and information on the item "Related device" corresponding to the specified identification are specified. Then, based on the specified information on the item "Type", it is determined whether or not the CO data is acquired from other detector (that is, a detector other than the detector corresponding to the identification information included in the fire detection signal). Specifically, for this determination, if "CO" is included in the information on the item "Type", it is determined that the CO data is not acquired from the other detector. If "CO" is not included in the information on the item "Type", it is determined that CO data is acquired from the other detector. Then, in this determination, if it is determined that the CO data is not acquired from the other detector, a detector corresponding to the identification information on the other detector is specified as a "device at an acquisition destination" of "Acquired data"="CO data". If it is determined that the CO data is acquired from the other detector, a detector corresponding to information on the specified item "Related device" described above is specified as a "device at an acquisition destination" of "Acquired data"="CO data". Here, if the "First detector ID" is included in the fire detection signal, for example (that is, if the first fire detection signal is received), "Acquired data"="Smoke data" is specified in "Device at an Acquisition destination"="First detector 3" and "Acquired data"="CO data" is specified in "Device at an Acquisition destination"="Second detector 4". In addition, for example, if "Second detector ID" is included in the fire detection signal (that is, the second fire detection signal is received), "Acquired data"="Smoke data and CO data" is specified in "Device at an acquisition destination"="Second detector 4".

Then, communication is performed and data is acquired based on a result of the specifications. Any approach can be used for the communication approach while an approach described below may be used. For this approach, specifically, data is acquired by the communication control unit 551 of the receiver 5 transmitting a request signal described below, the first detector 3 or the second detector 4 transmitting a response signal described below in response to the transmitted request signal, and the receiver 5 receiving the transmitted response signal. Here, if "Acquired data"="Smoke data" is specified in "Device at an acquisition destination"="First detector 3" and "Acquired data"="CO data" is specified in "Device at an acquisition destination"="Second detector 4", for example, a request signal requesting the smoke data is transmitted to the first detector and a request signal requesting the CO data is transmitted to the second detector 4. On the one hand, in response to the request signals, the communication control unit 333 of the first detector 3 transmits to the receiver 5 a response signal including smoke data which is a detection result of the smoke detection unit 31, and the communication control unit 443 of the second detector 4 transmits to the receiver 5 a response signal including the CO data which is a detection result of the CO detection unit 42. Then, the receiver 5 receives the response signal so as to acquire the smoke data and the CO data. Note that even if "Acquired data"="Smoke data and CO data" is specified in the "Device at an acquisition destination"="Second detector 4", data is acquired similarly using the request signals and the response signals as described above.

Turning back to FIG. 28, in SG3, the coefficient acquisition unit 553 of the receiver 5 acquires a CO-smoke conversion coefficient. Specifically, the coefficient acquisition unit 553 specifies a range of the CO gas concentration corresponding to the CO gas concentration indicated by the CO data acquired in SG2 in the CO-smoke conversion coefficient-specifying information in FIG. 4, and acquires a CO-smoke conversion coefficient corresponding to the specified range of the CO gas concentration. Here, for example, in FIG. 4, if the CO gas concentration is 5 (ppm), the coefficient acquisition unit 533 specifies "less than 30 (ppm)" as the range of the CO gas concentration corresponding to 5 (ppm), and acquires "0.1" as the CO-smoke conversion coefficient corresponding to the specified range. In addition, if the CO gas concentration is 40 (ppm), for example, the coefficient acquisition unit 533 specifies "30 (ppm) or more to less than 60 (ppm)" is specified as the range of the CO gas concentration corresponding to 40 (ppm), and acquires "0.23" as the CO-smoke conversion coefficient corresponding to the specified range. In addition, if the CO gas concentration is 65 (ppm), the coefficient acquisition unit 533 specifies "60 (ppm) or more" as the range of the CO gas concentration corresponding to 65 (ppm), and acquires "0.3" as the CO-smoke conversion coefficient corresponding to the specified range.

Turning back to FIG. 28, in SG4, the determination unit 554 of the receiver 5 computes a multi-calculation value based on the arithmetic processing shown in FIG. 6, as with the case of SA3 in FIG. 5. Here, for example, if the smoke data and the CO data acquired in SG2 in FIG. 28 are "D1" and "D2", the CO-smoke conversion coefficient acquired in SG3 is "C2", and the first sensitivity coefficient is "C1", "D1×C1+D2×C2" is computed as the multi-calculation value in SG4.

Turning back to FIG. 28, in SG5, the determination unit 554 of the receiver 5 determines whether fire has occurred in the monitored area. Specifically, a determination is made on the basis of the multi-calculation value computed in SG4 and a determination threshold having a configuration similar to that of the determination threshold described in the embodiment 1. Then, if the multi-calculation value exceeds the determination threshold, it is determined that fire has occurred (YES in SG5), and the processing proceeds to SG6. In addition, if the multi-calculation value falls below the determination threshold, it is determined that fire has not occurred (NO in SG5), and the processing proceeds to SG1. Note that in SG5, since a determination is made using the multi-calculation value, fire occurrence can be determined promptly and reliably as described in the embodiment 1.

Then, in SG6, the control unit 55 of the receiver 5 announces fire by performing alarm transfer output to a predetermined external supervisory board (not shown).

Next, in SG7, the control unit 55 of the receiver 5 monitors whether a recovery operation is performed. Specifically, it monitors whether or not the recovery button 511 of the control unit 51 in the receiver 5 of FIG. 24 is pressed. Then, when the recovery button 511 is pressed, it is considered that the recovery operation has been performed (YES in SG7), and the processing proceeds to SG8. In addition, if the recovery button 511 is not pressed within a predetermined period of time (10 minutes, for example), it is considered that the recovery operation has not been performed (NO in SG7), and the processing proceeds to SG8.

Then, in SG8, the control unit 55 of the receiver 5 performs the recovery processing. Specifically, it transmits a recovery signal to a detector corresponding to the identification information included in the fire detection signal received in SG1.

Effect of the Embodiment 5

As such, according to the embodiment, since the CO-smoke conversion coefficient according to the CO gas concentration and the smoke concentration can be reflected in a determination of whether an abnormality has occurred, irrespective of magnitude of the smoke data and the CO data, occurrence of the abnormality can be detected promptly and reliably in the monitored area. Therefore, even when fire occurs in which a relatively small amount of CO gas is generated, the CO-smoke conversion coefficient can be reflected in the determination of whether fire has occurred, irrespective of the CO gas concentration. Thus, occurrence of the fire can be detected promptly and reliably. Alternatively, as with fumigation fire, even when fire occurs in which a relatively large amount of carbon monoxide gas is generated but an extremely small amount of smoke is generated, for example, the CO-smoke conversion coefficient can be reflected in the determination of whether fire has occurred, irrespective of the smoke concentration. Thus, occurrence of the fire can be detected promptly and reliably.

In addition, since the CO-smoke conversion coefficient can be acquired based on the CO data and the acquired CO-smoke conversion coefficient can be reflected in the determination of whether an abnormality has occurred, a CO-smoke conversion coefficient suitable for the environment in the monitored area can be reflected in the determination, and thus occurrence of the abnormality can be detected promptly and reliably.

In addition, smoke data can be acquired from the first detector 3 and CO data can be acquired from the second detector 4. Thus, separate provision of the first detector 3 and the second detector 4 at a location suitable for detection of occurrence of an abnormality enables acquisition of smoke data and CO data in which the smoke concentration and the CO gas concentration in the monitored area are reflected appropriately, and occurrence of an abnormality can be thereby detected promptly and reliably.

In addition, since it is possible to determine whether fire has occurred in the monitored area by using the multi-calculation value obtained by reflecting the CO-smoke conversion coefficient and the CO data in the smoke data, fire occurrence in the monitored area can be detected promptly and reliably.

Embodiment 6

An embodiment 6 is described hereinafter. The embodiment 6 is an embodiment in a case in which each of a first detector having a smoke detection unit and a temperature detection unit and a second detector having a smoke detection unit, a temperature detection unit, and a CO detection unit determines whether an abnormality has occurred with a known approach, and a receiver makes a determination using a first coefficient and a second coefficient based on data acquired from the first detector or the second detector. Note that a configuration of the embodiment 6 is substantially identical to that of the embodiment 5 unless otherwise specified. Any configuration which is substantially identical to that of the configuration 5 is assigned with the same symbols as those used in the embodiment 5 if needed, and a description thereof is omitted.

Configuration

Figure 29:
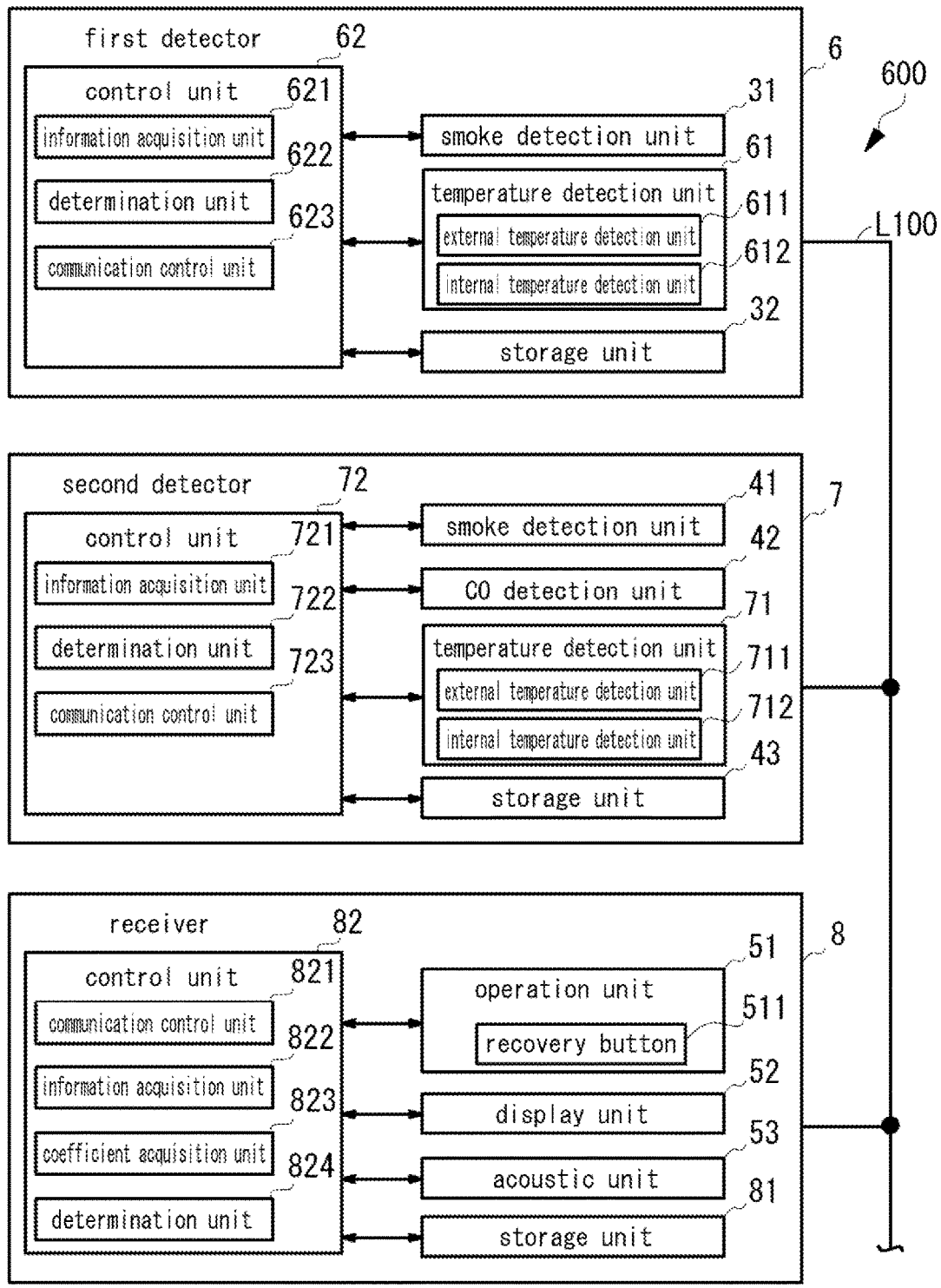
FIG. 29 is a block diagram showing a disaster prevention system according to an embodiment 6.

First, a configuration of a disaster prevention system according to the embodiment 6 is described. FIG. 29 is a block diagram showing the fire prevention system according to the embodiment.

The fire prevention system 600 is equipped with a first detector 6, a second detector 7, and a receiver 8.

Configuration—First Detector

The first detector 6 is equipped with a smoke detection unit 31, a temperature detection unit 61, a storage unit 32, and a control unit 62.

Configuration—First Detector—Temperature Detection Unit

The temperature detection unit 61 is a temperature detection means configured to detect the temperature as a third physical quantity, and, specifically equipped with an external temperature detection unit 611 and an internal temperature detection unit 612. While any temperature sensor may be used as the temperature detection unit 61, a description is here provided below on the assumption that a known temperature sensor for detecting temperature based on electrical resistance of a thermistor is used. The external temperature detection unit 611 is an external temperature detection means that detects external temperature of the first detector 6, and specifically outputs external temperature data (third information) indicating the detected temperature. The internal temperature detection unit 612 is an internal temperature detection means to detect internal temperature of the first detector 6, and specifically outputs internal temperature data (third information) indicating the detected temperature. Note that in the description, "external temperature data" and "internal temperature data" are collectively referred to as "temperature data" if there is no need to make a distinction therebetween.

Configuration—First Detector—Control Unit

The control unit 62 is equipped with an information acquisition unit 621, a determination unit 622, ad a communication control unit 633 in terms of a functional concept. A configuration of each unit is similar to that of each unit having the same name in the control unit 33 in the first detector 3 of FIG. 24.

Configuration—Second Detector

Turning back to FIG. 29, the second detector 7 is equipped with a smoke detection unit 41, a CO detection unit 42, and a temperature detection unit 71, a storage unit 43, and a control unit 72.

Configuration—Second Detector—Temperature Detection Unit

The temperature detection unit 71 is a temperature detection means configured to detect the temperature and equipped with an external temperature detection unit 711 and an internal temperature detection unit 712. A specific configuration thereof is similar to that of the temperature detection unit 61 in the first detector 6. The external temperature detection unit 711 is an external temperature detection means that detects the external temperature of the second detector 7 and outputs external temperature data indicating the detected temperature. The internal temperature detection unit 712 is an internal temperature detection means that detects the internal temperature of the second detector 7 and specifically outputs internal temperature data indicating the detected temperature.

Configuration—Second Detector—Control Unit

The control unit 72 is equipped with an information acquisition unit 721, a determination unit 722, and a communication control unit 723 in terms of a functional concept. A configuration of each unit is similar to that of each unit having the same name in the control unit 44 in the second detector 4 of FIG. 24.

Configuration—Receiver

Turning back to FIG. 29, the receiver 8 is equipped with an operation unit 51, a display unit 52, an acoustic unit 53, a storage unit 81, and a control unit 82.

Configuration—Receiver—Storage Unit

The storage unit 81 is a storage means in which programs and various types of data necessary for operation of the receiver 8 are stored. Specifically, it stores a receiver ID, which is identification information for uniquely identifying itself (that is, the receiver 8), device-specifying information described below, CO-smoke conversion coefficient-specifying information of FIG. 13 that is created with the creation method example described in the embodiment 2, and second sensitivity coefficient information of FIG. 14.

FIG. 30 is a view showing device-specifying information. The "device-specifying information" is information to specify a device, and specifically is information to specify the detectors included in the disaster prevention system 600. A specific configuration of the device-specifying information is similar to that of the device-specifying information of FIG. 25, except stored contents. Then, in the device-specifying information of FIG. 30, "Only smoke and temperature" corresponding to the item "Type" specifies that the detector is a detector provided with only the smoke detection unit and the temperature detection unit from among the smoke detection unit, the temperature detection unit, and the CO detection unit. "Smoke, temperature, and CO" specifies that the detector is a detector provided with all of the smoke detection unit, the temperature detection unit, and the CO detection unit.

Configuration—Receiver—Control Unit

Turning back to FIG. 29, the control unit 82 is equipped with a communication control unit 821, an information acquisition unit 822, a coefficient acquisition unit 823, and a determination unit 824 in terms of a functional concept. The communication control unit 821 is a communication control means configured to control communications. The information acquisition unit 822 is an information acquisition means configured to acquire information. The coefficient acquisition unit 823 is a coefficient acquisition means configured to acquire a CO-smoke conversion coefficient and a second sensitivity coefficient. The determination unit 824 is a determination means configured to determine whether fire has occurred in the monitored area. Note that processing performed by each unit in the control unit 82 is described below.

Processing

Fire detection processing performed by the receiver 8 of the fire prevention system 600 configured as above is described hereinafter. The fire detection processing is processing to detect fire as an abnormality in the monitored area, and activated when a power switch (not shown) of each apparatus included in the disaster prevention system 600 is turned on, for example. Note that since the fire detection processing by the first detector 6 and the second detector 7 is similar to the fire detection processing by the first detector 2 and the second detector 4 in FIG. 24, a description thereof is omitted.

Processing—Fire Detection Processing by the Receiver

Figure 31:
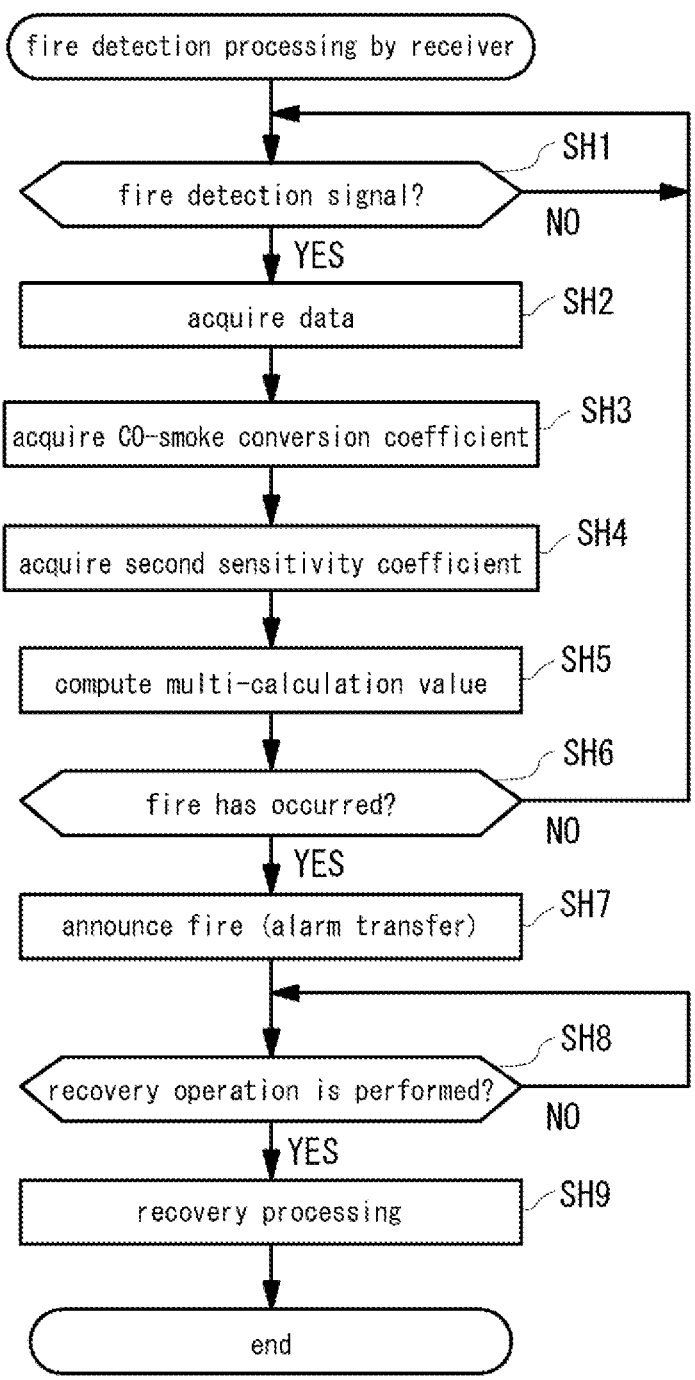
FIG. 31 is a flow chart of fire detection processing by a receiver.

FIG. 31 is a flow chart of fire detection processing by the receiver. First, as shown in FIG. 31, in SH1, the communication control 821 of the receiver 8 monitors whether or not a fire detection signal is received. Specifically, it performs processing similar to SG1 in FIG. 28 by monitoring whether or not a first fire detection signal (that is, a signal including the first detector ID) or a second fire detection signal (that is, a signal including the second detector ID) is received.

Turning back to FIG. 31, in SH2, the information acquisition unit 822 of the receiver 8 acquires data. Specifically, similar to the processing of SG2 in FIG. 28, it specifies a device at an acquisition destination and acquired data based on identification information included in the fire detection signal received in SH1 and the device-specifying information in FIG. 30, and acquires data based on a result of that specification.

Specifically, for specification of the device at the acquisition destination and the acquired data, first, a detector corresponding to the identification information included in the fire detection signal is specified as the "Device at an acquisition destination" of "Acquired data"="Smoke data and temperature data". Then, in the device-specifying information in FIG. 30, identification information corresponding to the detector specified as the device at the acquisition destination of the smoke data and temperature data is specified by the item "Detector", and information in the item "Type" corresponding to the specified identification information and information of the "Related device" are specified. Then, based on the specified information of the item "Type", it is determined whether or not the CO data is acquired from other detector, similar to SG2 in FIG. 28. Then, in this determination, if it is determined that the CO data is not acquired from the other detector, a detector corresponding to the identification information in the fire detection signal is specified as a "Device at an acquisition destination" of "Acquired data"="CO data". If it is determined that the CO data is acquired from the other detector, a detector corresponding to information on the specified item "Related device" described above is specified as a "device at the acquisition destination" of "Acquired data"="CO data". Here, if the "First detector ID" is included in the fire detection signal, for example (that is, when the first fire detection signal is received), "Acquired data"="Smoke data and temperature data" is specified in the "Device at the acquisition destination"="First detector 6", and "Acquired data"="CO data" is specified in the "Device at the acquisition destination"="Second detector 7". In addition, for example, if the "second detector ID" is included in the fire detection signal (that is, when the second fire detection signal is received), "Acquired data"="Smoke data, temperature data, and CO data" is specified in the "Device at the acquisition destination"="Second detector 7".

Then, communication is performed and data is acquired based on a result of the specifications. Here, if "Acquired data"="Smoke data and temperature data" is specified in the "Device at the acquisition destination"="First detector 6" and "Acquired data"="CO data" is specified in the "Device at the acquisition destination"="Second detector 7", the smoke data and the temperature data are acquired from the first detector 6 and the CO data is acquired from the second detector 7. In addition, if "Acquired data"="Smoke data, temperature data, and CO data" is specified in the "Device at the acquisition destination"="Second detector 7", the smoke data, the temperature data, and the CO data are acquired from the second detector 7.

Turning back to FIG. 31, in SH3, the coefficient acquisition unit 823 of the receiver 8 acquires a CO-smoke conversion coefficient. Specifically, the coefficient acquisition unit 823 first performs processing similar to SG3 in FIG. 28 to specify a range of the CO gas concentration corresponding to the CO gas concentration indicated by the CO data acquired in SH2 in FIG. 31 in the CO-smoke conversion coefficient-specifying information in FIG. 13, and acquires a candidate for the CO-smoke conversion coefficient corresponding to the specified range of the CO gas concentration (that is, a coefficient in the item "First CO-smoke conversion coefficient" of FIG. 13 and a coefficient in the item "Second CO-smoke conversion coefficient"). Then, the coefficient acquisition unit 823 compares the external temperature indicated by the external temperature data acquired in SH2 in FIG. 13 with a predetermined temperature threshold. Then, based on a result of the comparison, the coefficient acquisition unit 823 acquires, as a CO-smoke conversion coefficient used in the fire detection processing, one of the coefficient in the item "First CO-smoke conversion coefficient" and the coefficient in the item "Second CO-smoke conversion coefficient" that are acquired as the candidate mentioned above. Here, the "predetermined temperature threshold" refers to a threshold to correspond to a type of fire that has occurred, and is, for example, a threshold (70 (° C.) or the like, for example) corresponding to a determination criterion on whether fire that has occurred is flaming fire or fumigation fire. The predetermined temperature threshold is input and set through the operation unit 51 of the receiver 8 in FIG. 29. Here, if "1.5" and "0.23" in FIG. 13 are acquired as the candidate for the CO-smoke conversion coefficient, and when the external temperature indicated by the external temperature data acquired in SH2 in FIG. 31 falls below a predetermined temperature threshold, the variable in the item "Second CO-smoke conversion coefficient" (that is, "0.23") is acquired as the CO-smoke conversion coefficient. When the external temperature indicated by the external temperature data acquired in SH2 in FIG. 31 exceeds the predetermined temperature threshold, the variable in the item "First CO-smoke conversion coefficient" (that is, "1.5") is acquired as the CO-smoke conversion coefficient.

Turning back to FIG. 31, in SH4, the coefficient acquisition unit 823 of the receiver 8 acquires a second sensitivity coefficient. Specifically, the coefficient acquisition unit 823 specifies a temperature difference between the external temperature and the internal temperature as well as the external temperature, based on the external temperature indicated by the external temperature data acquired in SH2 and the internal temperature indicated by the internal temperature data acquired in SH2, respectively. Then, the second coefficient information of FIG. 14 acquires a second sensitivity coefficient corresponding to a result of the specification. Here, when the external temperature data and the internal temperature data acquired in SH2 in FIG. 31 are "55 (° C.)" and "30 (° C.)", the temperature difference is "25 (° C.)". Thus, "1.4" in the rightmost column in FIG. 14 which corresponds to the temperature difference of "25(° C.)" and the external temperature of "55(° C.)" is acquired as the second sensitivity coefficient.

Turning back to FIG. 31, in SH5, the determination unit 824 of the receiver 8 computes a multi-calculation value based on the arithmetic processing shown in FIG. 16, similar to SB4 in FIG. 15. Here, for example, if the smoke data and the CO data acquired in SH2 in FIG. 31 are "D1" and "D2", the CO-smoke conversion coefficient acquired in SH3 is "C2", and the second sensitivity coefficient acquired in SH4 is "C3", "D1×C1×C3+D2×C2" is computed as the multi-calculation value in SH5. After this, in SH6 to SH9 in FIG. 31, processing similar to SG5 to SG8 in FIG. 28 is performed.

Effects of the Embodiment 6

As such, according to the embodiment, since the CO-smoke conversion coefficient corresponding to a fire type can be acquired based on detection results of the temperature detection unit 61 or the temperature detection unit 71. Thus, the CO-smoke conversion coefficient suitable for fire that is occurring in the monitored area can be reflected in a determination of whether fire has occurred, and occurrence of an abnormality in the monitored area can be detected promptly and reliably.

Embodiment 7

Figure 32:
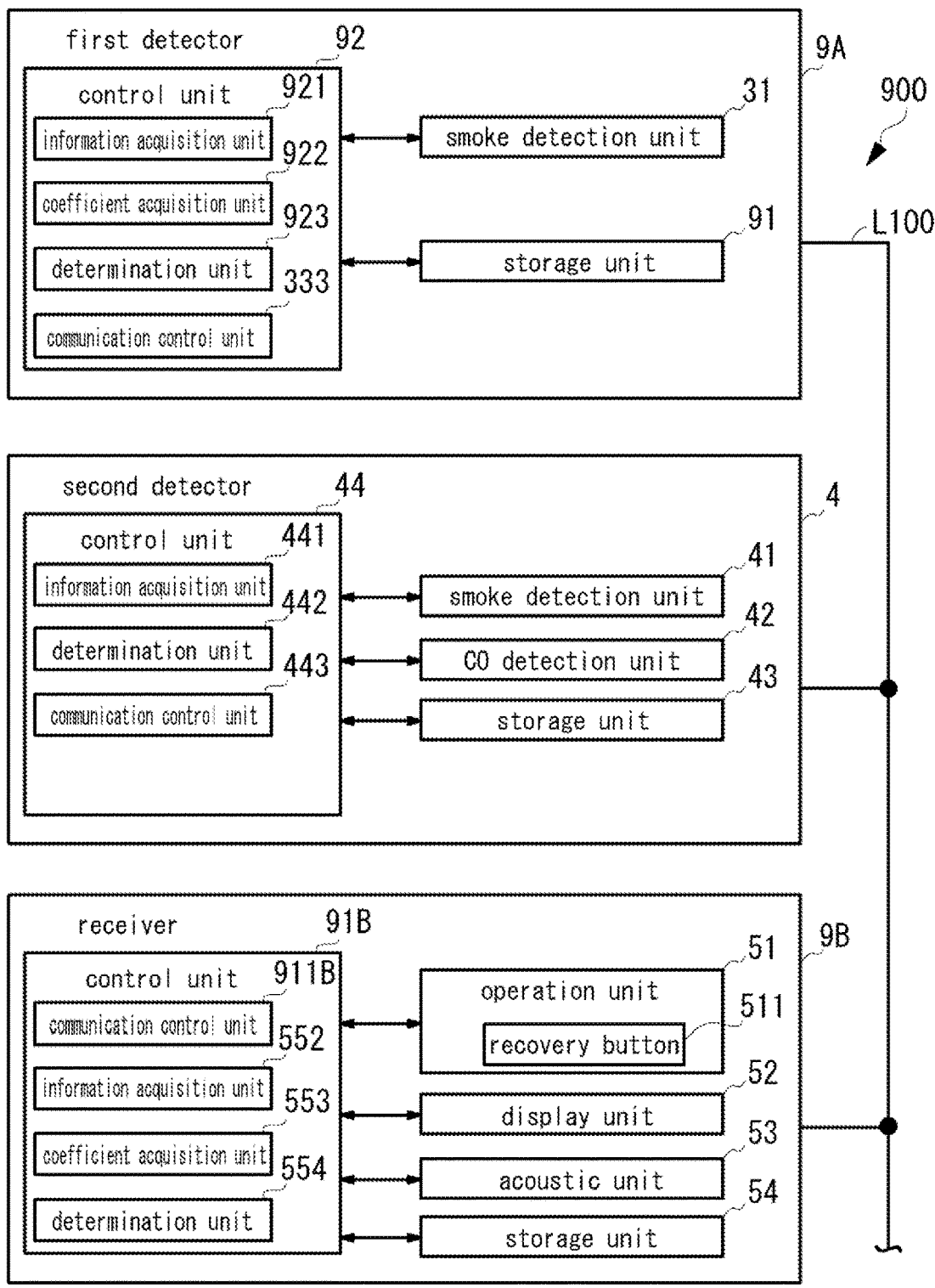
FIG. 32 is a block diagram showing a disaster prevention system according to an embodiment 7.

An embodiment 7 is described hereinafter. The embodiment 7 is an embodiment in a case in which a first detector having a smoke detection unit makes a determination using a first coefficient based on data relayed by a receiver, a second detector having a smoke detection unit and a CO detection unit determines whether an abnormality has occurred with a known approach, and the receiver makes a determination using the first coefficient based on data acquired from the first detector or the second detector. Note that a configuration of the embodiment 7 is substantially identical to that of the embodiment 5 unless otherwise specified. Any configuration which is substantially identical to the configuration 5 is assigned with same symbols as those used in the embodiment 5 if needed, and a description thereof is omitted.
Configuration First, a configuration of a disaster prevention system according to the embodiment 7 is described hereinafter. FIG. 32 is a block diagram showing the disaster prevention system according to the embodiment.

A disaster prevention system 900 is equipped with a first detector 9A, a second detector 4, and a receiver 9B.
Configuration—First Detector The first detector 9A is equipped with a smoke detection unit 31, a storage unit 91, and a control unit 92.
Configuration—First Detector—Storage Unit The storage unit 91 is a storage means in which programs and various types of data necessary for operation of the first detector 9A are stored. Specifically, it stores CO-smoke conversion coefficient-specifying information as shown in FIG. 4.
Configuration—First Detector—Control Unit The control unit 92 is equipped with an information acquisition unit 921, a coefficient acquisition unit 922, a determination unit 923, and a communication control unit 33 in terms of a functional concept. The information acquisition unit 921 is an information acquisition means configured to acquire information. The coefficient acquisition unit 922 is a coefficient acquisition means configured to acquire a CO-smoke conversion coefficient. The determination unit 923 is a determination means configured to determine whether fire has occurred in the monitored area. Note that processing performed by each unit in the control unit 92 is described below.

Configuration—Receiver

Figure 33:
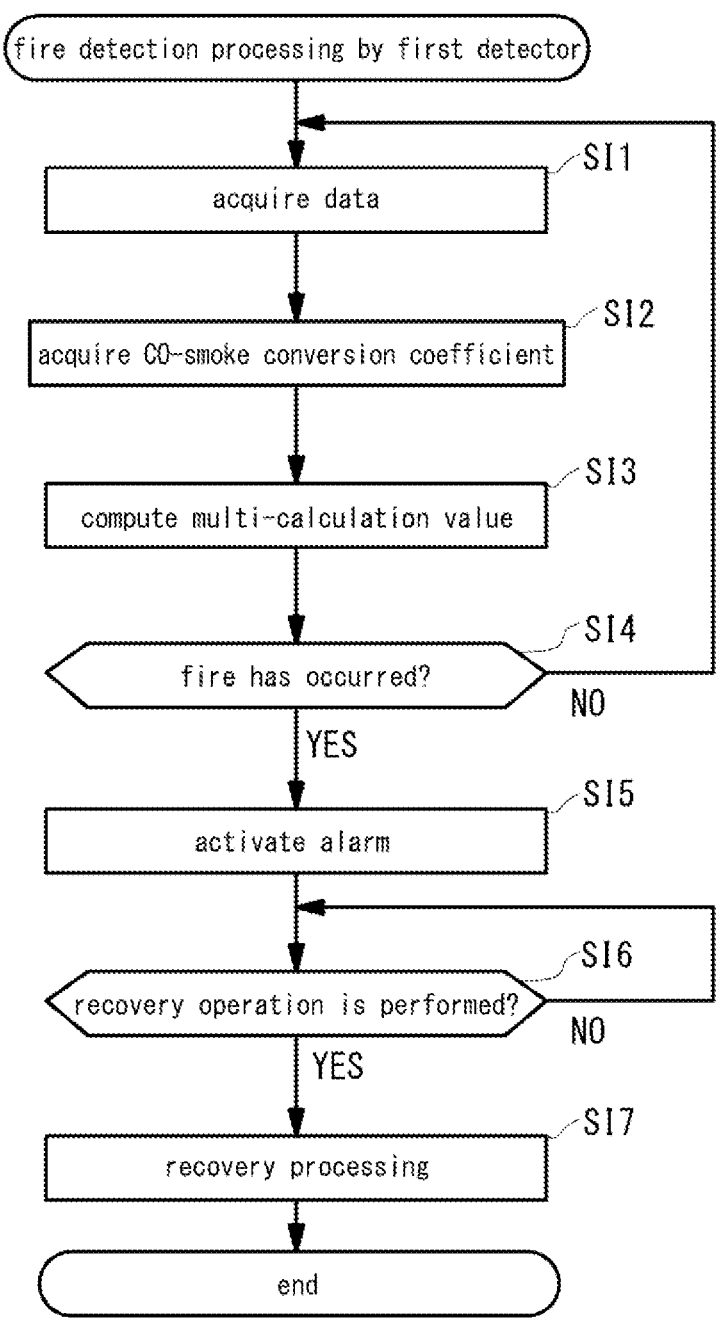
FIG. 33 is a flow chart of fire detection processing by a first detector.

In addition, the receiver 9B is equipped with an operation unit 51, a display unit 52, an acoustic unit 53, a storage unit 54, and a control unit 91B.
Configuration—Receiver—Control Unit The control unit 91B is equipped with a communication control unit 911B, an information acquisition unit 552, a coefficient acquisition unit 553, and a determination unit 554 in terms of a functional concept. The communication control unit 911B is a communication control means configured to control communications. Note that processing performed by each unit in the control unit 91B is described below.
Processing Fire detection processing performed by the first detector 9A of the disaster prevention system 900 configured as above is described hereinafter. The fire detection processing is processing to detect fire as an abnormality in the monitored area and activated when a power switch (not shown) of each apparatus included in the disaster prevention system 900 is turned on, for example. Note that since the fire detection processing by the second detector 4 and the receiver 9B is similar to the fire detection processing by the second detector 4 and the receiver 5 in FIG. 24, a description thereof is omitted.
Processing—Fire Detection Processing by the First Detector FIG. 33 is a flow chart of fire detection processing by the first detector. First, as shown in FIG. 33, in SI1, the information acquisition unit 921 of the first detector 9A acquires data. Specifically, the information acquisition unit 921 acquires smoke data by performing processing similar to the processing of SE1 in FIG. 26, and also acquires CO data based on relay processing by the receiver 9B, described below.

Figure 34:
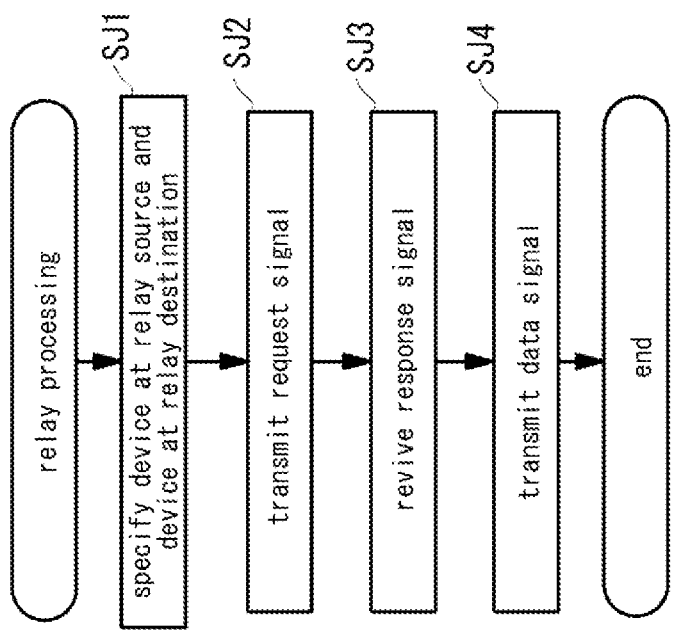
FIG. 34 is a flow chart of relay processing.

FIG. 34 is a flow chart of relay processing. The "relay processing" is processing to relay data, and specifically is processing in which the receiver 9B relays the CO data between the first detector 9A and the second detector 4 and which is repeatedly performed at predetermined intervals (at intervals of a few seconds, for example).

As shown in FIG. 34, in SJ1, the communication control unit 911B of the receiver 9B specifies a device at a relay source and a device at a relay destination. Here, the "device at a relay source" is a device that serves as a relay source of data, and the "device at a relay destination" is a device that serves as a relay destination of data. For the processing of SJ1, specifically, the second detector 4, which is a detector for which "CO" is included in the item "Type" (that is, "Smoke and CO" in FIG. 25), is specified as the device at the relay source. The first detector 9A in FIG. 32, which is a detector for which "CO" is not included in the item "Type" (that is, "Only Smoke" in FIG. 25), is specified as the device at the relay destination.

Turning back to FIG. 34, in SJ2, the communication control unit 911B of the receiver 9B transmits a request signal. Specifically, in SJ2, the communication control unit 911B transmits the request signal requesting CO data to the second detector 4 specified as the "device at the relay source" in SJ1. On the other hand, in response to the request signal, the communication control unit 443 of the second detector transmits to the receiver 9B a response signal including the CO data that is a detection result of the CO detection unit 42.

Then, in SJ3, the communication control unit 911B of the receiver 9B receives the response signal transmitted from the second detector 4.

Then, in SJ4, the communication control unit 911B of the receiver 9B transmits a data signal. Here, the "data signal"

is a signal including data and specifically is a signal including the CO data. For the processing of SJ4, specifically, the communication control unit 911B receives the CO data included in the response signal received in SJ3, generates a data signal including the acquired CO data, and transmits the generated data signal to the first detector 9A specified as the "device at the relay destination" in SJ1.

Turning back to FIG. 33, for the processing to acquire the CO data in SI1, specifically, the first detector 9A receives the data signal transmitted in SJ4 in FIG. 34, and acquires the CO data included in the received data signal.

Turning back to FIG. 33, in SI2, the coefficient acquisition unit 922 acquires the CO-smoke conversion coefficient. Specifically, the coefficient acquisition unit 922 performs processing similar to the processing of SG3 in FIG. 28 and acquires the CO-smoke conversion coefficient from the CO-smoke conversion coefficient-specifying information stored in the storage unit 91 in the first detector 9A in FIG. 32. After this, processing similar to the processing of SG4 and SG5 in FIG. 28 is performed in SI3 and SI4 in FIG. 33, and processing similar to the processing of SE3 to SE5 in FIG. 26 is performed in S15 to S17 in FIG. 33

Effects of the Embodiment 7

As such, according to the embodiment, the CO-smoke conversion coefficient corresponding to the CO gas concentration and the smoke concentration can be reflected in a determination of whether an abnormality has occurred, irrespective of magnitude of the smoke concentration indicated by the smoke data and the CO gas concentration indicated by the CO data. Thus, occurrence of an abnormality in the monitored area can be detected promptly and reliably.

In addition, since the CO-smoke conversion coefficient can be acquired based on the CO data and the acquired CO-smoke conversion coefficient can be reflected in a determination of whether an abnormality has occurred, the CO-smoke conversion coefficient suitable for a monitored area can be reflected in the determination and occurrence of an abnormality can be detected promptly and reliably.

In addition, since the smoke data of the first detector 9A and the CO data of the second detector 4 can be acquired, separate provision of the first detector 9 and the second detector 4 at a location suitable for detection of occurrence of an abnormality enables acquisition of the smoke data and the CO data in which the smoke concentration and the CO gas concentration in the monitored area are reflected appropriately, and occurrence of an abnormality can be thereby detected promptly and reliably. In addition, since there is no need to provide a CO detector for the first detector 9A, the number of parts can be reduced, which makes it possible to provide an inexpensive first detector 9A.

In addition, since the CO data can be acquired from the second detector 4 via the receiver 9B that relays communications performed between the first detector 9A and the second detector 4, safety of communications can be secured. Hence, occurrence of an abnormality can be detected promptly and reliably by preventing acquisition of the CO data from being inhibited due to a communication failure.

In addition, since it is possible to determine whether fire has occurred in the monitored area by using the multi-calculation value obtained by reflecting the CO-smoke conversion coefficient and the CO gas concentration indicated by the CO data in the smoke concentration indicated by the smoke data, fire occurrence in the monitored area can be detected promptly and reliably.

Variations of the Embodiments

While the respective embodiments according to the present invention have been described so far, specific configurations and means thereof can be arbitrarily altered and modified within a scope of a technological idea of each invention. Such variations are descried hereinafter.

Problems to be Solved and Effect of the Invention

First, problems to be solved or effect of the invention shall not be limited to what have been described above. They may vary depending on an implementation environment of the invention or details of a configuration, and only some of the problems described above may be solved or only some of the effects described above may be successful.

Distribution or Integration

In addition, the configurations described above are functionally conceptual, and are not necessarily configured physically as shown. That is, a specific mode of distribution or integration of each unit is not limited to the modes shown. All or some of respective units can be configured through functional or physical distribution or integration in an arbitrary unit. For example, a disaster prevention system may be configured through arbitrary combination of respective devices or units in the respective embodiments (embodiments 5 to 7, in particular) described above. In this case, any device (own device, hereinafter) of devices included in a disaster prevention system may perform fire detection processing by acquiring each piece of data (that is, smoke data, temperature data, or CO data) from a detection unit in the own device or from that of other device and computing a multi-calculation value from the acquired data. In addition, in this case, other device may acquire the multi-calculation value computed by the own device by performing communication with the own device and perform the fire detection processing based on the acquired multi-calculation value. In more concrete terms, for example, a receiver of a disaster prevention system may perform the fire detection processing by acquiring two types of data (smoke data and CO data, smoke data and temperature data, or CO data and temperature data) of smoke data, temperature data, or CO data and computing a multi-calculation value based on the acquired data. In addition, for example, a detector of a disaster prevention system may perform the fire detection processing by acquiring two types of data of smoke data, temperature data, or CO data from a detector of the disaster prevention system (own device or other device) and computing a multi-calculation value based on the acquired data.

CO-Smoke Conversion Coefficient-Specifying Information

In addition, in the respective embodiments described above, the case is described in which a CO-smoke conversion coefficient is associated with each range of the CO gas concentration in CO-smoke conversion coefficient-specifying information, a case shall not be limited thereto. For example, in CO-smoke conversion coefficient-specifying information, information indicating only one CO-smoke conversion coefficient is included irrespective of a range of the CO gas concentration, and the determination unit of each embodiment (determination unit 276 in FIG. 3 or the like, for example) may acquire the one CO-smoke conversion coefficient to perform processing. In addition, for example, in the CO-smoke conversion coefficient-specifying information, approximate expression information indicating an approximate expression described in the "first creation method" is included and the acquisition unit of each embodiment (acquisition unit 275 in FIG. 3 or the like, for example) may compute a CO-smoke conversion coefficient based on the approximate expression information to acquire the computed CO-smoke conversion coefficient.

In addition, in the respective embodiments described above, while the case is described in which a CO-smoke conversion coefficient is defined in a step-by-step manner for each range of the CO gas concentration in the CO-smoke conversion coefficient-specifying information, a case shall not be limited thereto. For example, as described in the "first creation method" for creating CO-smoke conversion coefficient-specifying information, in the CO-smoke conversion coefficient-specifying information, a CO-smoke conversion coefficient is defined in a step-by-step manner for each range of the smoke concentration, by creating CO-smoke conversion coefficient-specifying information after setting a value for the smoke concentration as a predetermined segment threshold. The acquisition unit of each embodiment (acquisition unit 275 in FIG. 3 or the like, for example) may acquire a CO-smoke conversion coefficient corresponding to the smoke concentration indicated by the smoke data, from the CO-smoke conversion coefficient-specifying information.

In addition, in the respective embodiments described above, while the case is described in which in the "second creation method" described above, a ratio of the smoke concentration with respect to the CO gas concentration is acquired as a CO-smoke conversion coefficient, a case shall not be limited thereto. For example, a ratio of the CO gas concentration with respect to the smoke node (that is, an inverse number of the ratio computed with the "second creation method") may be acquired as a CO-smoke conversion coefficient. In this case, processing is performed after converting smoke data into data corresponding to CO data by using the acquired CO-smoke conversion coefficient (which may also be hereinafter referred to as "C4"). Specifically, "D1×C1×C4+D2" is computed as a multi-calculation value for each information indicated in FIG. 6, for example, and it is determined whether fire has occurred based on the computed multi-calculation value. In addition, for each information indicated in FIG. 20, for example, "D1×C1×C4+D2" is computed as a multi-calculation value in a "normal case", and "D1×C1×C4+D3" is computed as a multi-calculation value in a "predetermined case", and it is determined whether fire has occurred based on the computed multi-calculation value.

Multi-Calculation Value

In addition, in the respective embodiments described above, while the case is described in which the smoke correction B1, B11 in FIG. 6 or FIG. 20 is performed to compute a multi-calculation value, a case shall not be limited thereto. For example, a multi-calculation value may be computed without performing the smoke correction B1 (or the smoke correction B11). In this case, in FIG. 6, for example, "D1+D2×C2" is computed as a multi-calculation value. In addition, in FIG. 20, "D1+D2×C2" is computed as a multi-calculation value in a "normal case" and "D1+D3×C2" is computed as a multi-calculation value in a "predetermined case".

Determination by the Determination Unit

In addition, in the respective embodiments described above, while the case is described in which the determination unit of each embodiment determines whether fire has occurred in the monitored area, based on a result of comparison of a multi-calculation value and a determination threshold, a case shall not be limited thereto. For example, the determination unit of each embodiment (the determinant unit 276 in FIG. 3, for example) may compute a calculated smoke value and smoke determination threshold and determine whether fire has occurred in the monitored area, based on the comparison result of the computed values. Note that a calculated smoke value is a calculated value of the smoke concentration and is a value corresponding to a value before the CO correction B2 in FIG. 6 is performed ("D1×C1" in FIG. 6). In addition, a "smoke determination threshold" is a for determining determine whether fire has occurred, and is a value corresponding a remainder of subtraction of a value after the data conversion DC in FIG. 6 ("D2×C2" in FIG. 6) from a "determination threshold" used in the respective embodiments described above.

Relation Information

In addition, in the respective embodiments described above, while the case is described in which relation information (FIG. 9) is defined based on an experiment such as a fire test or the like, a case shall not be limited thereto. For example, the relation information may be defined based on predetermined simulation. In addition, while the case is described in which first relation information and second relation information are included, a case shall not be limited thereto. For example, the relation information may include a plurality of pieces of information that corresponds to each of combusted materials in the case in which a plurality of the combusted materials that are mutually different in kind are burnt, or, only the second relation information, for example, may be included in the relation information.

Determination of the Holding Unit

In the embodiments 3, 4 described above, the case in which when the CO gas concentration indicated by the CO data exceeds the predetermined threshold concentration, and then the concentration falls below the predetermined threshold concentration, it is determined as a "predetermined case" is described, but it is not be limited thereto. For example, a case in which after the CO gas concentration indicated by the CO data exceeds the predetermined threshold concentration, the concentration falls below the predetermined threshold concentration, and the state in which the concentration is lower than the predetermined threshold concentration has continued for a predetermined period of time may be determined as a "predetermined case". In addition, for example, a case in which the "predetermined threshold concentration" includes first threshold concentration and second threshold concentration that is different from the first threshold concentration, and after the CO gas concentration indicated by the CO data falls below both of the first and second threshold concentration after once exceeding them may be determined as a "predetermined case". If the embodiment 3 has such a configuration, a so-called hunting phenomenon can be suppressed in which the state of the holding unit 274B repeatedly changes between a state in which the holding unit 274B holds a hold value and a state the holding unit 274B in FIG. 17 does not hold a hold value due to influence of noise superimposed on the CO detection signal E2 in FIG. 17. Therefore, it is possible to prevent a multi-calculation value computed in the determination unit 276 in FIG. 17 from varying relatively substantially in a step-by-step manner, based on whether or not the holding unit 274B holds a hold value. In addition, if the embodiment 4 is thus configured, a detector 1C that operates in a stable manner can be provided, as with the embodiment 3.

Hold Value of the Holding Unit

In addition, in the embodiments 3 and 4 described above, while the case is described in which a predetermined value held as a hold value by the holding unit 274B is a fixed value, a case shall not be limited thereto. For example, the determined value may be freely adjustable after installation of detectors 1B, 1C.

In addition, in the embodiments 3 and 4 described above, while the case is described in which a predetermined value is held as a hold value, a case shall not be limited thereto. For example, the holding unit 274B in FIG. 17 or FIG. 21 may hold the CO gas concentration indicated by the past CO data as a hold value. Specifically, the holding unit 274B shall have a storage means such as a so-called ring memory that stores a predetermined number of pieces of most recent data, a monitoring means to monitor data, and a selection means to select a hold value based on a result of monitoring of the monitoring means. Then, the storage means updates data so that a predetermined number (for example, "100 pieces") of the most recent CO data outputted from the AD conversion unit 272 (FIG. 17, for example) is stored. The monitoring means monitors the CO gas concentration indicated by the CO data and determines whether being in a "predetermined case", as with the holding unit 274B. The selection means selects one piece of data from data stored in the storage means, when the monitoring means determines to be in the "predetermined case", and sets the CO gas concentration indicated by the selected data as a hold value of the holding unit 274B. Note that selection means may select as a hold value the oldest data of 100 pieces of data, for example, stored in the storage means or select as a hold value data in a predetermined ordinal number from the newest data. In addition, after the monitoring means determines to be in the "predetermined case", the storage means does not update stored data. Under such a configuration, since a hold value can be set based on a detection value actually detected by the CO sensor 16, even in the predetermined case, fire can be detected reliably, by holding as a hold value the concentration close to the CO gas concentration that is actually generated in the monitored area. In addition, for example, if the holding unit 274B determines to be in the "predetermined case", it may select one of the CO gas concentration indicated by the past CO data or a "predetermined value" in the embodiment and hold the one selected as a hold value.

In addition, in the embodiments 3 and 4 described above, while the case is described in which the holding unit 274B holds a hold value that is considered the CO gas concentration indicated by the CO data, a case shall not be limited thereto. For example, in FIG. 17 or FIG. 21, the holding unit 274B may hold a smoke hold value that is considered the smoke concentration indicated by the smoke data and the determination unit 276B may appropriately use the smoke hold value to compute a multi-calculation value. In addition, in FIG. 21, for example, the holding unit 274B may hold an external temperature hold value that is considered the external temperature indicated by the external temperature data or an internal temperature hold value that is considered the internal temperature indicated by the internal temperature data, and the determination unit 276C may appropriately use the external temperature hold value or the internal temperature hold value to compute a multi-calculation value.

Holding Time of the Holding Unit

In addition, in the embodiments 3 and 4 described above, while the case is described in which the holding unit 274B continues to hold a hold value for a period of time from when it determines to be in the "predetermined case" until the CO gas concentration indicated by the CO data exceeds a predetermined threshold again (period of time from time t12 to time t13 in FIG. 19(a), for example), a case shall not be limited thereto. For example, the holding unit 274B may continue to hold a hold value for a predetermined period of time, which is predefined, from when it determines to be in the "predetermined case". In this case, a "predetermined period of time" is 10 (seconds), 20 (seconds) or the like, for example, and may be set by a manufacturer or a user of the detectors 1B, 1C in FIG. 17 or FIG. 21. Under such a configuration, for a period of time during which CO data is relatively substantially influenced by an external factor such as wind or the like, the determination unit 276B, 276C in FIG. 17 or FIG. 21 can determine whether an abnormality has occurred, by using a hold value instead of the CO gas concentration indicated by the CO data. Thus, the influence of the external factor can be eliminated reliably and occurrence of an abnormality in the monitored area can be detected promptly and reliably. In addition, it is no longer necessary to repeatedly perform comparison processing of the CO gas concentration indicated by the CO data and predetermined threshold concentration, for example, to determine a case in which the holding unit 274B finishes holding a hold value. Thus, the detectors 1B, 1C that operate in a stable manner can be provided by reducing an amount of arithmetic operation performed in the detectors 1B, 1C and thereby reducing frequency of occurrence of false operations.

Fire Detection Processing by Receiver

In addition, in the embodiment 5 described above, while the case is described in which SG1 of FIG. 28 is performed, a case shall not be limited thereto. For example, the SG1 may be omitted and processing of SG2 to SG8 may be performed at predetermined time intervals (at intervals of a few seconds, for example). In this case, processing for the monitored area where the first detector 3 is provided may be performed based on the smoke data acquired from the first detector 3 in FIG. 24 and the CO data acquired from the second detector 4, or processing for the monitored area where the second detector 4 is provided may be performed based on the smoke data and the CO data acquired from the second detector 4.

In addition, in the embodiment 5 described above, while the case in which SG2 to SG4 are performed is described, a case shall not be limited thereto. For example, each detector may compute a multi-calculation value after the SG2 to SG4 are omitted, and acquires the computed multi-calculation value and performs processing of SG5 to SG8 based on the acquired multi-calculation value. In addition, the case of acquiring and processing an already computed multi-calculation value as in the variation and the case of computing and processing a multi-calculation value as in the embodiment 5 may be switched.

Fire Detection Processing by the Detector

In addition, in the embodiment 7 described above, while the case is described in which the first detector 9A in FIG. 32 acquires CO data from the second detector 4 by way of the receiver 9B and processes the CO data, a case shall not be limited thereto. For example, a communications means is provided in the first detector 9A and the second detector 4, respectively, so that they communicate with each other through wire or wirelessly. By using the communication means, the first detector 9A may acquire the CO data directly from the second detector 4 without going through the receiver 9B and process the CO data.

In addition, in the embodiments 5 to 7 described above, while the case is described in which the second detector in each embodiment (second detector 4 in FIG. 24, for example) determines whether an abnormality has occurred by means of a known approach (approach using a multiplication value, for example), a case shall not be limited thereto. For example, the second detector in each embodiment may compute a multi-calculation value and determine whether an abnormality has occurred by means of the computed multi-calculation value, similar to the receivers in the embodiments 5 to 7.

Communications

In addition, in the embodiments 5 to 7 described above, the "device at an acquisition destination" and the "acquired data" used in SG2 in FIG. 28 and SH2 in FIG. 31, as well as the "device at a relay source" and the "device at a relay destination" used in SJ1 in FIG. 34 are stored in advance in the receiver through manipulation and input by the user, and each processing may be performed using the stored information.

Smoke Sensor and Gas Sensor

In addition, in the respective embodiments described above, while the case is described in which the smoke sensor 15 is a so-called photoelectric smoke sensor that detects the smoke concentration based on diffused reflection of light, a case shall not be limited thereto. For example, the smoke sensor 15 may be a so-called ionization smoke sensor that detects the smoke concentration based on a change in an ionization state caused by smoke.

Moreover, in the respective embodiments described above, while the case is described in which the CO sensor 16 is a so-called electrochemical carbon monoxide concentration sensor, a case shall not be limited thereto. For example, the CO sensor 16 may be a so-called semiconductor carbon monoxide detection sensor, or a catalytic combustion carbon monoxide detection sensor.

One embodiment of the present invention provides a system comprising: a first information acquisition means configured to acquire first information indicating a detection value of a first physical quantity in a monitored area; a second information acquisition means configured to acquire second information indicating a detection value of a second physical quantity different from the first physical quantity, in the monitored area; and a determination means configured to determine whether an abnormality has occurred in the monitored area, based on the detection value of the first physical quantity indicated by the first information, the detection value of the second physical quantity indicated by the second information, a first coefficient corresponding to the detection value of the first physical quantity and the detection value of the second physical quantity, and a first threshold.

According to the above embodiment, since a first coefficient corresponding to a relation with the detection value of the first physical quantity and the detection value of the second physical quantity can be reflected in a determination of whether an abnormality has occurred in the monitored area, irrespective of magnitude of the detection value of the first physical quantity indicated by the first information and magnitude of the detection value of the second physical quantity indicated by the second information, occurrence of the fire in the monitored area can be detected promptly and reliably. Therefore, even when fire occurs in which a relatively small amount of carbon monoxide gas is generated, the first coefficient can be reflected in the determination of whether fire has occurred, irrespective of the carbon monoxide gas concentration, occurrence of the fire can be detected promptly and reliably. Alternatively, as with fumigation fire, even when fire occurs in which a relatively large amount of carbon monoxide gas is generated but an extremely small amount of smoke is generated, for example, the first coefficient corresponding to a relation with the smoke concentration and the carbon monoxide gas concentration can be reflected in the determination of whether fire has occurred, irrespective of the smoke concentration, occurrence of the fire can be detected promptly and reliably.

Another embodiment of the present invention provides the system according to the above embodiment, comprising: a first detection means configured to detect, as the first physical quantity, a concentration of a first detection target substance in the monitored area; and a second detection means configured to detect, as the second physical quantity, a concentration of a second detection target substance different from the first detection target substance, in the monitored area, wherein the first information acquisition means acquires a detection value of the first detection means as the first information, and the second information acquisition means acquires a detection value of the second detection means as the second information.

According to the above embodiment, since a first coefficient corresponding to a relation with a concentration of a first detection target substance and a concentration of a second detection target substance can be reflected in a determination of whether an abnormality has occurred in the monitored area, occurrence of the abnormality in the monitored area can be detected promptly and reliably.

Another embodiment of the present invention provides the system according to the above embodiment, comprising: an acquisition means configured to acquire the first coefficient for at least one of the detection value of the first detection means or the detection value of the second detection means, based on the detection value of the first detection means or the detection value of the second detection means, wherein the determination means determines whether the abnormality has occurred based on the first coefficient acquired by the acquisition means.

According to the above embodiment, since a first coefficient is acquired based on the detection value of the first detection means or the detection value of the second detection means, and the obtained first coefficient can be reflected in a determination of whether an abnormality has occurred, occurrence of the abnormality can be detected promptly and reliably.

Another embodiment of the present invention provides the system according to the above embodiment, wherein the first coefficient is defined in a step-by-step manner depending on a range of the concentration of the first detection target substance, and the acquisition means specifies the range of the concentration of the first detection target substance corresponding to the detection value of the first detection means, and acquires the first coefficient corresponding to the specified range of the concentration of the first detection target substance.

According to the above embodiment, since a first coefficient defined in a step-by-step manner depending on a range of the concentration of the first detection target substance is acquired, and the acquired first coefficient can be reflected in a determination of whether an abnormality has occurred, a detection error at the first detection means can be absorbed and the first conversion coefficient suitable for the environment of the monitored area can be reflected in a determination of whether an abnormality has occurred, occurrence of the abnormality can be detected promptly and reliably.

Another embodiment of the present invention provides the system according to the above embodiment, wherein the first coefficient includes a coefficient related to a first type of fire and a coefficient related to a second type of fire different from the first type of fire, the system comprises a temperature sensor configured to detect the temperature, and the acquisition means acquires one of the coefficient related to the first type of fire or the coefficient related to the second type of fire based on a detection value of the temperature sensor.

According to the above embodiment, since a first coefficient corresponding to the type of fire that is occurring in the monitored area can be acquired based on a detection result of the temperature sensor, the first coefficient corresponding to the fire that is occurring in the monitored are can be reflected in the determination of whether fire has occurred, occurrence of an abnormality in the monitored area can be detected promptly and reliably.

Another embodiment of the present invention provides the system according to the above embodiment, wherein the first type of fire is flaming fire, the second type of fire is fumigation fire, and the acquisition means acquires one of the coefficient related to the first type of fire or the coefficient related to the second type of fire based on a comparison result of the detection value of the temperature sensor and a second threshold.

According to the above embodiment, since a first coefficient corresponding to flaming fire or fumigation fire that is occurring in the monitored area can be acquired based on a detection result of the temperature sensor, the first conversion coefficient suitable for flaming fire or fumigation fire that is occurring in the monitored area can be reflected in the determination of whether fire has occurred, occurrence of an abnormality in the monitored area can be detected promptly and reliably.

Another embodiment of the present invention provides the system according to the above embodiment, wherein the first coefficient corresponds to a ratio of the concentration of the second detection target substance corresponding to the concentration of the first detection target substance with respect to the concentration of the first detection target substance in relation information that specifies the concentration of the first detection target substance and the concentration of the second detection target substance corresponding to the concentration of the first detection target substance.

According to the above embodiment, since a ratio of a second detection target substance concentration with respect to a first detection target substance concentration, which are correlated, corresponds to a first coefficient, for example, a detection value of the first detection means can be converted into a value corresponding to a detection value of the second detection means by multiplying the first conversion coefficient by the first coefficient, the determination of whether an abnormality has occurred can be made based on the criterion related to the second detection means of the first and the second detection means, and abnormality occurrence can be detected promptly and reliably.

Another embodiment of the present invention provides the system according to the above embodiment, wherein the relation information is information to specify a plurality of correspondence relations between the concentration of the first detection target substance and the concentration of the second detection target substance corresponding to the concentration of the first detection target substance, and the first coefficient is computed based on a predefined one correspondence relation of the plurality of correspondence relations.

According to the above embodiment, since a first coefficient is computed based on a predefined one correspondence relation of the plurality of correspondence relations, appropriate selection of data suitable for the determination of whether an abnormality has occurred in the monitored area, based on an experiment or the like, for example, can prevent acquisition of a coefficient unsuitable as a first coefficient, occurrence of an abnormality in the monitored area can be detected promptly and reliably.

Another embodiment of the present invention provides the system according to the above embodiment, wherein the determination means computes a sum of a product of the detection value of the first detection means and the first coefficient, and a value based on the detection value of the second detection means, and determines whether the abnormality has occurred based on a result of comparison of the computed sum and the first threshold.

According to the above embodiment, since it can be determined as to whether an abnormality has occurred based on a sum of a product of the detection value of the first detection means and the first coefficient, and a value based on the detection value of the second detection means, occurrence of an abnormality in the monitored area can be detected promptly and reliably. Therefore, even when fire occurs in which a relatively small amount of carbon monoxide gas is generated, since it can be determined as to whether fire has occurred based on the sum which is larger than a carbon monoxide gas concentration and a smoke concentration, irrespective of the carbon monoxide gas concentration, occurrence of the fire can be detected promptly and reliably. Alternatively, as with fumigation fire, even when fire occurs in which a relatively large amount of carbon monoxide gas is generated but an extremely small amount of smoke is generated, for example, since the sum becomes larger than the smoke concentration by adding the product of the carbon monoxide gas concentration and the first coefficient to the smoke concentration, occurrence of the abnormality in the monitored area can be detected promptly and reliably.

Another embodiment of the present invention provides the system according to the above embodiment further comprising: a third detection means configured to detect a physical quantity different from the physical quantities detected by the first and the second detection means, wherein the determination means determines whether the abnormality has occurred based on detection values of the first to third detection means, the first coefficient, a second coefficient corresponding to the physical quantity detected by the third detection means, and the first threshold.

According to the above embodiment, since a second coefficient corresponding to a detection value of the third detection means and a physical quantity detected by the third detection means as well as the above first coefficient can be reflected in a determination of whether an abnormality has occurred in the monitored area, irrespective of the detection values of the first to third detection means, occurrence of the abnormality in the monitored area can be detected promptly and reliably.

Another embodiment of the present invention provides the system according to the above embodiment comprising: the first detection means configured to detect the concentration of the first detection target substance in the monitored area as the first physical quantity; the second detection means configured to detect the concentration of the second detection target substance different from the first detection target substance, in the monitored area as the second physical quantity; and a holding means configured to hold, as a hold value, a past detection value by the first detection means or the second detection means or a predetermined value as a detection value of at least one of the first detection means or the second detection means, in a predetermined case, wherein the first information acquisition means acquires the detection value of the first detection means as the first information, the second information acquisition means acquires the detection value of the second detection means as the second information, and in the predetermined case, the determination means considers the hold value held by the holding means as the detection value of the first physical quantity indicated by the first information or the detection value of the second physical quantity indicated by the second information to determine whether the abnormality has occurred.

According to the above embodiment, since, in a predetermined case, a hold value held by a holding means is considered as the detection value of the first detection means or the detection value of the second detection means to determine whether the abnormality has occurred, occurrence of the abnormality in the monitored area can be detected promptly and reliably. Therefore, for example, in a predetermined case such as a case in which concentration of carbon monoxide gas or a concentration of smoke based on fire decreases due to an external factor such as wind or the like, a determination of whether fire has occurred can be made using a hold value instead of a detection value that decreases due to the external factor. Thus, any influence on the determination due to the external factor can be eliminated and occurrence of the fire can be detected promptly and reliably.

Another embodiment of the present invention provides the system according to the above embodiment wherein the first detection means is a gas sensor configured to detect the concentration of carbon monoxide as the first detection target substance, the second detection means is a smoke sensor configured to detect the concentration of smoke as the second detection target substance, and the holding means holds the hold value as a detection value of the gas sensor.

According to the above embodiment, since a hold value can be held as a detection value of a gas sensor, in a predetermined case such as a case in which a detection value of the gas sensor changes relatively largely due to an external factor such as wind or the like, a determination of whether abnormality has occurred can be made using a hold value instead of a detection value of the gas sensor so that occurrence of the abnormality in the monitored area can be detected promptly and reliably.

Another embodiment of the present invention provides the system according to the above embodiment, wherein if the first detection means or the second detection means detects lower concentration than predetermined concentration after detecting higher concentration than the predetermined concentration, the holding means determines to be in the predetermined case and holds the hold value based on the predetermined concentration.

According to the above embodiment, by holding a hold value based on a predetermined concentration as the judgment standard for judging what is the predetermined case, it is possible to hold, as the holding value, a value appropriate for judging the presence of abnormality, any influence on the determination due to the external factor can be eliminated and occurrence of the abnormality can be detected promptly and reliably.

Another embodiment of the present invention provides the system according to the above embodiment, wherein through a period of time from when the first detection means or the second detection means detects lower concentration than the predetermined concentration after detecting higher concentration than the predetermined concentration till when the first detection means or the second detection means detects higher concentration than the predetermined concentration again, the holding means continues to hold the hold value as being in the predetermined case.

According to the above embodiment, since a hold value is held through a period of time from when the first detection means or the second detection means detects lower concentration than the predetermined concentration, and, in a predetermined case, such as through a period of time from when a detection value of the first detection means or the second detection means is influenced due to an external factor such as wind or the like, a determination of whether abnormality has occurred can be made using a hold value instead of a detection value influenced by the external factor, any influence on the determination due to the external factor can be eliminated and occurrence of the abnormality can be detected promptly and reliably.

Another embodiment of the present invention provides the system according to the above embodiment, wherein the holding means continues to hold the hold value for a predetermined period of time in the predetermined case.

According to the above embodiment, since a hold value is held through a period of time, and, in a predetermined case, such as in a case that a detection value of the first detection means or the second detection means is influenced due to an external factor such as wind or the like through a period of time, a determination of whether abnormality has occurred can be made using a hold value instead of a detection value influenced by the external factor, any influence on the determination due to the external factor can be eliminated and occurrence of the abnormality can be detected promptly and reliably.

Another embodiment of the present invention provides the system according to the above embodiment, wherein the system is a receiver, the first information acquisition means acquires the first information from a first detector having the first detection means configured to detect the detection value of the first physical quantity, and the second information acquisition means acquires the second information from a second detector having the second detection means configured to detect the detection value of the second physical quantity, the second detection means being different from the first detector.

According to the above embodiment, since a first information and a second information can be acquired from a first detector having a first detection means and a second detector having a second detection means, the first information and the second information to which a first physical quantity and a second physical quantity are appropriately reflected can be acquired, occurrence of the abnormality can be detected promptly and reliably.

Another embodiment of the present invention provides the system according to the above embodiment, wherein the system is a detector, the system comprises the first detection means configured to detect the detection value of the first physical quantity, the first acquisition means acquires the detection value of the first detection means as the first information, and the second acquisition means is the second detection means provided in other detectors in a disaster prevention system configured by connecting a plurality of detectors to a receiver, and acquires, as the second information, the detection value of the second detection means configured to detect the detection value of the second physical quantity.

According to the above embodiment, since a detection value of a first detection means of the present detector can be acquired as a first information and a detection value of a second detection means of the other detector can be acquired as a second information, the first information and the second information to which a first physical quantity and a second physical quantity are appropriately reflected by separately providing the present detector and the other detector at a place suitable for detecting occurrence of abnormality, occurrence of the abnormality can be detected promptly and reliably. Further, since it is not necessary to provide the second detector to the present detector, it is possible to reduce the number of parts and to provide an inexpensive sensor.

Another embodiment of the present invention provides the system according to the above embodiment, wherein the receiver relays communications performed among the plurality of detectors, and the second acquisition means acquires the second information from the other detectors by way of the receiver.

According to the above embodiment, a second information can be acquired from the other detector through a receiver relaying communications performed among a plurality of detectors, occurrence of an abnormality can be detected promptly and reliably by preventing acquisition of the second data from being inhibited due to a communication failure and so on.

Another embodiment of the present invention provides the system according to the above embodiment, wherein the first information acquisition means acquires the first information indicating the detection value of the first physical quantity that is a physical quantity of any one of the smoke concentration, the carbon monoxide concentration, or the temperature, the second information acquisition means acquires the second information indicating the detection value of the second physical quantity that is a physical quantity of any one of the smoke concentration, the carbon monoxide concentration, or the temperature and is different from the physical quantity acquired by the first information acquisition means, and the determination means determines whether fire has occurred as the abnormality.

According to the above embodiment, since it is possible to reflect an appropriate physical quantity (e.g., concentration of smoke, concentration of carbon monoxide, or temperature) related to the state of the monitoring area in the determination of the presence of fire in the monitoring area, occurrence of fire as an abnormality in the monitoring area can be detected promptly and reliably.

Another embodiment of the present invention provides the system according to the above embodiment comprising: a third information acquisition means configured to acquire third information indicating the detection value of the temperature in the monitored area, wherein the first information acquisition means acquires the first information indicating a detection value of the smoke concentration, the second information acquisition means acquires the second information indicating a detection value of the carbon monoxide concentration, and the determination unit determines whether the abnormality has occurred in the monitored area based on the detection value of the smoke concentration indicated by the first information, the detection value of the carbon monoxide concentration indicated by the second information, the detection value of the temperature indicated by the third information, the first coefficient, the second coefficient corresponding to the detection value of the temperature indicated by the third information, and the first threshold.

According to the above embodiment, since a first coefficient and a second coefficient can be reflected in a determination of the presence of fire in a monitoring area irrespective of detection values of a smoke sensor, a gas sensor, and a temperature sensor, occurrence of fire as an abnormality in the monitoring area can be detected promptly and reliably.

The invention claimed is:

1. A system comprising:
a first information acquisition unit configured to acquire first information indicating a detection value of a smoke quantity in a monitored area;
a second information acquisition unit configured to acquire second information indicating a detection value of a carbon monoxide (CO) quantity in the monitored area;
a determination unit configured to determine whether a fire has occurred in the monitored area, based on the detection value of the smoke quantity indicated by the first information, the detection value of the CO quantity indicated by the second information, a first coefficient corresponding to the detection value of the smoke quantity and the detection value of the CO quantity, and a first threshold;
a first detection unit configured to detect, as the smoke quantity, a concentration of a first detection target substance in the monitored area; and
a second detection unit configured to detect, as the CO quantity, a concentration of a second detection target substance different from the first detection target substance, in the monitored area, wherein
the first information acquisition unit acquires a detection value of the first detection unit as the first information,
the second information acquisition unit acquires a detection value of the second detection unit as the second information,
the first coefficient corresponds to a ratio of the concentration of the second detection target substance corresponding to the concentration of the first detection target substance with respect to the concentration of the first detection target substance in relation information that specifies the concentration of the first detection target substance and the concentration of the second detection target substance corresponding to the concentration of the first detection target substance.

2. The system according to claim 1, wherein
the relation information is information to specify a plurality of correspondence relations between the concentration of the first detection target substance and the concentration of the second detection target substance corresponding to the concentration of the first detection target substance, and
the first coefficient is computed based on a predefined one correspondence relation of the plurality of correspondence relations.

3. A system comprising:
a first information acquisition unit configured to acquire first information indicating a detection value of a smoke quantity in a monitored area;
a second information acquisition unit configured to acquire second information indicating a detection value of a carbon monoxide (CO) quantity in the monitored area;
a determination unit configured to determine whether a fire has occurred in the monitored area, based on the detection value of the smoke quantity indicated by the first information, the detection value of the CO quantity indicated by the second information, a first coefficient corresponding to the detection value of the smoke quantity and the detection value of the CO quantity, and a first threshold;

a first detection unit configured to detect, as the smoke quantity, a concentration of a first detection target substance in the monitored area; and a second detection unit configured to detect, as the CO quantity, a concentration of a second detection target substance different from the first detection target substance, in the monitored area, wherein the first information acquisition unit acquires a detection value of the first detection unit as the first information, the second information acquisition unit acquires a detection value of the second detection unit as the second information, the determination unit computes a sum of a product of the detection value of the first detection unit and the first coefficient, and a value based on the detection value of the second detection unit, and determines whether the fire has occurred based on a result of comparison of the computed sum and the first threshold.

* * * * *